(12) United States Patent
Hirao et al.

(10) Patent No.: US 7,144,702 B2
(45) Date of Patent: Dec. 5, 2006

(54) METHOD FOR DETECTING TARGET PLANT GENUS

(75) Inventors: Takashi Hirao, Higashi-Osaka (JP); Masayuki Hiramoto, Higashi-Osaka (JP)

(73) Assignee: House Foods Corporation, Osaka-fu (JP)

( * ) Notice: Subject to any disclaimer, the term of this patent is extended or adjusted under 35 U.S.C. 154(b) by 512 days.

(21) Appl. No.: 10/285,061

(22) Filed: Oct. 31, 2002

(65) Prior Publication Data

US 2003/0207298 A1   Nov. 6, 2003

(30) Foreign Application Priority Data

Nov. 1, 2001   (JP)   ............................. 2001-336571
Sep. 27, 2002   (JP)   ............................. 2002-284222

(51) Int. Cl.
*C12Q 1/68*   (2006.01)
*C12P 19/34*   (2006.01)

(52) U.S. Cl. .......................... 435/6; 435/91.1; 435/91.2
(58) Field of Classification Search ..................... None
See application file for complete search history.

(56) References Cited

U.S. PATENT DOCUMENTS 5,876,977 A * 3/1999 Wang et al. ............... 435/91.2
5,962,665 A * 10/1999 Kroeger et al. ............ 536/23.1

OTHER PUBLICATIONS

Lott et al., Nucleotide Sequence Analysis of the 5.8S rDNA and Adjacent ITS2 Region of Candida albicans and Related Species. Yeast (1993) 9:1199.*
Holzhauser et al., Polymerase chain reaction (PCR) for detection of potentially allergenic hazelnut residues in complex food matrixes. Eur. Food Res. Technol. (2000) 211: 360-365.*
Hartmann et al., Extensive Ribosomal DNA Genic Variation in the Columnar Cactus Lophocereus. Mol. Evol. (2001) 53: 124-134.*
Lavin et al., The Dalbergioid Legumes (Fabeceae): Delimitation of a pantropical monophyletic clade. Amer. J. Bot. (2001) 88: 503-533.*
Buck et al., Design Strategies and Performance of Custom DNA Sequencing Primers. BioTechniques (1999) 27: 528-536.*
Jong Hee Shin et al., Rapid Identification of up to Three Candida Species in a Single Reaction Tube by a 5' Exonuclease Assay Using Fluorescent DNA Probes, Journal of Clinical Microbiology, Jan. 1999, p. 165-170, vol. 37, No. 1 (Abstract).
Jana Proft et al., Identification of six sibling species of the Anopheles macilipennis complex (Diptera: Culicidae) by a polymerase chain reaction assay, Parasitol Res (1999), 85: 837-843.
Michael Allmann et al., Polymerase chain reaction (PCR): a possible alternative to immunochemical methods assuring safety and quality of food; Z Lebensm Unters Forsch (1993) 196:248-251.

* cited by examiner

*Primary Examiner*—Jeffrey Fredman
(74) *Attorney, Agent, or Firm*—Hoffmann & Baron, LLP

(57) ABSTRACT

A method for detecting species in a target plant genus comprises the steps of conducting PCR using at least one member selected from the group consisting of primers (A) and (B), which can hybridize under stringent conditions to a nucleic acid molecule having a common nucleotide sequence for all species in the target plant genus in 45S rRNA precursor gene sequence thereof, wherein 3' end of primer (A) can complementarily bind to a base in ITS-1 sequence of the target plant genus when the primer hybridizes to the nucleic acid molecule while 3' end of primer (B) can complementarily bind to a base in ITS-2 sequence of the target plant genus when the primer hybridizes to the nucleic acid molecule, and identifying the presence of the resulting amplification product from PCR containing at least a part of ITS-1 or ITS-2 sequence of the target plant genus.

The method for detecting species in a target plant genus, particularly an allergenic plant genus such as the genus *Fagopyrum,* can make it possible to detect with high sensitivity, for example, about 1 ppm of the plant(s) in cases where the plant(s) is contained in a food ingredient or food product.

21 Claims, 10 Drawing Sheets

FIG. 4

```
                       SENSE PRIMER REGION
             1            10           20           30           40           50
             |            |            |            |            |            |
1. FAGOPYRUM ESCULENTUM(AB000330) GGACCACGAAACAGAAGCGGCGTCCCGAGCCTCCCGGTCCCCGGGGCGGCACG
2. SAMPLE                                         AGCCTCCCGGTCCCCGGGSGGGCACG
                                                  ***************** ********

60           70           80           90          100
             |            |            |            |            |
1. FAGOPYRUM ESCULENTUM(AB000330) GCGGGCGTCGCGTCGTTTCTACGAAACAGAACGACTCTCGGCAACGGATAT
2. SAMPLE                         GCGGGCGTCGCGTCGTTTCTACGAAACAGAACGACTCTCGGCAACGGATAT
                                  ***************************************************

110          120          130          140
             |            |            |            |
1. FAGOPYRUM ESCULENTUM(AB000330) CTCGGCTCTCGCATCGATGAAGAACGTAGCGAAATGCGAT
2. SAMPLE                         CTCGGCTCTCGC--
                                  ************
                                                    ANTISENSE PRIMER REGION
```

FIG. 12

SENSE PRIMER REGION

```
              1           10          20          30          40          50
1. ARACHIS HYPOGAEA(AF156675)    CGGCTTCCGGAGACGGCCATCCGGTCGGG-CGAGGAGTGACCACAAGAGTT
2. ARACHIS CORRENTINA(AF203554)  CGGCT-CCGGAGACGGCCATCCGGTCGGGGCGACGAGTGACCACAAGAGTT
3. ARACHIS VILLOSA(AF203558)     CGGCT-CCGGAGACGGCCATCCGGTCGGGGCGACGAGTGACCACAAGAGTT
4. ARACHIS MAJOR(AF203552)       CGGCT-CCGTAGACGGCCATCCGGTCGGGGCGACGAGTGACCACAAGAGTT
5. ARACHIS HERMANNI(AF203556)    CGGCT-CCGTAGACGGCCATCCGGTCGGGGCGACGAGTGACCACAAGAGTT
6. COMMERCIALLY AVAILABLE PEANUT
7. SAMPLES                               TCCGGTCGGGGCGACGAGTGACCACAAGAGTT
                                         ***** *** ********************

60          70          80          90          100
1. ARACHIS HYPOGAEA(AF156675)    AAAGAACGACTCTCGGCAACGGATATCTCTCG-CTCTTGCATCGATGAAGAA
2. ARACHIS CORRENTINA(AF203554)  AA-GAACGACTCTCGGCAACGGATATCTCGGCTCTTGCATCGATGAAGAA
3. ARACHIS VILLOSA(AF203558)     AA-GAACGACTCTCGGCAACGGATATCTCGGCTCTTGCATCGATGAAGAA
4. ARACHIS MAJOR(AF203552)       AA-GAACGACTCTCGGCAACGGATATCTCGGCTCTTGCATCGATGAAGAA
5. ARACHIS HERMANNI(AF203556)    AA-GAACGACTCTCGGCAACGGATATCTCGGCTCTTGCATCGATGAAGAA
6. COMMERCIALLY AVAILABLE PEANUT AA-GAACGACTCTCGGCAACGGATATCTCGGCTCTTGCATCGAT
7. SAMPLES                       ** ********************* *********** ***********

110   116
1. ARACHIS HYPOGAEA(AF156675)    CGTAGCGAAATGCGAT
2. ARACHIS CORRENTINA(AF203554)  CGTAGCGAAATGCGAT
3. ARACHIS VILLOSA(AF203558)     CGTAGCGAAATGCGAT
4. ARACHIS MAJOR(AF203552)       CGTAGCGAAATGCGAT
5. ARACHIS HERMANNI(AF203556)    CGTAGCGAAATGCGAT
6. COMMERCIALLY AVAILABLE PEANUT CGTAGCGAAATGCGAT
7. SAMPLES                       ****************
```

ANTISENSE PRIMER REGION

METHOD FOR DETECTING TARGET PLANT GENUS

CROSS-REFERENCE TO RELATED APPLICATIONS

This application claims priority to Japanese Patent Application Nos. 2002-284222 filed on Sep. 27, 2002 and Japanese Patent Application No. 2001-336571 filed on Nov. 1, 2001.

BACKGROUND OF THE INVENTION

The 45S rRNA precursor gene sequence (Small Subunit ribosomal RNA (SSU rRNA) gene~Internal Transcribed Spacer-1 (ITS-1)~5.8S ribosomal RNA (5.8S rRNA) gene~Internal Transcribed Spacer-2 (ITS-2)~Large Subunit ribosomal RNA (LSU rRNA) gene) has been used for the classification of species. For example, according to the method developed by Shin J H, et al. (J. Clin. Microbiol., 37: 165–170(1999)), 5 candida species (fungi) of the genus Candida can be detected and identified using two primers hybridized to the 5.8S rRNA and 28S rRNA (LSU rRNA) gene sequences common to fungi and 5 separate probes each of which can specifically hybridize to the ITS-2 sequence of its corresponding species. The method is different from the present invention as described below. Firstly, the method is aimed at fungi, specifically candida (fungi). Secondly, the method does not use the primers, which hybridize to ITS-1 or ITS-2 sequence. Consequently, these primer pairs do not assure the specificity to the genus Candida, whereas each of five probes can independently recognize its corresponding candida species (fungi) of the genus Candida. In other words, only one species of the genus Candida can be detected and identified when a single set of the primer pair and a probe is used. Thirdly, the above publication does not describe about the sensitivity of the detection, which is very important for the detection methods of allergenic plants in food. Lastly, the method needs expensive reagents and instruments due to the use of probes.

According to the method developed by Proft J, et al. (Parasitol. Res., 85: 837–843(1999)), a certain anopheles mosquito can be classified into one of 6 species of the genus Anopheles using 6 primer pairs. The method uses a primer that can hybridize to the 5.8 rRNA gene sequence common to the six anopheles mosquito species of the genus Anopheles in combination with 6 primer pairs each of which can specifically hybridize to the ITS-2 sequence of its corresponding anopheles mosquito species of the genus Anopheles. Based on the size of the amplification product obtained by PCR method, the anopheles mosquito of interest can be classified into one of the 6 species of the genus Anopheles. The method is different from the present invention as described below. Firstly, the method is aimed at mosquitoes, specifically the anopheles mosquitoes. Secondly, due to the properties of designed primer pairs, only one species of the genus Anopheles can be detectable when a single primer pair is used. Thirdly, an object of the method is to identify a specimen exclusively derived from a single species of mosquitoes. Consequently, the object of the method is not to analyze anopheles mosquitoes in a mixture. Lastly, the above publication does not describe about the sensitivity of the detection, which is very important for the detection methods of allergenic plants in food.

Thus, the conventional methods mentioned above are to detect one specific species in a mixture and to identify a bio specimen exclusively derived from a single species of the genus, and therefore, the methods do not relate to a method for detecting the target genus broadly in cases where even one kind of the target genus is contained in a mixture. In addition, the primer sequences common to several species are located on SSU rRNA, 5.8S rRNA and LSU rRNA gene sequence, and therefore, primer sequences common to several species are not found in ITS-1 or ITS-2 sequence.

On the other hand, regarding detection of allergenic plants in food, a method for detecting whether some wheat is contained in a food sample of interest is disclosed by Allmann M, et al. (Z Lebensm Unters Forsch, 196: 248–251 (1993)). The method uses primers which specifically hybridize to a IGS sequence between 25S rRNA (LSU rRNA) and 18S rRNA (SSU rRNA) gene sequences of wheat. However, it is hard to evaluate the specificity of the primers by simulation and the like because the primers have to be designed based on little information about the IGS sequence in the method. Therefore, it would be difficult to judge the reliability of the analysis.

SUMMARY OF THE INVENTION

An object of the present inventions is to provide a method for detecting species (a plant or plants) in a target plant genus, particularly an allergenic plant genus such as the genus Fagopyrum, which makes it possible to detect with high sensitivity, for example, about 1 ppm of the plant(s) in cases where the plant(s) is contained in a food ingredient or food product.

Since a trace of allergenic food ingredients, particularly plants in an allergenic plant genus may be unintentionally contaminated in the food ingredient or product at the stages of production, distribution and fabrication, it is important that providers of the food ingredient or product conduct quality control to detect whether these plants have contaminated the food ingredient or product.

For example, regarding buckwheat, though it is reported that patients are affected with anaphylaxis by pillows made of buckwheat chaff and die due to anaphylactic shock and traces of buckwheat may effect a severe symptom in allergic patients for buckwheat, there is no method for detecting buckwheat in the food ingredient or product in the world. For example, it is considered that contamination of buckwheat into the food ingredient or product occurs in a case where buckwheat grown near a field cultivated with plants other than buckwheat is contaminated in the food ingredient harvest time. Therefore, in order to find the contamination of trace of unintended buckwheat, it is desirable that a method for detecting buckwheat be built up, wherein the method can detect as sensitive as possible, for example, even 1 ppm of the buckwheat in a food ingredient and product. Furthermore, as for grain allergies, it is said that some cross-reaction occurs among taxonomically related plants, and therefore, it is desirable that the method be able to detect a wide range of any plants in the genus Fagopyrum without limiting the detectable plants to eatable buckwheat.

Regarding a method for detecting peanuts, an ELISA kit, which can detect about 2.5 ppm of peanuts using specific antibodies for proteins inherent to peanuts, have been sold and used in the world. When positive finding in ELISA, whether it is false positive or truly positive can be confirmed in detail by Western Blot etc., but it confirms only the size of protein involving antigen-antibody reaction. A method for detecting a DNA inherent to peanuts has not been reported. In order to detect peanuts in a food ingredient and product through a variety of processing steps, it is desirable that there is built up a method for detecting target DNA sequences, which will have a relatively high resistivity against the processing rather than proteins. Furthermore, as it is the same as in buckwheat, it is desirable that the method be able to detect a wide range of plants in the genus *Arachis*.

Thus, it is important to detect a plant(s) in the allergenic plant genus with high sensitivity in cases where even only one kind of the plants is contained in the food ingredient, product and the like.

In cases of genetically modified products and the like, DNA sequences to be detected are limited to recombinant DNA sequences. On the other hand, 6 in cases of plants which originally exist in nature, there has not been clear knowledge how to choose a target DNA sequence from a large number of DNA sequences, and whether the thus chosen DNA sequence is useful and universal for a variety of plants. It has been conducted to choose a specific protein to a target plant, and to detect a DNA sequence coding for the protein, but it is necessary to choose a separate specific protein to each plant. Furthermore, even if such a specific protein can be chosen, when the copy number of a DNA sequence coding for the protein is small, there are some cases where the method may not have a sufficient sensitivity and therefore it will be disadvantage for the detection of traces of a contaminating plant.

Under such circumstances, in order to develop a method for detecting a plant(s) in an allergenic plant genus and the like in cases where even only one kind of the plants is contained in a food ingredient and product, the present inventors have focused their attention on the gene sequences of a target plant genus to vigorously conduct the research. In order to detect whether one specific plant has contaminated a food ingredient or product, it may be conducted to detect a specific gene sequence of the plant in the food ingredient and product. However, in order to detect a case where even only one kind of the plants is contained in a genus in a food ingredient and product, such method is very complicated and inefficient because it is necessary to repeat the same operation for respective plants in a specific genus.

In order to solve this problem, the inventors have conducted further research, collected some information on gene sequences of plants in the genus *Fagopyrumn* (21 sequences registered in GenBank) and in other genus and studied on a variety of viewpoint, and thereby, the inventors have found that a specific common sequence for plants in the genus *Fagopyrum*, which differs from a sequence of plants in other genus, is present in gene sequences of the plant in the genus *Fagopyrum* (21 sequences registered in GenBank). As the result of an investigation conducted based on this knowledge for other plant genus such as the genus *Arachis,* the inventors have also found that there is similar tendency among them.

Based on this knowledge, it has been found that a method for detecting each allergenic plant genus using a sequence of 45S rRNA precursor gene, as a sequence which exists as a sequence having a large copy number in plant DNA and is specific to each allergenic plant genus, can be useful in attaining the object. When positive indication appears in PCR, differently from ELISA, as an amplification product can be analyzed not only in the size thereof but also in detail sequence thereof by sequencing the amplification product, it can be confirmed more precisely whether it is false positive or truly positive. Furthermore, it has been found that, by choosing a region including ITS-1 or ITS-2 sequence as a target sequence, the method is useful in detecting trace of plants in the target plant genus in a mixture because the specific sequence can be obtained and common region of sequences for plants in the genus can be chosen. Moreover, as the sequence of 45S rRNA precursor gene is present in most plants, it can be advantageously applied on a variety of plants.

Based on this knowledge, the present inventions have been completed. In this connection, the following method for detecting plants can be applied not only to the allergenic plant genus but also to other plant genus.

Accordingly, the present invention provides a method for detecting species (a plant(s)) in a target plant genus, which comprises the steps of conducting PCR using at least one member selected from the group consisting of primers (A) and (B), which can hybridize under stringent conditions to a nucleic acid molecule having a nucleotide sequence common to all species in the target plant genus in 45S rRNA precursor gene sequence thereof, wherein 3' end of primer (A) can complementarily bind to a base in a ITS-1 sequence of the target plant genus when the primer hybridizes to the nucleic acid molecule while 3' end of primer (B) can complementarily bind to a base in a ITS-2 sequence of the target plant genus when the primer hybridizes to the nucleic acid molecule, and identifying the presence of the resulting amplification product from PCR containing at least a part of the ITS-1 or ITS-2 sequence of the target plant genus.

Herein, the phrase "hybridize under stringent conditions" means that two DNA fragments hybridize to each other under the standard hybridization condition described by Sambrook J. et al. (Expression of Cloned Genes in *E. coli* (Molecular Cloning : A laboratory Manual (1989)) Cold Spring Harbor Laboratory Press, New York, USA, 9.47–9.62 and 11.45–11.61). More specifically, for example, it means that a hybridization and washing (for example, about 2.0×SSC, 50° C.) are conducted on the basis of Tm value obtained by the following equation.

$$Tm = 81.5 + 16.6(\log_{10}[Na^+]) + 0.41(\text{fraction } G+C) - (600/N)$$

In addition, the term genus as used in the present specification means a group including all species in the genus or some species chosen from the species in the genus.

BRIEF DESCRIPTION OF THE DRAWINGS

FIG. 4 is nucleotide sequences obtained by a sequence analysis of the target amplification product from buckwheat chaff.

FIG. 12 is nucleotide sequences obtained by a sequence analysis of the target amplification product from peanut.

DESCRIPTION OF THE PREFERRED EMBODIMENTS

Figure 1:
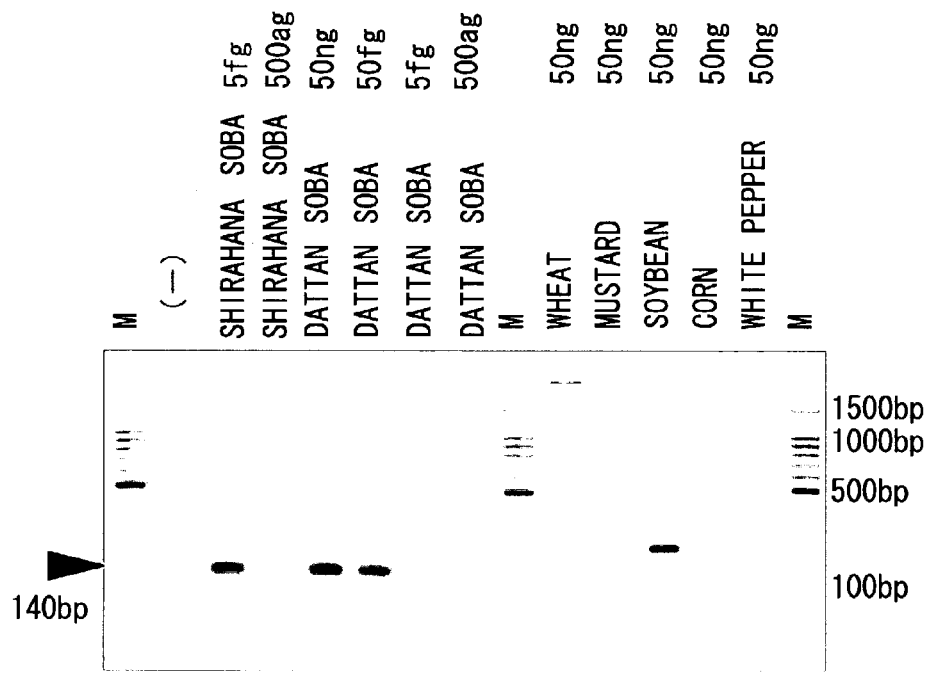
FIG. 1 is an electrophoretogram showing the results electrophoresed on a 2% agarose gel in Example 1.

Although a target plant genus to be detected by the method of the present invention may be any plant genus, because the method can detect a presence of trace of a plant(s) in the target plant genus in a food ingredient or product, the method is particularly useful in detecting whether plants in the allergenic plant genus such as the genus *Fagopyrum*, genus *Arachis,* genus *Triticum* and genus *Glycine* are contaminated in the food ingredient or product.

The method of the present inventions uses at least one member selected from the group consisting of primers (A) and (B), which can hybridize under stringent conditions to a nucleic acid molecule having a nucleotide sequence common to all species in the target plant genus in a 45S rRNA precursor gene sequence thereof, wherein 3' end of primer (A) can complementarily bind to a base in a ITS-1 sequence of the target plant genus when the primer hybridizes to the nucleic acid molecule, while 3' end of primer (B) can complementarily bind to a base in a ITS-2 sequence of the target plant genus when the primer hybridizes to the nucleic acid molecule to conduct PCR amplification for DNA isolated from a subject to which the method is to be applied. In the PCR amplification, based on a conventional procedure described in publications, for example, Saiki RK, et al., Science, 230: 1350–1354(1985) and Shyokubutsu no PCR Zikken Protocol—Idenshi no Tanri•Hatsugen Kara Genome Kaiseki Made—(Saiboukougaku Bessatsu Saiboukougaku Series 2), General Editors Shimamoto, K. and Sasaki, T., Shujunsha Co., Ltd., Tokyo, 1995 and the like, optimal conditions are chosen from appropriate modification of temperature and time of each step of denaturation, annealing and extension, a kind and concentration of enzyme (DNA polymerase), concentrations of DNTP, primer and magnesium chloride, an amount of template DNA and the like.

In addition, PCR amplification may be conducted at an annealing temperature of the primer and the template DNA higher than Tm value of the primer, preferably the Tm value plus 10 to 3° C., and subsequently at an annealing temperature near the Tm value, preferably the Tm value plus 7 to 0° C. , wherein the Tm value is determined by commercially available software such as HYB Simulator™ version 4.0 (Advanced Gene Computing Technologies, Inc.) and Primer Express™ version 1.5 (PE Applied Biosystems).

After the PCR amplification of DNA isolated from a subject to be studied such as a food ingredient or product, the resulting reaction solution is analyzed by for example, electrophoresis to determine whether the target plant genus is present in the subject. The determination is based on whether any PCR amplification products having target size are present in the reaction solution after the PCR amplification, and if the PCR amplification products are present in the reaction solution, whether at least a part of the ITS-1 or ITS-2 sequence of the target plant genus is present in the sequence of the PCR amplification products. That is, if the PCR amplification products, which have the target size and contain at least a part of the ITS-1 or ITS-2 sequence of the target plant genus, are present in the reaction solution, the studied subject is contaminated by a plant(s) in the target plant genus. On the other hand, if the PCR amplification products are not present in the reaction solution or even though it exists, unless it contains at least a part of ITS-1 or ITS-2 sequence of the target plant genus, the studied subject is not contaminated by a plant(s) in the target plant genus. Furthermore, the method of the present invention can detect with high sensitivity, for example, about 1 ppm level of a contamination.

For example, at least 2 primers may be used in the method of the present invention. In cases where at least 2 kinds of the target plant genus are detected at the same time, at least 3 primers may be used provided that it is important to use at least one member selected from the group consisting of primers (A) and (B), which can hybridize under stringent conditions to a nucleic acid molecule having a nucleotide sequence common to all species in the target plant genus in 45S rRNA precursor gene sequence thereof, wherein 3' end primer (A) can complementarily bind to a base in ITS-1 sequence of the target plant genus when the primer hybridizes to the nucleic acid molecule while 3' end of primer (B) can complementarily bind to a base in ITS-2 sequence of the target plant genus when the primer hybridizes to the nucleic acid molecule. In this connection, examples of the primer (A) include primers, which can hybridize to a nucleic acid molecule having a boundary between a ITS-1 sequence and a 5.8S rRNA gene sequence or which can hybridize to a nucleic acid molecule having a boundary between a ITS-1 sequence and a SSU rRNA gene sequence. Likewise, examples of the primer (B) include primers, which can hybridize to a nucleic acid molecule having a boundary between a ITS-2 sequence and a 5.8S rRNA gene sequence or which can hybridize to a nucleic acid molecule having a boundary between a ITS-2 sequence and a LSU rRNA gene sequence. Preferably the primers (A) and (B) have at least 15 bases, more preferably 15 to 30 bases. Since the ITS-1 sequence and the ITS-2 sequence contain many specific sequences for species, the primer (A) or (B), which has a specificity common to the target plant genus, can be obtained by choosing a suitable nucleic acid molecule having a specific nucleotide sequence common to the target plant genus in the ITS-1 and ITS-2 sequences, as a nucleic acid molecule having a nucleotide sequence common to the target plant genus in the 45S rRNA precursor gene sequence. One or two or more member(s) selected from the group consisting of the primer (A) and the primer (B) may also be used, but if at least two members are used, the method of the present invention can become more highly sensitive to the target plant genus, particularly genus *Fagopyrum*.

In another embodiment of the method for detection of the present invention, primer (A) is used together with a primer (C) which can hybridize under stringent conditions to a nucleic acid molecule having a part of a nucleotide sequence continuously bonded ITS-1, 5.8S rRNA gene, ITS-2 and LSU rRNA gene of the target plant genus. Alternatively, primer (A) is used together with a primer (E) which can hybridize under stringent conditions to a nucleic acid molecule having a part of a nucleotide sequence continuously bonded SSU rRNA gene and ITS-1 of the target plant genus. In a further embodiment of the method for detection of the present invention, the primer (B) is used together with a primer (D) which can hybridize under stringent conditions to a nucleic acid molecule having a part of a nucleotide sequence continuously bonded SSU rRNA gene, ITS-1, 5.8S rRNA gene and ITS-2 of the target plant genus. Alternatively, primer (B) is used together with a primer (F) which can hybridize under stringent conditions to a nucleic acid molecule having a part of a nucleotide sequence continuously bonded ITS-2 and LSU rRNA gene of the target plant genus. In this connection, 5.8S rRNA gene is highly preservative and contains many sequences common to a great majority of plants. Therefore, as a primer (C), by appropriately choosing a primer, which can hybridize under stringent conditions to a nucleic acid molecule having a part of a nucleotide sequence of 5.8S RRNA gene, wherein 3' end thereof can complementarily bond to a nucleotide sequence in 5.8S rRNA gene sequence when the primer hybridizes to the nucleic acid molecule, or as s primer (D), by appropriately choosing a primer, which can hybridize under stringent conditions to a nucleic acid molecule having a part of a nucleotide sequence of 5.8S rRNA gene, wherein 3' end thereof can complementarily bond to a nucleotide sequence in 5.8S rRNA gene sequence when the primer hybridizes to the nucleic acid molecule, the resulting primer can be commonly used for a variety of plants. If said primer is fixed and a common specific primer is chosen for the species in the target plant genus from the ITS-1 or ITS-2 region thereof, then the primers can be easily designed to detect with high sensitivity the contaminated plants in the target plant genus. Preferably, the primers (C) to (F) have at least 15 bases, more preferably 15 to 30 bases.

When these primers are designed, it will be sufficient to design them based on, for example, PCR Hou Saizensen—Kisogizyutsu Kara Ouyou Made (Tanpakushitsu•Kakusan•Kouso Rinzizoukan), ed. Sekiya, T. and Fujinaga, K., Kyoritsu Shuppan Co. Ltd., Tokyo, 1997, Baio Zikken Illustrated 3 Hontouni Hueru PCR (Saiboukougaku Besshi Me de Miru Zikken Note Series), Nakayama, H., Shujunsha Co., Ltd., Tokyo, 1996 or PCR Technology: Principles and Applications of DNA Amplification, ed. Erlich, H. A., Stockton Press, Inc., NY, 1989. However, since there is a low possibility that the target DNA is decomposed when the DNA is detected in un-processed materials, the primers may be those which can induce an amplification product within 700 bases, and since there is a possibility that the target DNA is decomposed to become short when the DNA is detected in processed foods, the primers, which can induce an amplification product within 200 bases, are preferable in view of that the primers provide high sensitivity.

In view of the above, it is preferable that the primer (C) or (D) be able to hybridize under stringent conditions to a nucleic acid molecule having a nucleotide sequence indicated by SEQ NO:1 or a complementary nucleotide sequence thereof. Said primer is preferable because the region indicated by SEQ NO:1 has an especially high homology, a primer which hybridize to any region of 5.8S rRNA gene sequence may be used because the sequences of species in the allergenic plant genus have a high homology over almost the whole region of 5.8S rRNA gene sequence. More preferably, it is a primer, which can hybridize under stringent conditions to a nucleic acid molecule having positions 11 to 63 of the nucleotide sequence of SEQ NO:1 or a complementary nucleotide sequence thereof. Preferably, primer (C) is an oligonucleotide indicated by any of SEQ NO:2, 3 or 4, which hybridizes to the nucleic acid molecule of SEQ NO:1. Preferably, primer (D) is also an oligonucleotide indicated by any of SEQ NO:5, 6 or 7, which hybridizes to a complementary strand of SEQ NO:1. Said primers have to hybridize under stringent conditions specific to the target nucleic acid molecule and 3' end thereof have to be a complementary base to the target part of DNA sequence so that the hybridized primers can function as one primer and an extension reaction occurs. Therefore, as long as the primers meet the above requirement, the primers may be an oligonucleotide indicated by any nucleotide sequence of SEQ NOs:2 to 7, wherein one or several base(s) thereof are deleted or substituted, or one or several base(s) are added thereto.

The specific nucleotide sequence common to the target plant genus in ITS-1 or ITS-2 sequence can be identified by obtaining the ITS-1~5.8S rRNA gene~ITS-2 sequence of a plant(s) in the target plant genus to be detected and other plant genus from GenBank, conducting an alignment and searching a region having a high specificity common to the target plant genus. In addition, among the regions thus identified, a base, which can assure that the base is specific to the target plant genus and not to plants thought to be related species thereof, can be determined as 3' end of the primers to select a primer sequence.

When the target plant genus is the genus *Fagopyrum*, examples of a commonly specific nucleotide sequences in the ITS-1 sequence thereof include a nucleotide sequence indicated by any of SEQ NO:8, 9 or 10, or a complementary nucleotide sequence thereof Preferably, they include a nucleotide sequence of positions 11 to 61 of the nucleotide sequence of SEQ NO:8 or a complementary nucleotide sequence thereof, or a nucleotide sequence of positions 11 to 67 of the nucleotide sequence of SEQ NO:9 or a complementary nucleotide sequence thereof In addition, SEQ NO:10 is particularly useful as a region for selecting primers for detecting specifically *F. esculentum* (common buckwheat), *F. tataricum* (Tartarian buckwheat), *F. homotropicuam* and/or *F. cyniosum*, which are members of the genus *Fagopyrum*.

Preferably, the primer (A) is an oligonucleotide indicated by any of SEQ NOs:11 to 16 wherein the oligonucleotide indicated by any of SEQ NOs:11 to 14 hybridizes to a complementary strand of SEQ NO:8 and the oligonucleotide indicated by any of SEQ NOs:15 and 16 hybridizes to a nucleic acid molecule of SEQ NO:9. The primer (A) may also be an oligonucleotide indicated by any nucleotide sequence of SEQ NOs:11 to 16, wherein one or several base(s) thereof are deleted or substituted, or one or several base(s) are added thereto. Furthermore, examples of the common specific nucleotide sequence in ITS-2 include a nucleotide sequence indicated by any of SEQ NO:21 or 22, or a complementary nucleotide sequence thereof These nucleotide sequences are particularly useful as a region for selecting primers for detecting specifically *F. esculentum* (common buckwheat), *F. tataricum* (Tartarian buckwheat), *F. homotropicum* and/or *F. cymsosum*, which are members of the genus *Fagopyrum*. In addition, it is preferable to use a combination of the primer of any of SEQ NOs:11 to 14 and the primer of any of SEQ NOs:15, 16 or 2 to 4.

When the target plant genus is the genus *Arachis*, examples of a common specific nucleotide sequences in the ITS-1 sequence thereof include a nucleotide sequence indicated by SEQ NO:17, or a complementary nucleotide sequence thereof. Preferably, they include a nucleotide sequence of positions 1 to 60 of the nucleotide sequence of SEQ NO:17 or a complementary nucleotide sequence thereof, or a nucleotide sequence of positions 43 to 99 of the nucleotide sequence of SEQ NO:17 or a complementary nucleotide sequence thereof. More preferably, they include a nucleotide sequence of positions 11 to 50 of the nucleotide sequence of SEQ NO:17 or a complementary nucleotide sequence thereof, or a nucleotide sequence of positions 53 to 89 of the nucleotide sequence of SEQ NO:17 or a complementary nucleotide sequence thereof Preferably, the primer (A) is an oligonucleotide indicated by any of SEQ NOs:18 to 20, which hybridizes to a complementary strand of SEQ NO:17. The primer (A) may also be an oligonucleotide indicated by any nucleotide sequence of SEQ NOs:18 to 20, wherein one or several base(s) thereof are deleted or substituted, or one or several base(s) are added thereto. Furthermore, examples of the common specific nucleotide sequence in ITS-2 sequence of the genus *Arachis* include a nucleotide sequence of SEQ NO:23 or a complementary nucleotide sequence thereof Preferably, it is a nucleotide sequence of positions 11 to 47 of the nucleotide sequence of SEQ NO:23 or a complementary nucleotide sequence thereof. Moreover, it is preferable that the primer (B) be an oligonucleotide indicated by SEQ NO:24, which hybridizes to a nucleic acid molecule of SEQ NO:23. The primer (B) may also be an oligonucleotide indicated by any nucleotide sequence of SEQ NO:24, wherein one or several base(s) thereof are deleted or substituted, or one or several base(s) are added thereto. In addition, it is preferable to use a combination of the primer of any of SEQ NOs:18 to 20 and the primer of any of SEQ NOs: 2 to 4, a combination of the primer of any of SEQ NOs:18 to 20 and the primer of SEQ NO:24 or a combination of the primer of SEQ NO:24 and the primer of any of SEQ NOs:5 to 7, and more preferably, a combination of the primer of any of SEQ NOs:18 to 20 and the primer of any of SEQ NOs:2 to 4.

When the target plant genus is genus *Tritictim,* examples of common specific nucleotide sequences in ITS-2 sequence thereof include a nucleotide sequence indicated by any of SEQ NO:25, 26 or 27, or a complementary nucleotide sequence thereof. Preferably, it is a nucleotide sequence of positions 11 to 50 of the nucleotide sequence of SEQ NO:25 or a complementary nucleotide sequence thereof, a nucleotide sequence of positions 11 to 47 of the nucleotide sequence of SEQ NO:26 or a complementary nucleotide sequence thereof, or a nucleotide sequence of positions 11 to 47 of the nucleotide sequence of SEQ NO:27 or a complementary nucleotide sequence thereof.

Preferably, the primer (B) is an oligonucleotide indicated by any of SEQ NOs:28 to 30 wherein the oligonucleotide of SEQ NO:28 hybridizes to the complementary strand of SEQ NO:25, the oligonucleotide of SEQ NO:29 hybridizes to the nucleic acid molecule of SEQ NO:26 and the oligonucleotide of SEQ NO:30 hybridizes to the nucleic acid molecule of SEQ NO:27. The primer (B) may also be an oligonucleotide indicated by any nucleotide sequence of SEQ NOs:28 to 30, wherein one or several base(s) thereof are deleted or substituted, or one or several base(s) are added thereto. In addition, it is preferable to use a combination of the primer of SEQ NO:28 and at least one primer selected from the group consisting of SEQ NOs:29 and 30.

When the target plant genus is genus *Glycine,* examples of commonly specific nucleotide sequences in ITS-2 sequence thereof include a nucleotide sequence indicated by any of SEQ NO:31, 32 or 33, or a complementary nucleotide sequence thereof Preferably, it is a nucleotide sequence of positions 11 to 48 of the nucleotide sequence of SEQ NO:31 or a complementary nucleotide sequence thereof, a nucleotide sequence of positions 11 to 55 of the nucleotide sequence of SEQ NO:32 or a complementary nucleotide sequence thereof, or a nucleotide sequence of positions 11 to 52 of the nucleotide sequence of SEQ NO:33 or a complementary nucleotide sequence thereof Preferably, the primer (B) is an oligonucleotide indicated by any of SEQ NOs:34 to 41 wherein the oligonucleotide of SEQ NO:34 hybridizes to a complementary strand of SEQ NO:31, the oligonucleotide of any of SEQ NOs:35 to 40 hybridizes to a nucleic acid molecule of SEQ NO:32 and the oligonucleotide of SEQ NO:41 hybridizes to a nucleic acid molecule of SEQ NO:33. The primer (B) may also be an oligonucleotide indicated by any nucleotide sequence of SEQ NOs:34 to 41, wherein one or several base(s) thereof are deleted or substituted, or one or several base(s) are added thereto. It is preferable to use a combination of the primer of SEQ NO:34 and at least one primer selected from the group consisting of SEQ NOs:35 to 41.

In order to design these primers and to evaluate the designed primers, a PCR simulation may be used.

For example, in order to design the primer for detecting the genus *Fagopyrum,* a common region having a high specificity for all of the 21 DNA sequences of plants in genus *Fagopyrum* including eatable buckwheat (common buckwheat and Tartarian buckwheat) is selected from the region of ITS-1~5.8S rRNA gene~ITS-2 sequence, and further, a base, which can assure the specificity to other plants, is selected as 3' end of the primer to determine the primer sequence. However, the species in the genus *Fagopyrum* have the ITS-1~5.8S rRNA gene~ITS-2 sequence from which a part thereof is deleted and from which a number of bases are deleted, which differ from each other, and therefore, it is necessary to conduct further selection in order to obtain a same size of amplification product for the 21 plants in the genus *Fagopyrum*. If the same size of amplification product can be obtained for the 21 plants in the genus *Fagopyrum,* the presence of the genus *Fagopyrum* can be easily detected. In the genus *Fagopyrum,* particularly by selecting the primer (A) and the primer (C) or two primers (A), the simulation has confirmed that the same size of amplification product would be obtained for all of 21 plants in the genus *Fagopyrum.* There can be designed primers by which nonspecific products can be easily identified in light of the size of the products.

As mentioned above, regarding the designed primer, it was confirmed by PCR simulation whether or not the target amplification product could be obtained and the results were almost the same as the results of actual PCR, and therefore, the simulation results possess high reliability. In this connection, the above described PCR simulation software, Amplify 1.0 (Bill Engels) and the like can be used in the PCR simulation.

An amplification of DNA sequence using the primers described above can be conducted by PCR methods (Polymerase Chain Reaction: for example, Saiki R K, et al., Science, 230: 1350–1354(1985)), as well as LAMP (Loop-Mediated Isothermal Amplification: Notomi T, et al., Nucleic Acids Res., 28: e 63(2000)) or by other appropriate methods. In addition, though the amplification product is generally detected by electrophoresis, other methods can be used.

EXAMPLES

The present invention will be described more specifically with reference to the following Examples.

Example 1

A. Design of Oligonucleotide Primers for Detection of DNA from Buckwheat

1) DNA Sequences of the Genus *Fagopyrum*

Regarding the genus *Fagopyrum,* 5.8S rRNA gene, ITS-1 and ITS-2 sequences in the following 21 DNA sequences registered in GenBank were examined to select suitable regions for the primers.

1: *Fagopyrum urophyllum* (AB000342)
2: *Fagopyrum urophyllu* (AB000341)
3: Tartarian buckwheat: *Fagopyrum tataricuim* (sub_species: *potanini*) (AB000340)
4: Tartarian buckwheat: *Fagopyrum tataricum* (AB000339)
5: *Fagopyrum statice* (AB000338)
6: *Fagopyrum statice* (AB000337)
7: *Fagopyrum pleioramosum* (AB000336)
8: *Fagopyrum lineare* (AB000335)
9: *Fagopyrum leptopodum* (AB000334)
10: *Fagopyrum homotropicum* (AB00333)
11: *Fagopyrum gracilipes* (AB000332)

12: Common buckwheat: *Fagopyrum esclilentum ancestralis* (AB000331)
13: Common buckwheat: *Fagopyrum esculentum* (AB000330)
14: *Fagopyrum cymosum* (AB000329)
15: *Fagopyrum cymosum* (AB000328)
16: *Fagopyrum cymosum* (AB000327)
17: *Fagopyrum cymosum* (AB000326)
18: *Fagopyrum cymosum* (AB000325)
19: *Fagopyrum cymosum* (AB00324)
20: *Fagopyrum capillatum* (AB000323)
21: *Fagopyrum callianthum* (AB000322)

(2) DNA Sequences of other Common Allergenic Plants

As sequences of peanut, wheat, soybean, walnut, *matsutake* mushroom, peach, apple and orange, 5.8S rRNA gene, ITS-1 and ITS-2 sequences in the following DNA sequences registered in GenBank were selected.
1: peanut: *Arachis hypogaea* (AF156675)
2: wheat: *Triticum aestivum* (AJ301799)
3: soybean: *Glycine max* (U60551)
4: walnut: *Juglans regia* (AF303809)
5: *matsutake* mushroom: *Thicholoma matsutake* (U62964)
6: peach: *Prunus persica* (AF185621)
7: apple: *Malus x domestica* (AF186484)
8: Valencia orange: *Citrus* sp. (E08821)

(3) DNA Sequences of Plants Widely Used for a Food Ingredient

As sequences of corn, brown rice, pepper and mustard, 5.8S rRNA gene, ITS-1 and ITS-2 sequences in the following DNA sequences registered in GenBank were selected.
1: corn: *Zea mays* (U46648)
2: brown rice: *Oryza sativa* (AF169230)
3: pepper: *Piper nigrum* (AF275197)
4: mustard: *Sinapis alba* (X15915)

(4) Oligonucleotide Primer Synthesis and Evaluation

Among ITS-1 sequences of the aforementioned 21 DNA sequences of the genus *Fagopyrum,* there was determined a nucleotide sequence which would specifically hybridize to all of the 21 DNA sequences of the genus *Fagopyrum* through the study of the ITS-1 sequences. The thus determined nucleotide sequence is indicated as SEQ NO:11. Subsequently, the oligonucleotide primer with SEQ NO:11 was synthesized.

```
Sense primer
5'-GGA CCA CGA ACA GAA GCG CGT CCC G-3' (SEQ NO:11)
```

From among 5.8S rRNA gene sequences of the aforementioned 21 DNA sequences of the genus *Fagopyrum* and 8 DNA sequences of other common allergenic plants, there was determined a nucleotide sequence which would hybridize to all of these sequences through the study of the sequences. The thus determined nucleotide sequence is indicated as SEQ NO:3. Subsequently, the oligonucleotide primer with the SEQ NO:3 was synthesized.

```
        Antisense primer            (SEQ NO:3)
5'-ATC GCA TTT CGC TAC GTT CTT CAT CG-3'
```

Regarding the sense and antisense primer pair, the simulation was conducted with PCR simulation software, Amplify 1.0 (Bill Engels). As a result, it was predicted that target 140 bp amplification products would be obtained from the aforementioned 21 DNA sequences of the genus *Fagopyrum.* In contrast, no 140 bp amplification product was predicted from the aforementioned 8 DNA sequences of common allergenic plants other than genus *Fagopyrum* (peanut, wheat, soybean, walnut, *matsutake* mushroom, peach, apple and orange) and the 4 DNA sequences of plants widely used for a food ingredient (corn, brown rice, pepper and mustard). However, the results of the simulation indicated some possibility that nonspecific amplification products, which were different from the target one in size, would be obtained from soybean, apple and orange in light of weak amplified signals. On the other hand, no amplification product was predicted from the 5 DNA sequences of other common allergenic plants (peanut, wheat, walnut, *matsutake* mushroom and peach) and the 4 DNA sequences of plants widely used for a food ingredient (corn, brown rice, pepper and mustard). The simulation results are shown in Tables 1A and 1B. The meanings of symbols and numerical values in Tables 1A and 1B are explained below.

★: An obtained amplification product whose size almost matched to the target product size 140 bp (±10 bp), which would be obtained.

W 2–6: Probability of obtaining amplification products
High Probability - - - W6>W5>W4>W3>W2 - - - Low Probability Numerical values followed by bp:
Each value was obtained by subtracting 2 from the value obtained in the simulation.

(−): No amplification product was predicted.

TABLE 1A

| SEQ NO:11 & SEQ NO:3 primer: Amplification products | | | | | | |
|---|---|---|---|---|---|---|
| Scientific Name (Common Name) Genus *Fagopyrum* | GenBank Accession No. | W6 | W5 | W4 | W3 | W2 |
| ★*Fagopyrum urophyllum* | AB000342 | 140 bp | — | — | — | — |
| ★*Fagopyrum urophyllum* | AB000341 | 140 bp | — | — | — | — |
| ★*Fagopyrum tataricum* (Tartarian buckwheat) | AB000340 | 140 bp | — | 64 bp | — | — |
| ★*Fagopyrum tataricum* (Tartarian buckwheat) | AB000339 | 140 bp | — | 64 bp | — | — |
| ★*Fagopyrum statice* | AB000338 | 140 bp | — | — | — | — |
| ★*Fagopyrum statice* | AB000337 | 140 bp | — | — | — | — |
| ★*Fagopyrum pleioramosum* | AB000336 | 140 bp | — | — | — | — |
| ★*Fagopyrum lineare* | AB000335 | 140 bp | — | — | — | — |
| ★*Fagopyrum leptopodum* | AB000334 | 140 bp | — | — | — | — |
| ★*Fagopyrum homotropicum* | AB000333 | 140 bp | — | 326 bp | — | — |
| ★*Fagopyrum gracilipes* | AB000332 | 140 bp | — | — | — | — |
| ★*Fagopyrum esculentum* (Common buckwheat) | AB000331 | 140 bp | — | 326 bp | — | — |
| ★*Fagopyrum esculentum* (Common buckwheat) | AB000330 | 140 bp | — | 325 bp | — | — |
| ★*Fagopyrum cymosum* | AB000329 | 140 bp | — | — | 333 bp | — |
| ★*Fagopyrum cymosum* | AB000328 | 140 bp | — | — | 321 bp | — |
| ★*Fagopyrum cymosum* | AB000327 | 140 bp | — | — | 321 bp | — |
| ★*Fagopyrum cymosum* | AB000326 | 140 bp | — | — | — | — |
| ★*Fagopyrum cymosum* | AB000325 | 140 bp | — | — | 321 bp | — |
| ★*Fagopyrum cymosum* | AB000324 | 140 bp | — | — | 333 bp | — |
| ★*Fagopyrum capillatum* | AB000323 | 140 bp | — | — | — | — |
| ★*Fagopyrum callianthum* | AB000322 | 140 bp | — | — | — | — |

TABLE 1B

SEQ NO:11 & SEQ NO:3 primer: Amplification products

| Scientific Name (Common Name) | GenBank Accession No. | W6 | W5 | W4 | W3 | W2 |
|---|---|---|---|---|---|---|
| Other Common Allergenic Plants | | | | | | |
| Arachis hypogaea (Peanut) | AF156675 | — | — | — | — | — |
| Triticum aestivum (Wheat) | AJ301799 | — | — | — | — | — |
| Glycine max (Soybean) | U60551 | — | — | — | 227 bp | — |
| Juglans regia (Walnut) | AF303809 | — | — | — | — | — |
| Tricholoma matsutake (Matsutake mushroom) | U62964 | — | — | — | — | — |
| Prunus persica (Peach) | AF185621 | — | — | — | — | — |
| Malus x domestica (Apple) | AF186484 | — | — | 275 bp | — | — |
| Citrus sp. (Valencia orange) | E08821 | — | — | 312 bp 215 bp | — | — |
| Plants Widely Used for a Food Ingredient | | | | | | |
| Zea mays (Corn) | U46648 | — | — | — | — | — |
| Oryza sativa (Brown rice) | AF169230 | — | — | — | — | — |
| Piper nigrum (Pepper) | AF275197 | — | — | — | — | — |
| Sinapis alba (Mustard) | X15915 | — | — | — | — | — |

B. Preparation of Template DNA for PCR (1) Samples Used for DNA Isolation

Buckwheat:

Commercially available seeds of Shirahana soba (common buckwheat) and Dattan soba (Tartarian buckwheat) were used.

Buckwheat Chaff:

Commercially available buckwheat chaff used for pillows was used.

Pepper:

Commercially available seeds of black pepper and white pepper were used.

Soybean, Wheat, Corn and Mustard:

Leaves that germinated from commercially available seeds of soybean, wheat, corn and mustard were used.

Preparation of Black Pepper Powder Containing Buckwheat Chaff:

0.1 g of ground buckwheat chaff was added to 0.9 g of ground black pepper to obtain black pepper powder containing 10% buckwheat chaff.

(2) Isolation of DNA from Buckwheat, Buckwheat Chaff, Black Pepper, White Pepper and Black Pepper Powder Containing Buckwheat Chaff DNA isolation was conducted by using the QIAGEN Genomic-tip according to the procedures described in the Genomic DNA Handbook with a few modifications thereto as stated below.

Into a 15 ml-tube was transferred 1 g of a ground sample, added 4 ml of Carlson Lysis Buffer (0.1 M Tris-HCl (pH 9.5), 2% CTAB, 1.4 M Polyethylene Glycol# 6000, 20 mM EDTA), 8 μl of RNase A (100 mg/ml), 10 μl of 2-mercaptoethanol and 80 μl of proteinase K (20 mg/ml) thereto and mixed, and the resulting mixture was incubated for 20 min. at 74° C.

After cooling down to room temperature, to the mixture was added 5 ml of phenol/chloroform/isoamyl alcohol (25/24/1) at room temperature and mixed well by inverting the tube. After centrifuging them, a resulting upper water layer, was collected. The water layer was mixed well with the same volume of chloroform/isoamyl alcohol (24/1) and after centrifuging, a resulting upper water layer was collected. The water layer was mixed well with chloroform/isoamyl alcohol (24/1), and after centrifuging, a resulting water layer was collected again and used in the next step.

Half of the volume of the water layer obtained above was subjected to isopropanol precipitation to collect crude DNA. The collected crude DNA was dissolved in 500 μl of Buffer QBT and the resulting solution was applied to the Genomic-tip 20/G column equilibrated with 1 ml of Buffer QBT to adsorb DNA. Subsequently, the column was washed with 5 ml of Buffer QBT and then with 2 ml of Buffer QC. Finally, DNA was eluted with 1.7 ml of Buffer QF, and the resulting eluate was subjected to isopropanol precipitation to collect DNA, which was then dissolved in 40 μl of sterilized ultrapure water. After the concentration of the resulting DNA preparation was determined, the DNA preparation was used for a PCR template.

(3) Isolation of DNA from Leaves of Wheat, Soybean, Corn and Mustard

DNA isolation was conducted by using the QIAGEN DNeasy Plant Mini Kit according to the procedures described in the DNeasy Plant Mini Kit Handbook mentioned below.

0.5 g of a ground sample was transferred to a 15 ml-tube, added 3 ml of Buffer AP1 and 30 μl of RNase A (100 mg/ml), and mixed well with them. Then the resulting mixture was incubated for 15 min. at 65° C. 975 μl of Buffer AP2 was added to the mixture. The resulting mixture was incubated for 10 min. on ice and then centrifuged to obtain a supernatant. The supernatant was applied to a QIAshredder Spin Column and a flow-through fraction was obtained by centrifuging the column. To the flow-through fraction was added 0.5 volume of Buffer AP3 and 1 volume of ethanol, and mixed. The resulting mixture was divided into halves to be applied to two separate DNeasy Spin Columns. 650 μl of the mixture was applied to a DNeasy Spin Column and the column was centrifuged for 1 min. at 6,000×g to adsorb DNA. This step was repeated with the remaining mixture. In order to wash the column, to the column was added 500 μl of Buffer AW and was centrifuged for 1 min. at 6,000×g. To the column was added 500 μl of Buffer AW again and was centrifuged for 1 min. at a maximum speed to flush out the remaining Buffer AW. Finally, to the column was added 120 μl of preheated (65° C.) Buffer AE and was centrifuged for 1 min. at 6,000×g to obtain a DNA eluate. After the concentration thereof was determined, the DNA eluate was used for a PCR template.

(4) Preparation of DNA Solutions for Evaluation of Sensitivity (Buckwheat in Black Pepper Powder)

A DNA preparation derived from black pepper powder containing 10% buckwheat chaff was diluted stepwise with a DNA preparation from black pepper to obtain black pepper DNA solutions containing 1%, 0.1%, 100 ppm, 10 ppm, 1 ppm, 100 ppb, and 10 ppb of buckwheat chaff DNA. Both DNA preparations used above were obtained according to the procedures described in (2).

(5) Preparation of DNA Solutions for Evaluation of Sensitivity (Buckwheat in Wheat)

A DNA preparation derived from buckwheat seeds was diluted stepwise with a DNA preparation from wheat leaves to obtain wheat leaf DNA solutions containing 1 ppm, 100 ppb, 10 ppb, and 1 ppb of buckwheat seed DNA. The DNA preparation from buckwheat seeds was obtained according to the procedures described in (2). The DNA preparation from wheat leaves was obtained according to the procedures described in (3).

C. PCR

PCR was conducted using the QIAGEN HotStarTaq Master Mix Kit according to the procedures described in the HotStarTaq PCR Handbook as stated below.

Figure 2:
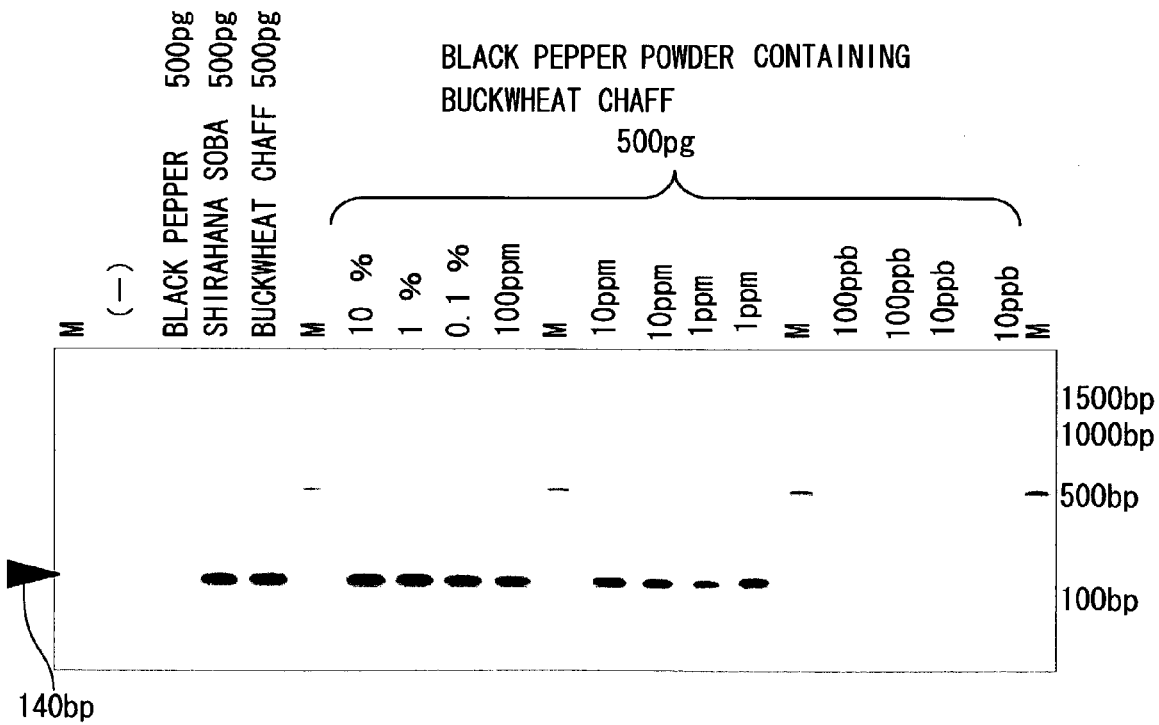
FIG. 2 is an electrophoretogram showing the results electrophoresed on a 2% agarose gel in Example 1.
Figure 3:
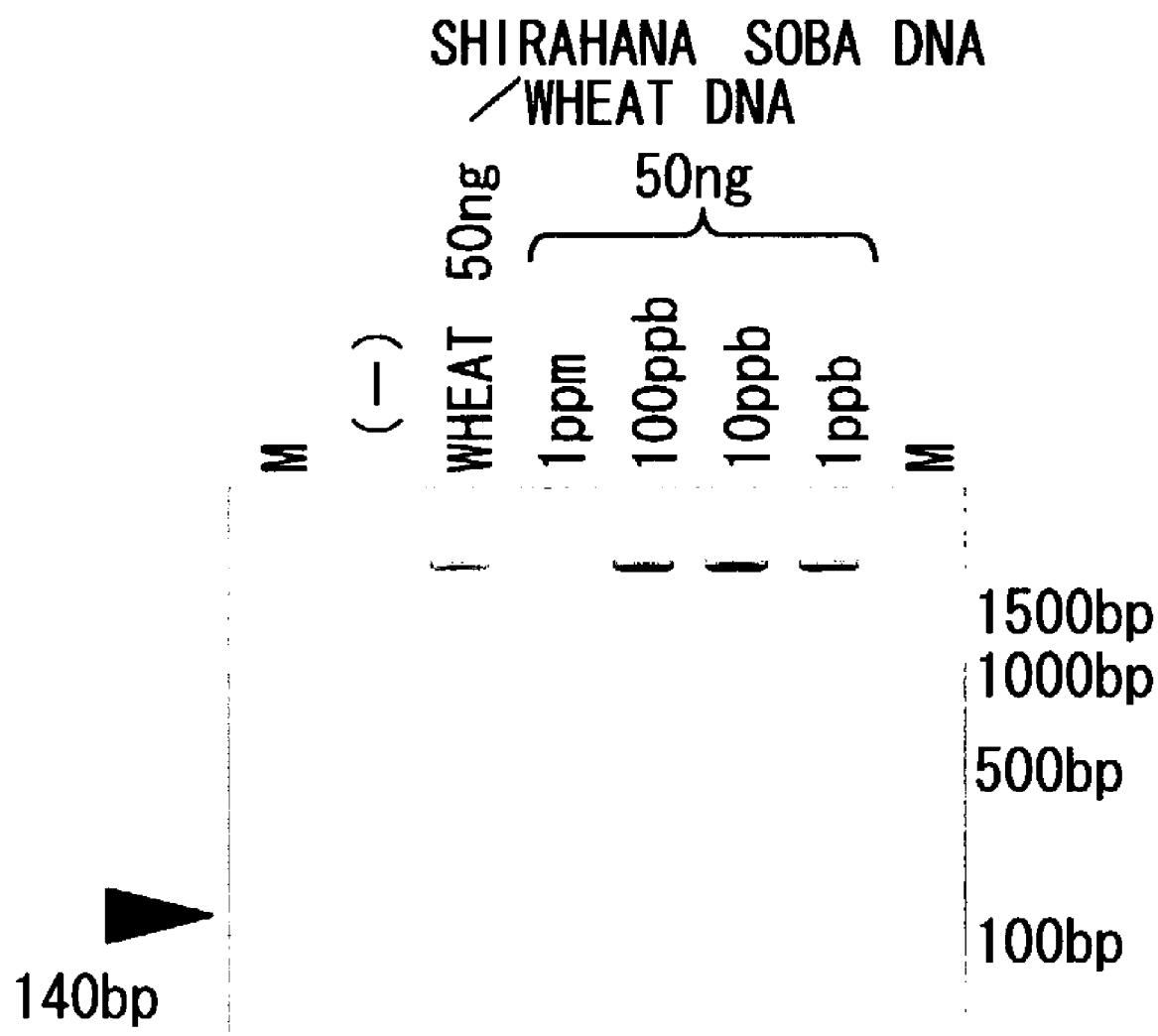
FIG. 3 is an electrophoretogram showing the results electrophoresed on a 2% agarose gel in Example 1.

PCR was carried out using final volumes of 25 µl of a solution containing 12.5 µl of 2× HotStarTaq Master Mix (HotStarTaq DNA Polymerase, PCR Buffer with 3 mM $MgCl_2$, 400 µM each dNTP), 0.2 µM of each primer (SEQ NO:11 and SEQ NO:3), the template DNA and sterilized ultrapure water in 0.2-ml microcentrifuge tubes. Amplification was performed using a GeneAmp PCR System 9600 (Applied Biosystems) according to the following PCR program: pre-incubation at 95° C. for 15 min.; 45 cycles consisting of denaturation at 95° C. for 1 min., annealing at 68° C. for 2 min. and extension at 72° C. for 1 min.; followed by a final extension at 72° C. for 4 min. The PCR reaction mixture was electrophoresed on a 2% agarose gel containing ethidium bromide. After the electrophoresis, the gel was analyzed using a FluorImager 595 (Amersham Pharmacia Biotech). The results are shown in FIGS. 1–3. The meanings of numerical values, abbreviations and symbols used in FIGS. 1–3 are as follows.

M: 100 bp DNA Ladder Marker
(−): Negative control (no DNA)
Numerical values above sample names: the amounts of the template DNA
Arrow: indicates the target amplification product (140 bp)

The quality of each of the template DNA used here was sufficient enough to be used for PCR based on the result of a separate PCR, in which target products were obtained using a primer pair to amplify a part of a plant chloroplast DNA.

D. PCR Results

PCR described above was conducted using primers designed in the present invention. The results are shown in FIGS. 1–3. As shown in FIG. 1, target 140 bp amplification products, predicted from the simulation results of the 21 DNA sequences of the genus *Fagopyrum*, were obtained from Shirahana soba (common buckwheat) and Dattan soba (Tartarian buckwheat). On the other hand, no 140 bp amplification product was obtained from wheat, mustard, soybean, corn, and white pepper. However, nonspecific amplification products whose sizes were different from the target product were obtained from soybean (approximately 230 bp) and wheat (approximately 2,300 bp) Because these results almost matched the simulation results shown in Table 1, the simulation results were thought to be reliable. Consequently, it was confirmed that a wide range of plants in the genus *Fagopyrum* including common buckwheat and Tartarian buckwheat were detectable using the present invention.

As shown in FIG. 2, target 140 bp amplification products, predicted from the simulation results of the 21 DNA sequences of the genus *Fagopyrum*, were obtained from black pepper powder samples containing 10 to 1 ppm of buckwheat chaff. This result showed that buckwheat chaff present in an amount of more than 1 ppm in black pepper is detectable.

As shown in FIG. 3, the target 140 bp amplification products, predicted from the simulation results of the 21 DNA sequences of the genus *Fagopyrum*, were obtained from the wheat DNA sample containing 10 to 1 ppm of buckwheat DNA.

The nonspecific amplification product that was obviously different from the target product in size did not interfere in the detection of 1 ppm of buckwheat DNA. This result showed that buckwheat DNA present in an amount of more than 1 ppm in wheat DNA is detectable.

E. Preparation of a Sequencing Sample (1) Purification of the Amplification Product from Buckwheat Chaff Purification of the amplification product from buckwheat chaff obtained in section D was conducted by using the QIAGEN QIAquick PCR Purification Kit according to the procedures described in the QIAquick Spin Handbook as stated below.

To 1 volume of PCR reaction mixture was added 5 volumes of Buffer PB and mixed well. After being spun down by centrifugation, to a QIAquick Spin Column was applied the mixture and centrifuged for 1 min. at 10,000×g to adsorb DNA. Then, to the column was added 750 µl of buffer PE to wash and centrifuged for 1 min. at 10,000×g. In addition, the column was centrifuged for 1 min. at 10,000×g to remove Buffer PE completely. Finally, to the column was added 50 µl of Buffer EB, let stand for 1 min., and then centrifuged for 1 min. at 10,000×g. The resulting eluted DNA was used for a sequencing sample.

(2) Sequencing PCR Reaction and Removal of Excess Dye-Labeled Dideoxynucleotides PCR for sequencing of the purified amplification product from buckwheat chaff obtained in (1) was conducted by using the Applied Biosystems BigDye Terminator Cycle Sequencing FS Ready Reaction Kit according to the procedures described in the manufacturer's manual as stated below.

The PCR for sequencing was carried out using final volumes of 20 µl of a solution containing 8 µl of BigDye Terminator RR Mix, 3.2 pmol of primer (SEQ NO:3), 2 ng template DNA and sterilized ultrapure water in 0.2-ml microcentrifuge tubes. Amplification was performed using a GeneAmp PCR System 9600 (Applied Biosystems) according to the following PCR program: pre-incubation at 96° C. for 1 min.; 25 cycles consisting of denaturation at 96° C. for 10 secs. and annealing and extension at 60° C. for 1 min.

Subsequently, removal of the excess dye-labeled dideoxynucleotides from the sequencing reaction mixture was conducted by using the Amersham Pharmacia Biotech AutoSeq G-50 according to the procedures described in the manufacturer's manual as stated below.

The AutoSeq G-50 column was uncapped and 100 µl of 10 mM EDTA was added to the resin in the column. The column was then capped and the resin inside was suspended thoroughly by vortexing. The cap was then loosened and the bottom closure of the column was snapped off. The column was then uncapped and placed in a 2-ml microcentrifuge tube for support and centrifuged for 1 min. at 2,000×g. The column was then placed in a new 2-ml microcentrifuge tube and the sample was applied to the resin in the column. After being capped, the column was centrifuged for 1 min. at 2,000×g, and the flow-through fraction obtained was used in the next step.

F. Sequence Analysis

The sample for sequencing from buckwheat chaff obtained in E (2) was analyzed using an ABI PRISM 310 Genetic Analyzer (Applied Biosystems). The obtained nucleotide sequence of the amplification product was compared with the sequence of common buckwheat, *Fagopyrum esculentum* (AB000330), registered in GenBank. The result is shown in FIG. 4. The meanings of number symbols above a nucleotide sequence, lines underneath this sequence and other symbols used in FIG. 4 are described below.

Number Symbols: Nucleotide numbers of amplification products
Asterisks (*): Identical nucleotides between two nucleotide sequences
Dash (-): Unidentifiable nucleotide
S: Mixed nucleotide with C and G
Single underline: The sense primer region
Double underline: The antisense primer region G. The Result of Sequence Analysis As shown in FIG. 4, the amplification product from buckwheat chaff obtained by PCR using the primers designed in the present invention almost matched the sequence of common buckwheat, *Fagopyrum esculentum* (AB000330). 87 out of 89 bases between two primer regions were determined in a sequence of the product and 86 of these bases matched the sequence of common buckwheat. If the base 44, determined as a mixture of two bases, is considered to match the sequence of common buckwheat, all 87 of these bases matched to the sequence of common buckwheat. This result indicates the target ITS-1~5.8S rRNA gene sequence of plants in the genus *Fagopyrum* can be detected without fail. Furthermore, the source of the buckwheat chaff, used in the aforementioned experiments, was traced back to common buckwheat (*Fagopyrum esculentum*).

Example 2

A. Design of Oligonucleotide Primers for Detection of DNA from Buckwheat (1) DNA Sequences of the Genus *Fagopyrum*, other Common Allergenic Plants and Plants Widely Used for a Food Ingredient The DNA sequences described in Example 1 (1) "DNA Sequences of the Genus *Fagopyrum*", (2) "DNA Sequences of Other Common Allergenic Plants" and (3) "DNA Sequences of Plants Widely Used for a Food Ingredient" were examined to select suitable regions for the primers.

(2) DNA Sequence of Related Species of the Genus *Fagopyrum*

As representatives of the DNA sequences of related species of the genus *Fagopyrum*, 5.8S rRNA gene, ITS-1 and ITS-2 sequences in the following 27 DNA sequences registered in GenBank were selected. In this connection, the 27 DNA sequences were selected as representatives of the DNA sequences of related species of the genus *Fagopyrum*, each of which had the highest score in the corresponding genus other than genus *Fagopyrum* and a score of 60 bits or more among sequences of species belonging to the corresponding genus selected from sequences registered in GenBank through a BLAST homology search using the ITS-1 sequence of buckwheat (*Fagopyrum esculentum* AB000330).

1: *Aconogonum* sp. Won 152 (AF189731)
2: *Fallopia scandens* (AF040069)
3: *Polygonum virginianum* (U51274)
4: *Rumex acetosella* (AF189730)
5: *Talinum paraguayense* (L78056)
6: *Bruinsmia styracoides* (AF396438)
7: *Talinella pachypoda* (L78054)
8: *Rehderodendron kwangtungense* (AF396448)
9: *Pterostyrax corymbosus* (AF396445)
10: *Anredera cordifolia* (L78086)
11: *Cistanthe quadripetala* (L78062)
12: *Xenia vulcanensis* (L78060)
13: *Talinopsis frutescens* (L78058)
14: *Talinaria palmeri* (L78052)
15: *Portulaca* sp. (L78049)
16: *Phenmeranthus confertiflorus* (L78039)
17: *Montiopsis unbellata* (L78033)
18: *Grahamia bracteata* (L78028)
19: *Herniaria glabra* (AJ310965)
20: *Alluaudia dumosa* (L78011)
21: *Sinojackia xylocarpa* (AF396451)
22: *Halesia macgregori* (AF396442)
23: *Changiostyrax dolichocarpa* (AF396439)
24: *Alectryon subdentatus* (AF314765)
25: *Anacampseros recurvata* (L78014)
26: *Weinmannia racemosa* (AF485597)
27: *Bursera tecomaca* (AF080029)

(3) Oligonucleotide Primer Synthesis and Evaluation

Among ITS-1 sequences of the aforementioned 21 DNA sequences of the genus *Fagopyrum*, there was determined a nucleotide sequence which would specifically hybridize to all of the 21 DNA sequences of the genus *Fagopyrum* and would not induce nonspecific amplification products from soybean through the study of the ITS-1 sequences. The thus determined nucleotide sequence is indicated as SEQ NO:14. Subsequently, the oligonucleotide primer with SEQ NO:14 was synthesized.

```
Sense primer
5'-CGC CAA GGA CCA CGA ACA GAA G-3'    (SEQ NO:14)
```

The oligonucleotide primer with SEQ NO:3 was also used as an antisense primer, the same as in Example 1.

Regarding the sense and antisense primer pair, the simulation was conducted with PCR simulation software, Amplify 1.0 (Bill Engels), which is the same as in Example 1. As a result, it was predicted that target 146 bp amplification products would be obtained from the aforementioned 21 DNA sequences of the genus *Fagopyrum*. In contrast, obtaining of any 146 bp amplification product was not predicted to be obtained from the aforementioned 8 DNA sequences of other common allergenic plants (peanut, wheat, soybean, walnut, *matsutake* mushroom, peach, apple and orange), the 4 DNA sequences of plants widely used as a food ingredient (corn, brown rice, pepper and mustard) and the 2 DNA sequences among related species of the genus *Fagopyrum* belonging to Polygonaceae and the 23 DNA sequences of related species of the genus *Fagopyrum* not belonging to Polygonaceae. In this connection, the results of simulation indicated some possibility that an amplification product, whose size almost matched the target product size of 146 bp, would be obtained from the sequences of *Aconogonum* sp. Won 152 and *Fallopia scandens* in the related species of the genus *Fagopyrum* belonging to Polygonaceae. However, by sequence analysis of the amplification products, it is possible to identify either the genus *Fagopyrum* or the related species thereof. The simulation results are shown in Tables 2A to 2C. The meanings of symbols and numerical values in Tables 2A to 2C are explained below.

*★: An obtained amplification product whose size almost matched the target product size 146 bp (±10 bp).

W 2–6: Probability of obtaining amplification products
High Probability - - - W6>W5>W4>W3>W2 - - - Low Probability Numerical values followed by bp:

Each value was obtained by subtracting 2 from the value obtained in the simulation.

(−): No amplification product was predicted.

Related Species of the Genus *Fagopyrum*:

Sequences similar to the ITS-1 sequence of *Fagopyrum esculentum* (AB000330) were searched by means of a BLAST homology search and the sequences having a score of 60 bits or more were selected from among them. Each sequence having the highest score in each genus and having a score of 60 bits or more is shown in the following Table 2C as the representative of the DNA sequences of related species of the genus *Fagopyrum*.

TABLE 2A

Buckwheat, SEQ NO:14 & SEQ NO:3 primer: Amplification products

| Scientific Name (Common Name) Genus *Fagopyrum* | GenBank Accession No. | W6 | W5 | W4 | W3 | W2 |
|---|---|---|---|---|---|---|
| ★*Fagopyrum urophyllum* | AB000342 | 146 bp | — | 439 bp | — | — |
| ★*Fagopyrum urophyllum* | AB000341 | 146 bp | — | — | — | — |
| ★*Fagopyrum tataricum* (Tartarian buckwheat) | AB000340 | 146 bp | — | — | — | — |
| ★*Fagopyrum tataricum* (Tartarian buckwheat) | AB000339 | 146 bp | — | — | — | — |
| ★*Fagopyrum statice* | AB000338 | 146 bp | — | — | — | — |
| ★*Fagopyrum statice* | AB000337 | 146 bp | — | — | — | — |
| ★*Fagopyrum pleioramosum* | AB000336 | 146 bp | — | — | — | — |
| ★*Fagopyrum lineare* | AB000335 | — | 146 bp | — | — | — |
| ★*Fagopyrum leptopodum* | AB000334 | 146 bp | — | — | — | — |
| ★*Fagopyrum homotropicum* | AB000333 | 146 bp | — | — | — | — |
| ★*Fagopyrum gracilipes* | AB000332 | 146 bp | — | — | — | — |
| ★*Fagopyrum esculentum* (Common buckwheat) | AB000331 | 146 bp | — | — | — | — |
| ★*Fagopyrum esculentum* (Common buckwheat) | AB000330 | 146 bp | — | — | — | — |
| ★*Fagopyrum cymosum* | AB000329 | 146 bp | — | — | — | — |
| ★*Fagopyrum cymosum* | AB000328 | 146 bp | — | — | — | — |
| ★*Fagopyrum cymosum* | AB000327 | 146 bp | — | — | — | — |
| ★*Fagopyrum cymosum* | AB000326 | 146 bp | — | — | — | — |
| ★*Fagopyrum cymosum* | AB000325 | 146 bp | — | — | — | — |
| ★*Fagopyrum cymosum* | AB000324 | 146 bp | — | — | — | — |
| ★*Fagopyrum capillatum* | AB000323 | 146 bp | — | — | — | — |
| ★*Fagopyrum callianthum* | AB000322 | 146 bp | — | 439 bp | — | — |

TABLE 2B

Buckwheat, SEQ NO:14 & SEQ NO:3 primer: Amplification products

| Scientific Name (Common Name) | GenBank Accession No. | W6 | W5 | W4 | W3 | W2 |
|---|---|---|---|---|---|---|
| Other Common Allergenic Plants | | | | | | |
| *Arachis hypogaea* (Peanut) | AF156675 | — | — | — | — | — |
| *Triticum aestivum* (Wheat) | AJ301799 | — | — | — | — | — |
| *Glycine max* (Soybean) | U60551 | — | — | — | — | — |
| *Juglans regia* (Walnut) | AF303809 | — | — | — | — | — |
| *Tricholoma matsutake* (Matsutake mushroom) | U62964 | — | — | — | — | — |
| *Prunus persica* (Peach) | AF185621 | — | — | — | — | — |
| *Malus* x *domestica* (Apple) | AF186484 | — | — | — | — | — |
| *Citrus* sp. (Valencia orange) | E08821 | — | — | — | — | — |
| Plants Widely Used for a Food Ingredient | | | | | | |
| *Zea mays* (Corn) | U46648 | — | — | — | — | — |
| *Oryza sativa* (Brown rice) | AF169230 | — | — | — | — | — |
| *Piper nigrum* (Pepper) | AF275197 | — | — | — | — | — |
| *Sinapis alba* (Mustard) | X15915 | — | — | — | — | — |

TABLE 2C

Buckwheat, SEQ NO:14 & SEQ NO:3 primer: Amplification products

| Scientific Name (Common Name) | GenBank Accession No. | W6 | W5 | W4 | W3 | W2 |
|---|---|---|---|---|---|---|
| Related Species of the Genus *Fagopyrum* Belonging to *Plygonaceae* | | | | | | |
| ★*Aconogonum* sp. Won 152 | AF189731 | — | 149 bp | — | — | — |
| ★*Fallopia scandens* | AF040069 | — | 145 bp | — | — | — |
| *Polygonum virginianum* | U51274 | — | — | — | — | — |
| *Rumex acetosella* | AF189730 | — | — | — | — | — |
| Related Species of the Genus *Fagopyrum* Not Belonging to *Polygonaceae* | | | | | | |
| *Talinum paraguayense* | L78056 | — | — | — | — | — |
| *Bruinsmia styracoides* | AF396438 | — | — | — | — | — |
| *Talinella pachypoda* | L78054 | — | — | — | — | — |
| *Rehderodendron kwangtungense* | AF396448 | — | — | — | — | — |
| *Pterostyrax corymbosus* | AF396445 | — | — | — | — | — |
| *Anredera cordifolia* | L78086 | — | — | — | — | — |
| *Cistanthe quadripetala* | L78062 | — | — | — | — | — |
| *Xenia vulcanensis* | L78060 | — | — | — | — | — |
| *Talinopsis frutescens* | L78058 | — | — | — | — | — |
| *Talinaria palmeri* | L78052 | — | — | — | — | — |
| *Portulaca* sp. | L78049 | — | — | — | — | — |
| *Phemeranthus confertiflorus* | L78039 | — | — | — | — | — |
| *Montiopsis umbellata* | L78033 | — | — | — | — | — |
| *Grahamia bracteata* | L78028 | — | — | — | — | — |
| *Herniaria glabra* | AJ310965 | — | — | — | — | — |
| *Alluaudia dumosa* | L78011 | — | — | — | — | — |
| *Sinojackia xylocarpa* | AF396451 | — | — | — | — | — |
| *Halesia macgregori* | AF396442 | — | — | — | — | — |
| *Changiostyrax dolichocarpa* | AF396439 | — | — | — | — | — |
| *Alectryon subdentatus* | AF314765 | — | — | — | — | — |

TABLE 2C-continued

Buckwheat, SEQ NO:14 & SEQ NO:3 primer: Amplification products

| Scientific Name (Common Name) | GenBank Accession No. | W6 | W5 | W4 | W3 | W2 |
|---|---|---|---|---|---|---|
| Anacampseros recurvata | L78014 | — | — | — | — | — |
| Weinmannia racemosa | AF485597 | — | — | — | — | — |
| Bursera tecomaca | AF080029 | — | — | — | — | — |

B. Preparation of Template DNA for PCR

The DNA samples isolated from buckwheat, pepper, wheat, soybean, corn and mustard in Examples 1 B (2) and (3) and the DNA solutions for evaluation of sensitivity prepared in Example 1 B (5) were used.

C. PCR

PCR was conducted in the same way as in Example 1 C, except for the use of the following primer and PCR program.

Primer:

Each primer of SEQ NO:14 and SEQ NO:3 was used at 0.2 µM of final concentration.

PCR Program:

PCR was conducted according to the following PCR program.

Pre-incubation at 95° C. for 15 min.; thereafter 45 cycles consisting of denaturation at 95° C. for 1 min., annealing at 66° C. for 2 min. and extension at 72° C. for 1 min.; followed by a final extension at 72° C. for 4 min.

Figure 5:
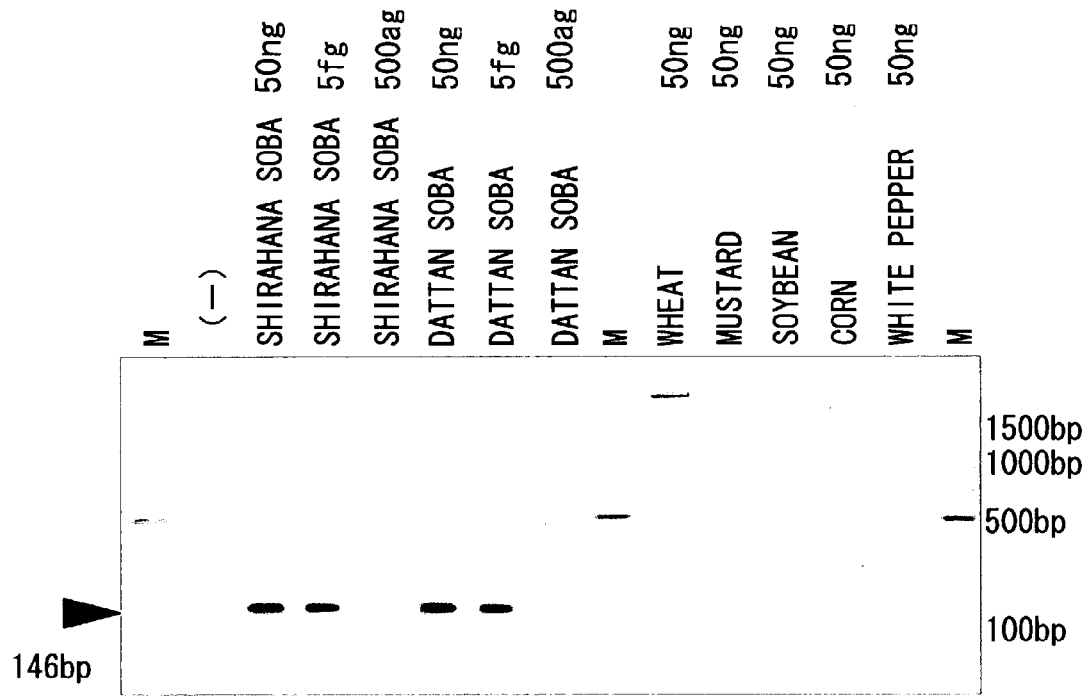
FIG. 5 is an electrophoretogram showing the results electrophoresed on a 2% agarose gel in Example 3.
Figure 6:
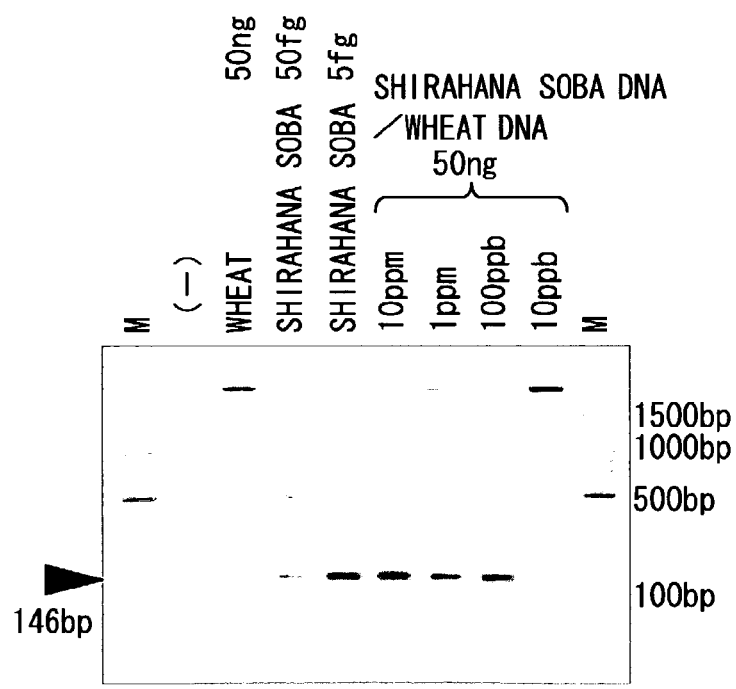
FIG. 6 is an electrophoretogram showing the results electrophoresed on a 2% agarose gel in Example 3.

The results are shown in FIGS. 5 and 6. The meanings of numerical values, abbreviations and synmbols used in FIGS. 5 and 6 are as follows.

M: 100 bp DNA Ladder Marker (−): Negative control (no DNA)

Numerical values above sample names: the amounts of the template DNA

Arrow: indicating the target amplification product (146 bp)

The quality of each of the template DNAs used here was sufficient enough to be used for PCR based on the result of a separate PCR, in which target products were obtained using a primer pair to amplify a part of plant chloroplast DNA.

D. PCR Results

PCR described above was conducted using primers designed in the present invention. The results are shown in FIGS. 5 and 6. As shown in FIG. 5, target 146 bp amplification products, predicted from the simulation results of the 21 DNA sequences of the genus *Fagopyrum*, were obtained from Shirahana soba (common buckwheat) and Dattan soba (Tartarian buckwheat). On the other hand, no 146 bp amplification product was obtained from wheat, mustard, soybean, corn, and white pepper (nonspecific amplification obtained from soybean in Example 1 was not obtained either). Likewise, no 146 bp amplification product was obtained from brown rice (not shown in FIG. 5). However, nonspecific amplification products whose sizes were different from that of the target product were obtained from wheat (approximately 2,300 bp). Because these results almost matched the simulation results shown in Table 2, the simulation results were thought to be reliable. Consequently, it was confirmed that a wide range of plants in the genus *Fagopyrum* including shirahana soba (common buckwheat) and Tartarian buckwheat were detectable using the present invention.

As shown in FIG. 6, the target 140 bp amplification product, predicted from the simulation results of the 21 DNA sequences of the genus *Fagopyrum*, was obtained from the wheat DNA sample containing 10 to 1 ppm of buckwheat DNA.

The nonspecific amplification product that was obviously different from the target in size did not interfere in the detection of 1 ppm of buckwheat DNA. This result showed that buckwheat DNA present in an amount of more than 1 ppm in wheat DNA is detectable.

E. Preparation of a Sequencing Sample (1) Purification of the Amplification Product from Shirahana Soba (Common Buckwheat)

Purification of the amplification product from Shirahana soba (common buckwheat) obtained in D was conducted in the same way as in Example 1 E (1) "Purification of the Amplification Product from Buckwheat Chaff".

(2) Sequencing PCR Reaction and Removal of Excess Dye-Labeled Dideoxynucleotides PCR for sequencing of the purified amplification product from Shirahana soba (common buckwheat) obtained in (1) was conducted in the same way as in Example 1 E (2) "Sequencing PCR Reaction and Removal of Excess Dye-Labeled Dideoxynucleotides", except for the use of primers of SEQ NO:14 and SEQ NO:3).

F. Sequence Analysis

Figure 7:
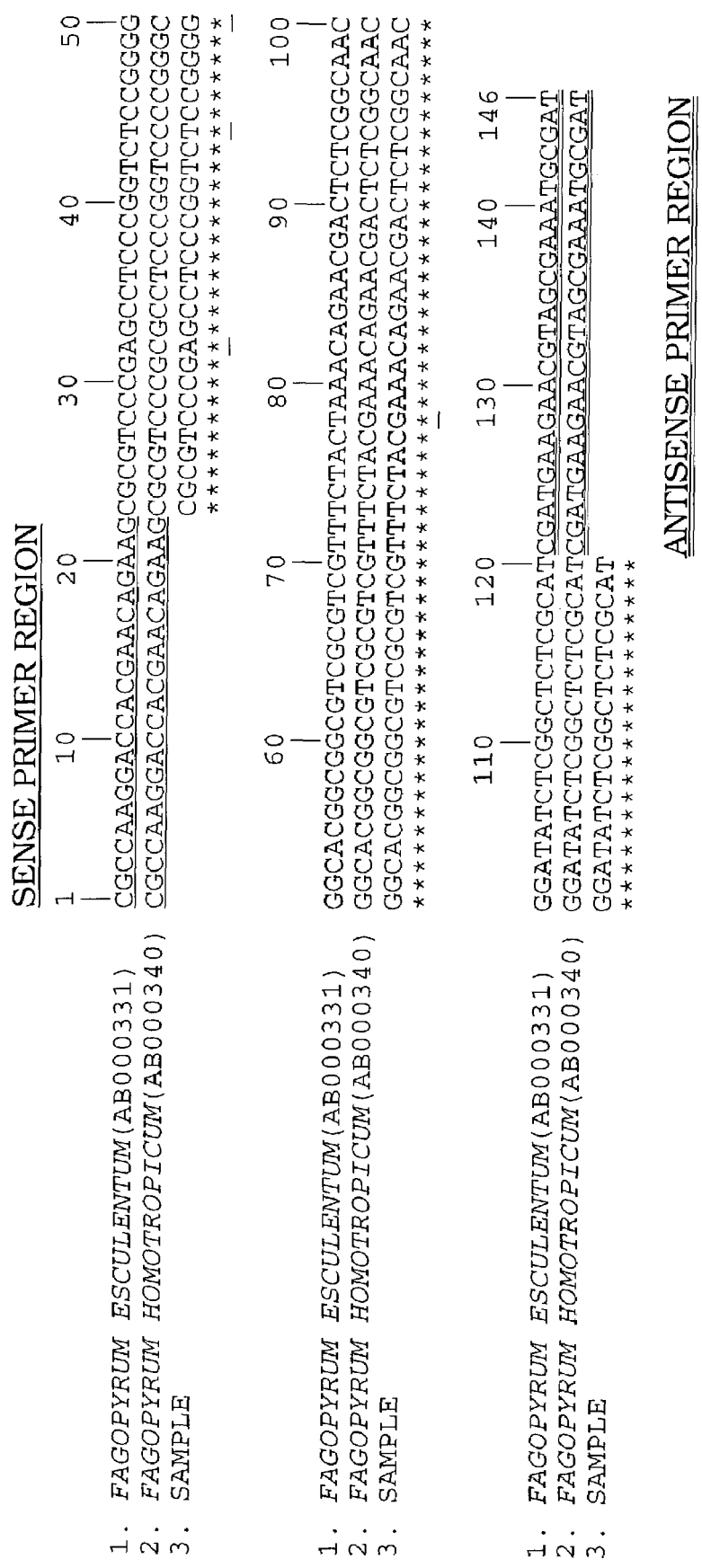
FIG. 7 is nucleotide sequences obtained by a sequence analysis of the target amplification product from Shirahana soba.

The sample for sequencing from Shirahana soba (common buckwheat) obtained in E (2) was analyzed using an ABI PRISM 310 Genetic Analyzer (Applied Biosystems). The obtained nucleotide sequence of the amplification product was compared with the sequence of common buckwheat, *Fagopyrum esculentum* (AB000331) and *F. homotropicum* (AB000340) in GenBank. The result is shown in FIG. 7. The meanings of number symbols above a nucleotide sequence, lines underneath this sequence and other symbols used in FIG. 7 are described below.

Number Symbols: Nucleotide numbers of amplification products

Asterisks (*): Nucleotides of Shirahana soba (common buckwheat), which are identical with those of both nucleotide sequences of *F. esculentum* (AB000331) and *F. homotropicum* (AB000340)

*: Nucleotides of Shirahana soba (common buckwheat), which are identical with those of only one of the nucleotide sequences of *F. escelentum* (AB000331) and *F. homotropicum* (AB000340)

Single underline: The sense primer region

Double underline: The antisense primer region

G. The result of Sequence Analysis

As shown in FIG. 7, all 89 bases between two primer regions in the amplification product derived from Shirahana soba (common buckwheat) by PCR using the primers designed in the present invention are completely identical with one of sequences of common buckwheat, *F. esculentum* (AB000331) or *F. homotropicum* (AB000340). This result indicates the target ITS-1~5.8S rRNA gene sequence of plants in the genus *Fagopyrum* can be detected without fail. Furthermore, the source of the Shirahana soba (common buckwheat), used in the aforementioned experiments, was traced back to *Fagopyrum esculentum* or *F. homotropicum*.

Example 3

A. Design of Oligonucleotide Primers for Detection of DNA from Peanut (1) DNA Sequences of the Genus *Arachis*

Regarding the genus *Arachis*, 5.8S rRNA gene, ITS-1 and ITS-2 sequences in the following 11 DNA sequences registered in GenBank were examined to select suitable regions for the primers.

1: *Arachis batizocoi* (AF203553)
2: *Arachis correntina* (AF203554)
3: *Arachis hermannii* (AF203556)
4: *Arachis hoehnei* (AJ320395)
5: *Arachis hypogaea* (AF156675)
6: *Arachis niagna* (AF203555)
7: *Arachis major* (AF203552)
8: *Arachis palustris* (AF203557)
9: *Arachis pintoi* (AF203551)
10: *Arachis triseminata* (AF204233)
11: *Arachis villosa* (AF203558)

(2) DNA Sequences of other Common Allergenic Plants

The DNA sequences described in Example 1 A (2) "DNA Sequences of Other Common Allergenic Plants" were selected. Regarding buckwheat, 5.8S rRNA gene, ITS-1 and ITS-2 sequences in the following DNA sequence registered in GenBank were also selected.

1: buckwheat: *Fagopyrum esculentum* (AB000330)

(3) DNA Sequences of Plants Widely Used for a Food Ingredient

The DNA sequences described in Example 1 A (3) "DNA Sequences of Plants Widely Used for a Food Ingredient" were selected.

(4) DNA Sequences of Leguminous Plants Widely Used for a Food Ingredient

Regarding French bean, lima bean, lentil, chickpea, mung bean and adzuki bean, 5.8S rRNA gene, ITS-1 and ITS-2 sequences in the following DNA sequences registered in GenBank were selected. In the case of adzuki bean, only the ITS-1 sequence of *Vigna angularis* var. *nipponensis* (AB059747) was selected because the 5.8S rRNA gene sequence was not registered in GenBank.

1: French bean: *Phaseolus vulgaris* (AF115169)
2: lima bean: *Phaseolus lunatus* (AF115175)
3: lentil: *Lens culinaris* subsp. *culinaris* (AF228066)
4: chickpea: *Cicer arietinum* (AJ237698)
5: mung bean: *Vigna radiata* (X14337)
6: adzuki bean: *Vigna angularis* var. *nipponensis* (AB059747)

(5) DNA Sequences of Plants in Related Species of the Genus *Arachis*

As representatives of the DNA sequences of related species of the genus *Arachis*, 5.8S rRNA gene, ITS-1 and ITS-2 sequences in the following 69 DNA sequences registered in GenBank were selected. In this connection, the 69 DNA sequences were selected as representatives of the DNA sequence of related species of the genus *Arachis*, each of which had the highest score in the corresponding genus other than genus *Arachis* and a score of 60 bits or more among sequences of species belonging to the corresponding genus selected from ITS-1 sequence of buckwheat through BLAST homology search. (*Arachis hypogaea* AF156675)

1: *Stylosanthes acuminata* (AJ320282)
2: *Stylosanthes angustifolia* (AJ320284)
3: *Stylosanthes aurea* (AJ320285)
4: *Stylosanthes biflora* (AJ320289)
5: *Stylosanthes bracteata* (AJ320346)
6: *Stylosanthes calcicola* (AJ320348)
7: *Stylosanthes campestris* (AJ32029 1)
8: *Stylosanthes capitata* (AJ320350)
9: *Stylosanthes cayennensis* (AJ320292)
10: *Stylosanthes erecta* (AJ320352)
11: *Stylosanthes friticosa* (AJ320356)
12: *Stylosanthes gracilis* (AJ320296)
13: *Stylosanthes grandifolia* (AJ320299)
14: *Stylosanthes guianensis* subsp. *dissitiflora* (AJ320301)
15: *Stylosanthes hamata* (AJ320365)
16: *Stylosanthes hippocampoides* (AJ320317)
17: *Stylosanthes hispida* (AJ320328)
18: *Stylosanthes humilis* (AJ320323)
19: *Stylosanthes ingrata* (AJ320329)
20: *Stylosanthes leiocarpa* (AJ320332)
21: *Stylosanthes linearifolia* (AJ320367)
22: *Stylosanthes macrocarpa* (AJ320369)
23: *Stylosanthes macrocephala* (AJ320371)
24: *Stylosanthes macrosoma* (AJ320333)
25: *Stylosanthes mexicana* (AJ320374)
26: *Stylosanthes montevidensis* (AJ320336)
27: *Stylosanthes pilosa* (AJ320377)
28: *Stylosanthes scahra* (AJ320382)
29: *Stylosanthes seahrana* (AJ320384)
30: *Stylosanthes sericeiceps* (AJ320386)
31: *Stylosanthes subsericea* (AJ320387)
32: *Stylosanthes sundaica* (AJ320389)
33: *Stylosanthes synmpodialis* (AJ320391)
34: *Stylosanthes tonmentosa* (AJ320337)
35: *Stylosanthes tuherculata* (AJ320392)
36: *Stylosanthes viscosa* (AJ320340)
37: *Ormocarpum bernierianum* (AF189036)
38: *Ormocarpum coeruleum* (AF189037)
39: *Ormocarpum drakei* (AF189039)
40: *Ormocarpum flavum* (AF189041)
41: *Ormocarpum keniense* (AF068155)
42: *Ormocarpum kirkii* (AF068152)
43: *Ormocarpum klainei* (AF 189044)
44: *Ormocarpum megalophyllum* (AF068154)
45: *Ormocarpum muricatum* (AF068156)
46: *Ormocarpum orientale* (AF068159)
47: *Ormocarpum pubescens* (AF189045)
48: *Ormocarpum rectangulare* (AF189046)
49: *Ormocarpum schliebenii* (AF189047)
50: *Ormocarpum sennoides* (AF068153)
51: *Ormocarpum somalense* (AF189048)
52: *Ormocarpum trachycarpum* (AF189049)
53: *Ormocarpum trichocarpum* (AF068158)
54: *Ormocarpum verrucosum* (AF189050)
55: *Chapmannia floridana* (AF203543)
56: *Chapmannia prisniatica* (AJ320400)
57: *Chapmannia sonialensis* (AF203544)
58: *Ormocarpopsis aspera* (AF068148)
59: *Ormocarpopsis calcicola* (AF068145)
60: *Ormocarpopsis itrenmoensis* (AF068149)
61: *Ormocarpopsis mandrarensis* (AF068147)
62: *Ormocarpopsis parvifolia* (AF068144)
63: *Ormocarpopsis tulearensis* (AF068146)
64: *Diphysa humilis* (AF068162)
65: *Diphysa nmacrophylla* (AF189029)
66: *Diphysa suberosa* (AF189034)
67: *Spigelia coelostylioides* (AF177992)
68: *Spigelia hedyotidea* (AF178005)
69: *Spigelia marilandica* (AF177991)

(6) Oligonucleotide Primer Synthesis and Evaluation

Among ITS-1 sequences of the aforementioned 11 DNA sequences of the genus *Arachis*, there was determined three nucleotide sequences which would specifically hybridize to all of the 11 DNA sequences of the genus *Arachis* through the study of the ITS-1 sequences. The thus determined nucleotide sequences are indicated as SEQ NOs:18, 19 and 20. Subsequently, the oligonucleotide primers with SEQ NOs:18, 19 and 20 were synthesized.

```
Sense primers
5'-GCG GAA AGC GCC AAG GAA GC-3'    (SEQ NO:18)

5'-CGG CTT CCG GAG ACG GCA-3'       (SEQ NO:19)

5'-CGG CTC CGG AGA CGG CA-3'        (SEQ NO:20)
```

As an antisense primer, the oligonucleotide primer with SEQ NO:3 was also used, the same as in Example 1.

Regarding the sense and antisense primer pairs, a simulation was conducted with PCR simulation software, Amplify 1.0 (Bill Engels), in the same manner as in Example 1. As a result, it was predicted that 156 to 157 bp (a combination of the primers with SEQ NOs:18 and 3), 114 to 116 bp (a combination of the primers with SEQ NOs:19 and 3) and 113 to 115 bp (a combination of the primers with SEQ NOs:20 and 3) of target amplification products would be obtained from the aforementioned 11 DNA sequences of the genus *Arachis*.

Furthermore, regarding the sense and antisense primer pairs, it was predicted whether amplification products would be obtained from the aforementioned 8 DNA sequences of common allergenic plants other than peanut (buckwheat, wheat, soybean, walnut, *matsutake* mushroom, peach, apple and orange), the 4 DNA sequences of plants widely used as a food ingredient (corn, rise, pepper and mustard) and the 6 DNA sequences of leguminous plants widely used for a food ingredient (French bean, lima bean, lentil, chickpea, mung bean and adzuki bean).

Regarding the combination of the primers with SEQ NOs:18 and 3, the result of a simulation indicated that desired amplification products having almost 156 bp would not be obtained from 7 DNA sequences of common allergenic plants other than peanut (buckwheat, wheat, soybean, walnut, *matsutake* mushroom, peach and orange), the 4 DNA sequences of plants widely used as a food ingredient (corn, brown rice, pepper and mustard) and the 6 DNA sequences of leguminous plants widely used for a food ingredient (French bean, lima bean, lentil, chickpea, mung bean and adzuki bean). In this connection, the results of the simulation indicated some possibility that amplification products having almost 156 bp would be obtained from apple from among the other common allergenic plants. However, by a sequence analysis of the amplification products, it is possible to identify either peanut or apple. The simulation results are shown in Tables 3A and 3B. The meanings of symbols and numerical values in Tables 3A and 3B are explained below.

★: An obtained amplification product whose size almost matched the target product size 156 bp (±10 bp).

W 2–6: Probability of obtaining amplification products

High Probability - - - W6>W5>W4>W3>W2 - - - Low Probability Numerical values followed by bp:

Each value was obtained by subtracting 2 from the value obtained in the simulation.

(–): No amplification product was predicted.

(–*): No annealing site of the primer (SEQ NO: 18) was predicted within the ITS-1 sequence of *Vigna angularis* var. *nipponensis* (adzuki bean).

In the case of adzuki bean, only the ITS-1 sequence was selected because the 5.8S rRNA gene sequence of *Vigna angularis* var. *nipponensis* (AB059747) was not registered in GenBank.

TABLE 3A

Peanut, SEQ NO:18 & SEQ NO:3 primer: Amplification products

| Scientific Name (Common Name) | GenBank Accession No. | W6 | W5 | W4 | W3 | W2 |
|---|---|---|---|---|---|---|
| Genus *Arachis* | | | | | | |
| ★*Arachis batizocoi* | AF203553 | 156 bp | — | — | — | — |
| ★*Arachis correntina* | AF203554 | 156 bp | — | — | — | — |
| ★*Arachis hermannii* | AF203556 | 156 bp | — | — | — | — |
| ★*Arachis hoehnei* | AJ320395 | 156 bp | — | — | — | — |
| ★*Arachis hypogaea* (Peanut) | AF156675 | 156 bp | — | — | — | — |
| ★*Arachis magna* | AF203555 | 156 bp | — | — | — | — |
| ★*Arachis major* | AF203552 | 156 bp | — | — | — | — |
| ★*Arachis palustris* | AF203557 | 156 bp | — | — | — | — |
| ★*Arachis pintoi* | AF203551 | 157 bp | — | — | — | — |
| ★*Arachis triseminata* | AF204233 | 156 bp | — | — | — | — |
| ★*Arachis villosa* | AF203558 | 156 bp | — | — | — | — |
| Other Common Allergenic Plants | | | | | | |
| *Fagopyrum esculentum* (Common buckwheat) | AB000330 | — | — | — | — | — |
| *Triticum aestivum* (Wheat) | AJ301799 | — | — | — | — | — |
| *Glycine max* (Soybean) | U60551 | — | — | — | — | — |
| *Juglans regia* (Walnut) | AF303809 | — | — | — | — | — |
| *Tricholoma matsutake* (Matsutake mushroom) | U62964 | — | — | — | — | — |
| *Prunus persica* (Peach) | AF185621 | — | — | — | — | — |
| ★*Malus* x *domestica* (Apple) | AF186484 | — | 155 bp | — | 424 bp 467 bp | — |
| *Citrus* sp. (Valencia orange) | E08821 | — | — | — | — | — |

TABLE 3B

Peanut, SEQ No:18 & SEQ No:3 primer: Amplification products

| Scientific Name (Common Name) | GenBank Accession No. | W6 | W5 | W4 | W3 | W2 |
|---|---|---|---|---|---|---|
| Plants Widely Used for a Food Ingredient | | | | | | |
| *Zea mays* (Corn) | U46648 | — | — | — | — | — |
| *Oryza sativa* (Brown rice) | AF169230 | — | — | — | — | — |

TABLE 3B-continued

Peanut, SEQ No:18 & SEQ No:3 primer: Amplification products

| Scientific Name (Common Name) | GenBank Accession No. | W6 | W5 | W4 | W3 | W2 |
|---|---|---|---|---|---|---|
| *Piper nigrum* (Pepper) | AF275197 | — | — | — | — | — |
| *Sinapis alba* (Mustard) | X15915 | — | — | — | — | — |
| Leguminous Plants Widely Used for a Food Ingredient | | | | | | |
| *Phaseolus vulgaris* (French bean) | AF115169 | — | — | — | — | — |
| *Phaseolus lunatus* (Lima bean) | AF115175 | — | — | — | — | — |
| *Lens culinaris* subsp. *culinaris* (Lentil) | AF228066 | — | — | — | — | — |
| *Cicer arietinum* (Chickpea) | AJ237698 | — | — | — | — | — |
| *Vigna radiata* (Mung bean) | X14337 | — | — | — | — | — |
| *Vigna angularis* var. *nipponensis* (Adzuki bean)* | AB059747 | | | —* | | |

Regarding the combination of the primers with SEQ NOs:20 and 3, no amplification product having almost 114 bp was predicted from 6 DNA sequences of common allergenic plants other than peanut (wheat, walnut, *matsutake* mushroom, peach, apple and orange), the 4 DNA sequences of plants widely used as a food ingredient (corn, brown rice, pepper and mustard) and the 5 out of 6 DNA sequences of leguminous plants widely used for a food ingredient (French bean, lima bean, lentil, chickpea and mung bean). In this connection, the results of the simulation indicated some possibility that nonspecific amplification products having almost 114 bp would be obtained from buckwheat and from soybean from among the other common allergenic plants and from adzuki bean in the leguminous plants widely used for a food ingredient in even weak amplified signals. Here, regarding the DNA sequence of adzuki bean (*Vigna angularis* var. nipponensis AB059747), as the ITS-1 sequence was registered in GenBank, but the 5.8S rRNA gene sequence was not registered therein, the amplification product having almost 100 bp was estimated based on the predicted annealing site of SEQ NO: 20 to the ITS-1 sequence and the assumption that *Vigna angularis* var. *nipponensis* (adzuki bean) had the same 5.8S rRNA gene sequence as *Arachis hypogaea* (peanut) and the primer with SEQ NO: 3 had an annealing site within the 5.8S rRNA gene sequence. However, despite the prediction of amplification, the probability of obtaining these amplification products compared with obtaining the target amplification product of the genus *Arachis* were lower than the probability of obtaining amplification for peanut, and by a sequence analysis of the amplification products, it is also possible to identify whether they are peanut or not.

In addition, regarding the combination of the primers with SEQ NOs:20 and 3, no amplification products having almost 100 bp were predicted from the 69 DNA sequences of related species of both the genus *Arachis* belonging to leguminous plants and those not belonging to leguminous plants. The simulation results are shown in Tables 4A to 4E. The meanings of symbols and numerical values in Tables 4A to 4E are explained below.

As to the simulation in which SEQ NO: 19 and SEQ NO: 3 were used, the result is not shown here because it was later found that this primer pair was not suitable for PCR analysis to detect the genus *Arachis*.

★: An obtained amplification product whose size almost matched the target 114 bp (±10 bp).

W 2–6: Probability of obtaining amplification products

High Probability - - - W6>W5>W4>W3>W2 - - - Low Probability Numerical values followed by bp:

Each value was obtained by subtracting 2 from the value obtained in the simulation.

(−): No amplification product was predicted.

Related Species of the Genus *Arachis*:

Sequences similar to the ITS-1 sequence of *Arachis hypogaea* (AF156675) were searched by means of a BLAST homology search and the sequences having a score of 60 bits or more were selected among them. Each sequence having highest score in each genus and having a score of 60 bits or more is shown in the following Tables 4D–4E as the representatives of the DNA sequences of related species of the genus *Arachis*.

(+*): An annealing site of the primer (SEQ NO: 20) was predicted within the ITS-1 of *Vigna angularis* var. *nipponensis* (adzuki bean).

In the case of adzuki bean, only the ITS-1 sequence registered in GenBank was used because the 5.8S rRNA gene sequence of *Vigna angtilaris* var. *nipponensis* (AB059747) was not registered in GenBank. Furthermore, the size of the amplification product (approximately 100 bp) was estimated based on the predicted annealing site of the SEQ NO: 20 within the ITS-1 sequence and the assumption described below. It was assumed that *Vigna angularis* var. *nipponensis* (adzuki bean) had the same 5.8S rRNA gene sequence as *Arachis hypogaea* (peanut) and the primer with the SEQ NO: 3 had an annealing site within the 5.8S rRNA gene sequence.

TABLE 4A

Peanut, SEQ NO:20 & SEQ NO:3 primer: Amplification products

| Scientific Name (Common Name) | GenBank Accession No. | W6 | W5 | W4 | W3 | W2 |
|---|---|---|---|---|---|---|
| Genus *Arachis* | | | | | | |
| ★*Arachis batizocoi* | AF203553 | 114 bp | — | 281 bp | — | 52 bp |
| ★*Arachis correntina* | AF203554 | 114 bp | — | 282 bp | — | — |
| ★*Arachis hermannii* | AF203556 | 114 bp | — | 281 bp | — | — |
| ★*Arachis hoehnei* | AJ320395 | 114 bp | — | 284 bp | — | — |
| ★*Arachis hypogaea* (Peanut) | AF156675 | — | 113 bp | 286 bp | — | — |
| ★*Arachis magna* | AF203555 | 114 bp | — | 282 bp | — | — |
| ★*Arachis major* | AF203552 | 114 bp | — | 281 bp | — | — |
| ★*Arachis palustris* | AF203557 | 114 bp | — | 282 bp | — | — |
| ★*Arachis pintoi* | AF203551 | 115 bp | — | 283 bp | — | — |
| ★*Arachis triseminata* | AF204233 | 114 bp | — | 281 bp | — | — |
| ★*Arachis villosa* | AF203558 | 114 bp | — | 283 bp | — | — |

TABLE 4A-continued

Peanut, SEQ NO:20 & SEQ NO:3 primer: Amplification products

| Scientific Name (Common Name) | GenBank Accession No. | W6 | W5 | W4 | W3 | W2 |
|---|---|---|---|---|---|---|
| Other Common Allergenic Plants | | | | | | |
| ★*Fagopyrum esculentum* (Common buckwheat) | AB000330 | — | — | 109 bp | — | — |
| *Triticum aestivum* (Wheat) | AJ301799 | — | — | 247 bp 154 bp | — | — |
| *Glycine max* (Soybean) | U60551 | — | — | 98 bp | — | — |
| *Juglans regia* (Walnut) | AF303809 | — | — | — | — | — |
| *Tricholoma matsutake* (Matsutake mushroom) | U62964 | — | — | — | — | — |
| *Prunus persica* (Peach) | AF185621 | — | — | — | — | — |
| *Malus* x *domestica* (Apple) | AF186484 | — | — | — | — | — |
| *Citrus* sp. (Valencia orange) | E08821 | — | — | — | — | — |

TABLE 4B

Peanut, SEQ NO:20 & SEQ NO:3 primer: Amplification products

| Scientific Name (Common Name) | GenBank Accession No. | W6 | W5 | W4 | W3 | W2 |
|---|---|---|---|---|---|---|
| Plants Widely Used for a Food Ingredient | | | | | | |
| *Zea mays* (Corn) | U46648 | — | — | — | — | — |
| *Oryza sativa* (Brown rice) | AF169230 | — | — | — | — | — |
| *Piper nigrum* (Pepper) | AF275197 | — | — | — | — | 80 bp |
| *Sinapis alba* (Mustard) | X15915 | — | — | — | — | — |
| Leguminous Plants Widely Used for a Food Ingredient | | | | | | |
| *Phaseolus vulgaris* (French bean) | AF115169 | — | — | — | — | — |
| *Phaseolus lunatus* (Lima bean) | AF115175 | — | — | — | — | — |
| *Lens culinaris* subsp. *Culinaris* (Lentil) | AF228066 | — | — | — | — | — |
| *Cicer arietinum* (Chickpea) | AJ237698 | — | — | — | — | — |
| *Vigna radiata* (Mung bean) | X14337 | — | — | — | — | — |
| ★*Vigna angularis* var. *nipponensis* (Adzuki bean)* | AB059747 | | +* (approximately 100 bp) | | | |

TABLE 4C

Peanut, SEQ NO:20 & SEQ NO:3 primer: Amplification products

| Scientific Name (Common Name) Related Species of the Genus *Arachis* Belonging to Leguminous Plants | GenBank Accession No. | W6 | W5 | W4 | W3 | W2 |
|---|---|---|---|---|---|---|
| *Stylosanthes acuminata* | AJ320282 | — | — | — | — | — |
| *Stylosanthes angustifolia* | AJ320284 | — | — | — | — | — |
| *Stylosanthes aurea* | AJ320285 | — | — | — | — | — |
| *Stylosanthes biflora* | AJ320289 | — | — | — | — | — |
| *Stylosanthes bracteata* | AJ320346 | — | — | — | — | — |
| *Stylosanthes calcicola* | AJ320348 | — | — | — | — | — |
| *Stylosanthes campestris* | AJ320291 | — | — | — | — | — |
| *Stylosanthes capitata* | AJ320350 | — | — | 217 bp | 351 bp 384 bp | — |
| *Stylosanthes cayennensis* | AJ320292 | — | — | — | — | — |
| *Stylosanthes erecta* | AJ320352 | — | — | — | — | — |
| *Stylosanthes fruticosa* | AJ320356 | — | — | — | — | — |
| *Stylosanthes gracilis* | AJ320296 | — | — | — | — | — |
| *Stylosanthes grandifolia* | AJ320299 | — | — | — | — | — |
| *Stylosanthes guianensis* subsp. *dissitiflora* | AJ320301 | — | — | — | — | — |
| *Stylosanthes hamata* | AJ320365 | — | — | — | — | — |
| *Stylosanthes hippocampoides* | AJ320317 | — | — | — | — | — |
| *Stylosanthes hispida* | AJ320328 | — | — | — | — | — |
| *Stylosanthes humilis* | AJ320323 | — | — | — | — | — |
| *Stylosanthes ingrata* | AJ320329 | — | — | — | — | — |
| *Stylosanthes leiocarpa* | AJ320332 | — | — | — | — | — |

TABLE 4D

Peanut, SEQ NO:20 & SEQ NO:3 primer: Amplification products

| Scientific Name (Common Name) Related Species of the Genus *Arachis* Belonging to Leguminous Plants | GenBank Accession No. | W6 | W5 | W4 | W3 | W2 |
|---|---|---|---|---|---|---|
| *Stylosanthes linearifolia* | AJ320367 | — | — | — | — | — |
| *Stylosanthes macrocarpa* | AJ320369 | — | — | — | — | — |
| *Stylosanthes macrocephala* | AJ320371 | — | — | 217 bp | 384 bp | — |
| *Stylosanthes macrosoma* | AJ320333 | — | — | — | — | — |
| *Stylosanthes mexicana* | AJ320374 | — | — | — | — | — |
| *Stylosanthes montevidensis* | AJ320336 | — | — | — | — | — |
| *Stylosanthes pilosa* | AJ320377 | — | — | — | — | — |
| *Stylosanthes scabra* | AJ320382 | — | — | — | — | — |
| *Stylosanthes seabrana* | AJ320384 | — | — | — | — | — |
| *Stylosanthes sericeiceps* | AJ320386 | — | — | — | — | — |
| *Stylosanthes subsericea* | AJ320387 | — | — | — | — | — |
| *Stylosanthes sundaica* | AJ320389 | — | — | — | — | — |
| *Stylosanthes sympodialis* | AJ320391 | — | — | — | — | — |
| *Stylosanthes tomentosa* | AJ320337 | — | — | — | — | — |
| *Stylosanthes tuberculata* | AJ320392 | — | — | — | — | — |
| *Stylosanthes viscosa* | AJ320340 | — | — | — | — | — |
| *Ormocarpum bernierianum* | AF189036 | — | — | — | — | — |
| *Ormocarpum coeruleum* | AF189037 | — | — | — | — | — |
| *Ormocarpum drakei* | AF189039 | — | — | — | — | — |
| *Ormocarpum flavum* | AF189041 | — | — | — | — | — |
| *Ormocarpum keniense* | AF068155 | — | — | — | 213 bp | — |
| *Ormocarpum kirkii* | AF068152 | — | — | — | — | — |
| *Ormocarpum klainei* | AF189044 | — | — | — | — | — |

TABLE 4E

Peanut, SEQ NO:18 & SEQ NO:3 primer: Amplification products

| Scientific Name (Common Name) | GenBank Accession No. | W6 | W5 | W4 | W3 | W2 |
|---|---|---|---|---|---|---|
| Related Species of the Genus *Arachis* Belonging to Leguminous Plants | | | | | | |
| *Ormocarpum megalophyllum* | AF068154 | — | — | — | — | — |
| *Ormocarpum muricatum* | AF068156 | — | — | 260 bp | — | — |
| *Ormocarpum orientale* | AF068159 | — | — | — | — | — |
| *Ormocarpum pubescens* | AF189045 | — | — | 215 bp | — | — |
| *Ormocarpum rectangulare* | AF189046 | — | — | — | — | — |
| *Ormocarpum schliebenii* | AF189047 | — | — | — | — | — |
| *Ormocarpum sennoides* | AF068153 | — | — | — | — | — |
| *Ormocarpum somalense* | AF189048 | — | — | — | — | — |
| *Ormocarpum trachycarpum* | AF189049 | — | — | 214 bp | — | — |
| *Ormocarpum trichocarpum* | AF068158 | — | — | — | — | — |
| *Ormocarpum verrucosum* | AF189050 | — | — | — | — | — |
| *Chapmannia floridana* | AF203543 | — | — | — | — | — |
| *Chapmannia prismatica* | AJ320400 | — | — | — | — | — |
| *Chapmannia somalensis* | AF203544 | — | — | — | — | — |
| *Ormocarpopsis aspera* | AF068148 | — | — | — | — | — |
| *Ormocarpopsis calcicola* | AF068145 | — | — | — | — | — |
| *Ormocarpopsis itremoensis* | AF068149 | — | — | — | — | — |
| *Ormocarpopsis mandrarensis* | AF068147 | — | — | — | — | — |
| *Ormocarpopsis parvifolia* | AF068144 | — | — | — | — | — |
| *Ormocarpopsis tulearensis* | AF068146 | — | — | — | — | — |
| *Diphysa humilis* | AF068162 | — | — | — | — | — |
| *Diphysa macrophylla* | AF189029 | — | — | — | — | — |
| *Diphysa suberosa* | AF189034 | — | — | — | — | — |
| Related Species of the Genus *Arachis* Not Belonging to Leguminous Plants | | | | | | |
| *Spigelia coelostylioides* | AF177992 | — | — | — | — | — |
| *Spigelia hedyotidea* | AF178005 | — | — | — | — | — |
| *Spigelia marilandica* | AF177991 | — | — | — | — | — |

B. Preparation of Template DNA for PCR (1) Samples Used for DNA Extraction

Peanut:

6 commercially available peanuts were used.

Buckwheat, Wheat, Soybean, Adzuki Bean and Corn:

Leaves that germinated from commercially available seeds of Shirahana soba (common buckwheat), wheat, 2 soybeans, 2 adzuki beans and corn were used.

(2) Isolation of DNA from Peanut

DNA isolation was conducted by using the QIAGEN Genomic-tip and the resulting isolate was purified by MACHEREY-NAGEL NucleoSpin as stated below.

Into a 15 ml-tube 1 g of a ground sample was transferred, added 10 ml of Buffer G2, 100 μl of Proteinase K (20 mg/ml) and 10 μl of RNase A (100 mg/ml), and they were mixed. The resulting mixture was incubated for 1 hour at 50° C. Then the resulting mixture was centrifuged for 10 min. at 3,000×g to obtain a supernatant. The resulting supernatant was applied to the Genomic-tip 20/G column equilibrated with 1 ml of Buffer QBT to adsorb DNA to the column. Subsequently, the column was washed with 4 ml of Buffer QC and DNA was eluted with 1 ml of preheated (50° C.) Buffer QF. To the eluate was added 4 volume of Buffer NT2, mixed with it, and then the resulting mixture was divided into two halves to be applied to two separate NucleoSpin Extract Columns. 650 μl of the mixture was applied to a NucleoSpin Extract Column and then the column was centrifuged for 1 min. at 6,000×g to adsorb DNA to the column. This step was repeated with the remaining mixture. In order to wash the column, to the column was added 600 μl of Buffer NT3 and was centrifuged for 1 min. at 6,000×g. To the column was added 600 μl of Buffer NT3 again and was centrifuged for 1 min. at a maximum speed to flush out the Buffer NT3 remaining in the column. Finally, to the column was added 100 μl of Buffer NE and was centrifuged for 1 min. at a maximum speed to obtain a DNA eluate from the column and the resulting eluate was subjected to isopropanol precipitation to collect DNA, which were then dissolved in 40 μl of sterilized ultrapure water. After the concentration of the resulting DNA preparation was determined, the DNA preparation was used for a PCR template.

(3) Isolation of DNA from Leaves of Shirahana Soba (Common Buckwheat), Wheat, Soybean, Adzuki Bean and Corn DNA isolation was conducted by using the QIAGEN DNeasy Plant Mini Kit according to the procedures described in the DNeasy Plant Mini Kit Handbook as shown below.

Into a 1.5 ml-tube 50 mg of a ground sample was transferred, added 600 μl of Buffer AP1 and 6 μl of RNase A (100 mg/ml), and they were mixed well. Then the resulting mixture was incubated for 1 hour at 65° C. 200 μl of Buffer AP2 was then added to the mixture. The resulting mixture was incubated for 10 min. on ice and then centrifuged to obtain a supernatant. The resulting supernatant was applied to a QIAshredder Spin Column and a flow-through fraction was obtained by centrifuging the column. To the flow-through fraction was added 0.5 volume of Buffer AP3 and 1 volume of ethanol, and mixed with them. The resulting mixture was divided into two halves to be applied to two DNeasy Spin Columns. 650 μl of the mixture was applied to a DNeasy Spin Column and the column was centrifuged for 1 min. at 6,000×g to adsorb DNA to the column. This step was repeated with the remaining mixture. In order to wash the column, to the column was added 500 μl of Buffer AW and was centrifuged for 1 min. at 6,000×g. To the column was added 500 μl of Buffer AW again and was centrifuged for 1 min. at a maximum speed to flush out the Buffer AW remaining in the column. Finally, to the column was added 100 μl of preheated (65° C.) Buffer AE and was centrifuged for 1 min. at a maximum speed, and added another 100 μl of preheated (65° C.) Buffer AE and was centrifuged for 1 min. at a maximum speed to obtain a DNA eluate from the column, and the resulting eluate was subjected to isopropanol precipitation to collect DNA, which were then dissolved in 50 μl of sterilized ultrapure water. After the concentration of the resulting DNA preparation was determined, the DNA eluate was used for a PCR template.

(4) Preparation of DNA Solutions for Evaluation of Sensitivity (Peanut in Wheat)

A DNA preparation derived from peanut seeds was diluted stepwise with a DNA preparation from wheat leaves to obtain wheat leaf DNA solutions containing 10 ppm and 1 ppm of peanut seed DNA. The DNA preparation from peanut seeds was obtained according to the procedures described in (2). The DNA preparation from wheat leaves was obtained according to the procedures described in (3).

C. PCR (Part 1: A Combination of Primers with SEQ NOs:18 and 3)

PCR was conducted using the Applied Biosystems AmpliTaq Gold(R) & 10×PCR Buffer II & MgCl$_2$ Solution with dNTP as stated below.

Figure 8:
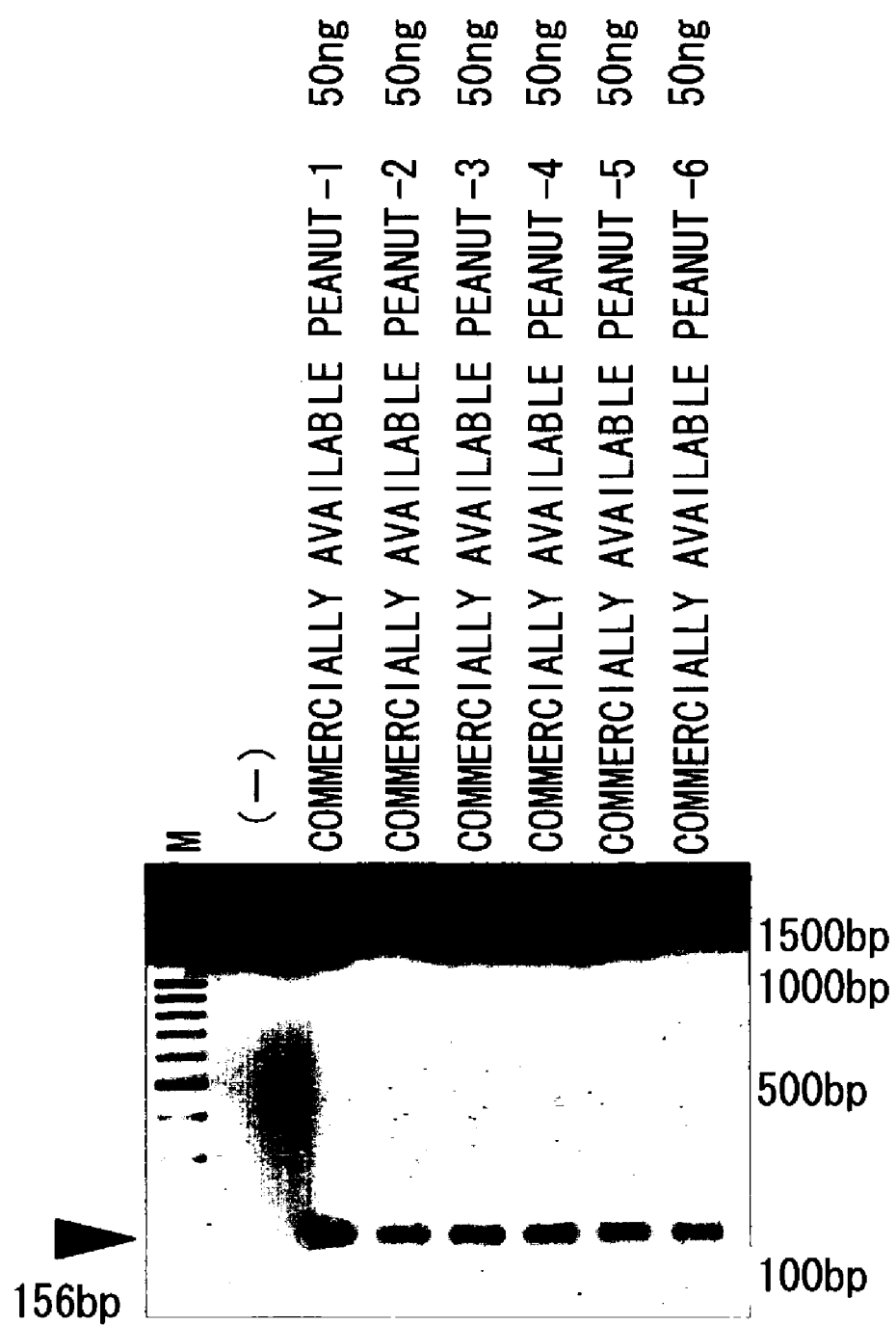
FIG. 8 is an electrophoretogram showing the results electrophoresed on a 2% agarose gel in Example 5.

PCR was carried out using final volumes of 25 µl of a solution containing 2.5 µl of 10×PCR Buffer II, 0.125 µl of AmpliTaq Gold (5 U/µl), 2.5 µl of dNTPs Mix (2 mM each), 1.5 µl of MgCl$_2$ Solution (25 mM), 0.5 µM of each primer (SEQ NO:18 and SEQ NO:3), the template DNA and sterilized ultrapure water in 0.2-ml microcentrifuge tubes. Amplification was performed using a GeneAmp PCR System 2400 (Applied Biosystems) according to the following PCR program: pre-incubation at 95° C. for 15 min.; 45 cycles consisting of denaturation at 95° C. for 1 min., annealing at 66° C. for 2 min. and extension at 72° C. for 1 min.; followed by a final extension at 72° C. for 4 min. The PCR reaction mixture was electrophoresed on a 2% agarose gel containing ethidium bromide. After the electrophoresis, the gel was analyzed using a FluorImager 595 (Amersham Pharmacia Biotech). The results are shown in FIG. 8. The meanings of numerical values, abbreviations and symbols used in FIG. 8 are as follows.

M: 100 bp DNA Ladder Marker
(−): Negative control (no DNA)
Numerical values above sample names: the amounts of the template DNA
Arrow: indicates the target amplification product (156 bp)

D. PCR Results (Part 1: A Combination of Primers with SEQ NOs:18 and 3)

PCR described above was conducted using primers designed in the present invention. The results are shown in FIG. 8. As shown in FIG. 8, target 156 bp amplification products, predicted from the simulation results of ITS-1~5.8S rRNA gene sequences of the genus Arachis, were obtained from 6 commercially available peanuts. Because this result almost matched the simulation results shown in Table 3, the simulation results were thought to be reliable.

E. Preparation of a Sequencing Sample (Part 1: A Combination of Primers with SEQ NOs:18 and 3)

(1) Purification of the Amplification Product from Peanut

A purification of the amplification product from peanut obtained in D was conducted in the same way as in Example 1 E (1) "Purification of the Amplification Product from Buckwheat Chaff".

(2) Sequencing PCR Reaction and Removal of Excess Dye-Labeled Dideoxynucleotides PCR for sequencing of the purified amplification product from peanut obtained in (1) was conducted in the same way as in Example 1 E (2) "Sequencing PCR Reaction and Removal of Excess Dye-Labeled Dideoxynucleotides", except for use of primers with SEQ NOs:18 and 3.

F. Sequence Analysis (Part 1: A Combination of Primers with SEQ NOs:18 and 3)

Figure 9:
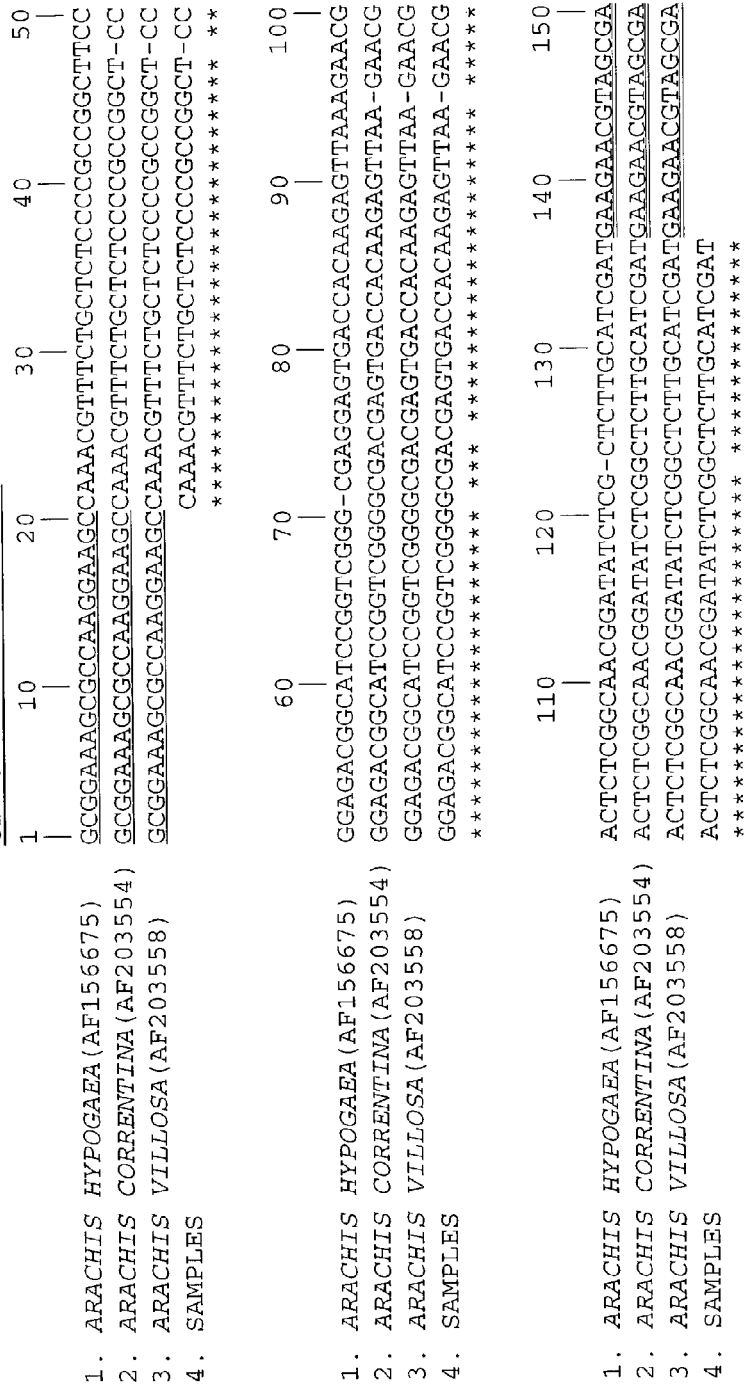
FIG. 9 is nucleotide sequences obtained by a sequence analysis of the target amplification product from peanut.

The sample for sequencing from peanut obtained in E (2) was analyzed using an ABI PRISM 310 Genetic Analyzer (Applied Biosystems). The obtained nucleotide sequence of the amplification product was compared with the sequence of the genus Arachis, Arachis hypogaea (AF156675), A. correntina (AF203554) and A. villosa (AF203558) in GenBank. The result is shown in FIG. 9. The meanings of number symbols above a nucleotide sequence, lines underneath a sequence and other symbols used in FIG. 9 are described below.

Number Symbols: Nucleotide numbers of amplification products
Asterisks (*): Nucleotides of the peanuts, which are identical with those of all of the nucleotide sequences of Arachis hypogaea (AF156675), A. correntina (AF203554) and A. villosa (AF203558) in GenBank
Single underline: The sense primer region
Double underline: The antisense primer region G. The Result of Sequence Analysis (Part 1: A Combination of Primers with SEQ NOs:18 and 3)

As shown in FIG. 9, the amplification products derived from all of the 6 commercially available peanuts obtained by PCR using the primers designed in the present invention completely (100%) matched from one another, and both the sequence of A. correntina (AF203554) and that of A. villosa (AF156675) completely matched 114 bases between two primer regions. This result indicates the target ITS-1~5.8S rRNA gene sequence of the genus Arachis can be detected without fail. In this connection, the target amplification product differed from A. hypogaea (AF156675) at 5 positions, particularly the 48$^{th}$ base "T" thereof was not present in the genus Arachis except for A. hypogaea (AF156675) in GenBank and it is not present in the commercially available peanuts experimented on here. It was found that, in order to design widely detectable primers to the genus Arachis, which includes commercially available peanuts, a DNA sequence of commercially available peanuts, A. correntina (AF203554) or A. villosa (AF203558), was preferably used in place of a DNA sequence of A. hypogaea (AF156675) in GenBank, and therefore, that the sense primer with SEQ NO:20 designed from the sequence of commercially available peanuts, A. correntina (AF203554) or A. villosa (AF203558) was used rather than the sense primer with SEQ NO:19 designed from the sequence of A. hypogaea (AF156675).

H. PCR (Part 2: A Combination of Primers with SEQ NOs:20 and 3)

PCR was conducted using the QIAGEN HotStarTaq Master Mix Kit according to the procedures described in the HotStarTaq PCR Handbook as stated below.

Figure 10:
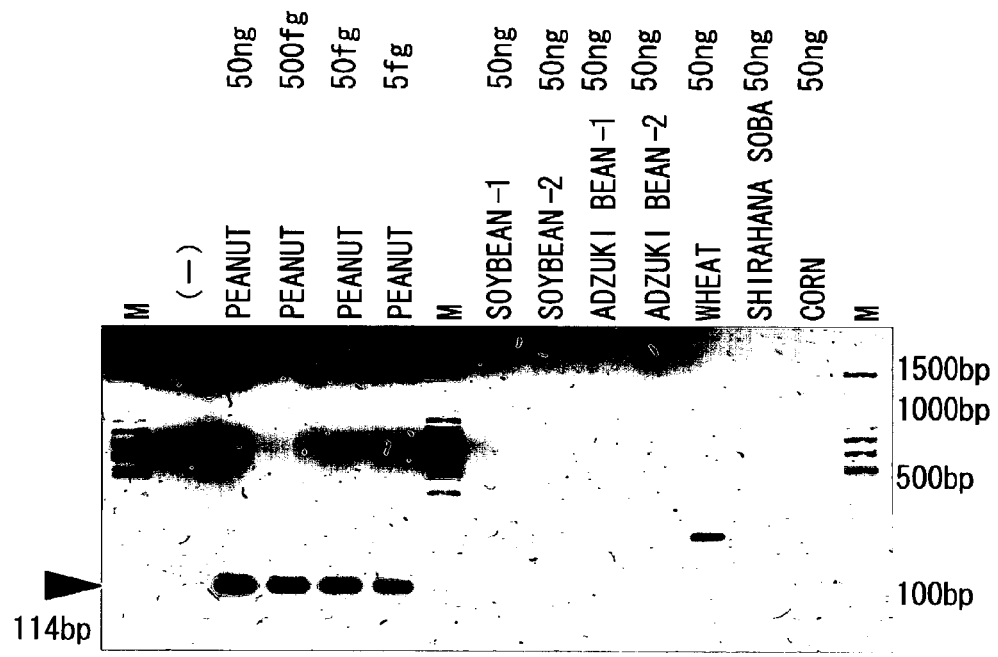
FIG. 10 is an electrophoretogram showing the results electrophoresed on a 2% agarose gel in Example 6.
Figure 11:
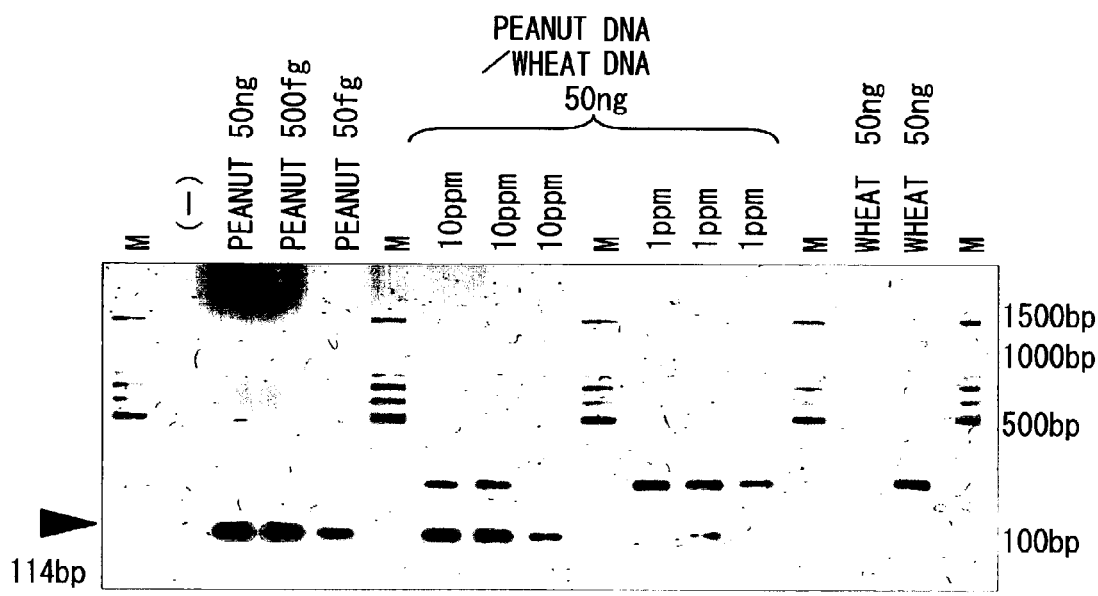
FIG. 11 is an electrophoretogram showing the results electrophoresed on a 2% agarose gel in Example 6.
Figure 13:
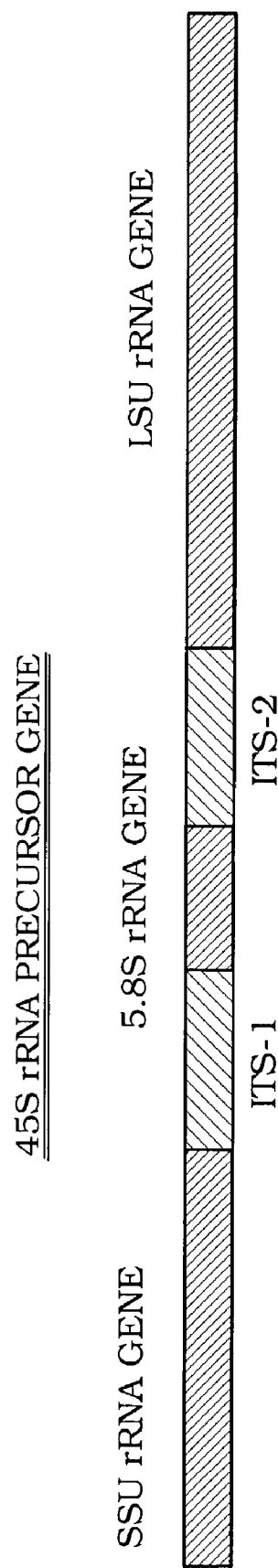
FIG. 13 is 45S rRNA precursor gene structure.

PCR was carried out using final volumes of 25 µl of a solution containing 12.5 µl of 2× HotStarTaq Master Mix (HotStarTaq DNA Polymerase, PCR Buffer with 3 mM MgCl$_2$, 400 µM each dNTP), 0.5 µM of each primer (SEQ NO:20 and SEQ NO:3), the template DNA and sterilized ultrapure water in 0.2-ml microcentrifuge tubes. Amplification was performed using a Sequence Detection System ABI PRISM 7700 (Applied Biosystems) according to the following PCR program: pre-incubation at 95° C. for 15 min.; 25 cycles consisting of denaturation at 95° C. for 30 secs, annealing and extension at 75° C. for 30 secs. respectively and 30 cycles consisting of denaturation at 95° C. for 30 secs., annealing and extension at 72° C. for 30 secs. respectively; followed by a final extension at 72° C. for 5 min. The resulting PCR reaction mixture was electrophoresed on a 2% agarose gel containing ethidium bromide. After the electrophoresis, the gel was analyzed using a FluorImager 595 (Amersham Pharmacia Biotech). The results are shown in FIGS. 10 and 11. The meanings of numerical values, abbreviations and symbols used in FIGS. 10 and 11 are as follows.

M: 100 bp DNA Ladder Marker
(−): Negative control (no DNA)

Numerical values above sample names: the amounts of the template DNA

Arrow: indicates the target amplification product (114 bp)

The quality of each of the template DNA used here was sufficient enough to be used for PCR based on the result of a separate PCR, in which target products were obtained using a primer pair to amplify a part of plant chloroplast DNA.

I. PCR Results (Part 2: A Combination of Primers with SEQ NOs:20 and 3)

PCR described above was conducted using primers designed in the present invention. The results are shown in FIGS. 10 and 11. As shown in FIG. 10, target 114 bp amplification products, predicted from the simulation results of the ITS-1~5.8S rRNA gene sequence of the genus *Arachis*, were obtained from peanuts. On the other hand, no 114 bp amplification product was obtained from buckwheat, wheat, soybean, adzuki bean and corn. However, nonspecific amplification products, which were different from the target product in size, were obtained from wheat (approximately 250 bp). Because these results almost matched the simulation results shown in Table 4, the simulation results were thought to be reliable. Consequently, it was confirmed that a wide range of plants in the genus Arachis including commercially available peanuts were detectable using the present invention.

As shown in FIG. 11, the target 114 bp amplification product, predicted from the simulation results of the ITS-1~5.8S rRNA gene sequence of the genus *Arachis*, was obtained from the wheat DNA sample containing 1 ppm of peanut DNA. This result showed that even where 10 to 1 ppm of peanut DNA is present in wheat DNA, the peanut can be detectable.

Furthermore, the nonspecific amplification product from wheat that was obviously different from the target product in size did not interfere in the detection of 1 ppm of peanut DNA.

In this connection, as shown in Examples 1, 2 and 3, where a W value, which shows a possibility of obtaining amplification products in a simulation by Amplify, is not more than W4, it has been found that the amplification products, which differ from the target one, are obtained in some cases and not obtained in other cases in actual PCR. Please note that Tables 1 to 4 show the data of the simulation results of Amplify which are of W2 value or higher but do not show those of a lower W value such as W1 and W0 wherein the possibility of obtaining the amplification products is considered to be low.

J. Preparation of a Sequencing Sample (Part 2: A Combination of Primers with SEQ NOs:20 and 3)

(1) Purification of the Amplification Product from Peanut

The purification of the amplification product from peanut obtained in I was conducted in the same way as in Example 1 E (1) "Purification of the Amplification Product from Buckwheat Chaff".

(2) Sequencing PCR Reaction and Removal of Excess Dye-Labeled Dideoxynucleotides PCR for sequencing of the purified amplification product from peanut obtained in (1) was conducted in the same way as in Example 1 E (2) "Sequencing PCR Reaction and Removal of Excess Dye-Labeled Dideoxynucleotides", except for use of primers with SEQ NOs:20 and 3.

K. Sequence Analysis (Part 2: A Combination of Primers with SEQ NOs:20 and 3)

The sample for sequencing from peanut obtained in J (2) was analyzed using an ABI PRISM 310 Genetic Analyzer (Applied Biosystems). The obtained nucleotide sequence of the amplification product was compared with the sequence of *Arachis hypogaea* (AF156675), *A. correntina* (AF203554), *A. villosa* (AF203558), *A. major* (AF203552) and *A. hermannii* (AF203556) in the genus *Arachis* and the nucleotide sequence of the commercially available peanut obtained in G. The result is shown in FIG. 12. The meanings of number symbols above a nucleotide sequence, lines underneath this sequence and other symbols used in FIG. 12 are described below.

Number Symbols: Nucleotide numbers of amplification products

Commercially available peanuts: A part of the nucleotide sequence of the commercially available peanuts obtained in G Asterisks (*): Nucleotides of the peanuts, which are identical with those of all of the sequences of *Arachis hypogaea* (AF156675), *A. correntina* (AF203554), *A. villosa* (AF203558), *A. major* (AF203552) and *A. hermannii* (AF203556) in the genus *Arachis* and the sequence of the commercially available peanut obtained in G.

Single underline: The sense primer region

Double underline: The antisense primer region

L. The result of Sequence Analysis (Part 2: A Combination of Primers with SEQ NOs:20 and 3)

As shown in FIG. 12, a part of the nucleotide sequence of an amplification product derived from commercially available peanuts obtained by PCR using the primers designed in the present invention completely (100%) matched 75 bases between two primer regions of respective sequences of *Arachis correntina* (AF203554), *A. vilosa* (AF203558), *A. Major* (AF203552) and *A. herinannii* (AF203556). In this connection, the target amplification product differed from *Arachis hypogaea* (AF156675) at 4 positions, but completely (100%) matched the nucleotide sequence of the commercially available peanuts obtained in G. This result indicates the target ITS-1~5.8S rRNA gene sequence of the genus *Arachis* can be detected without fail.

Example 4

A. Design of Oligonucleotide Primers for Detection of DNA from Buckwheat (1) DNA Sequences of the Genus *Fagopyrum*, other Common Allergenic Plants and Plants Widely Used for a Food Ingredient The DNA sequences described in Example 1 A (1) "DNA sequences of the Genus *Fagopyrum*", (2) "DNA Sequences of other common allergenic plants" and (3) "DNA Sequences of Plants Widely Used for a Food Ingredient" were examined to select suitable regions for the primers.

(2) DNA Sequence of Plants in Related Species of the Genus *Fagopyrum*

The DNA sequences described in Example 2 A (2) "DNA Sequence of Plants in Related Species of the Genus *Fagopyrum*" were selected.

(3) Oligonucleotide Primer Synthesis

Among ITS-1 sequences of the aforementioned 21 DNA sequences of the genus *Fagopyrum*, there was determined a nucleotide sequence which would specifically hybridize to all of the 21 DNA sequences of the genus *Fagopyrum* through the study of the ITS-1 sequences. The thus determined nucleotide sequence is indicated as SEQ NO:15.

Subsequently, the oligonucleotide primer with SEQ NO:15 was synthesized.

```
Sense primer
5'-CGT TGC CGA GAG TCG TTC TGT TT-3'   (SEQ NO:15)
```

The oligonucleotide primer with SEQ NO:14 was also used as an antisense primer, the same as in Example 2.

B. PCR Simulation

Regarding the sense and antisense primer pair, the simulation was conducted with PCR simulation software, Amplify 1.0 (Bill Engels), which is the same as in Example 1, to examine whether a target size of amplification products would be obtained from the 21 DNA sequences of the genus *Fagopyrum*, the 8 DNA sequences of common allergenic plants other than buckwheat (peanut, wheat, soybean, walnut, *matsutake* mushroom, apple and orange), the 4 DNA sequences of plants widely used for a food ingredient (corn, brown rice, pepper and mustard) and the 27 sequences of related species of the genus *Fagopyrum*.

The simulation results are shown in Tables 5A and 5C. The meanings of symbols and numerical values in Tables 5A and 5C are explained below.

★: An obtained amplification product whose size almost matched the target 140 bp (±10 bp).

W 2–6: Probability of obtaining amplification products
High Probability - - - W6>W5>W4>W3>W2 - - - Low Probability Numerical values followed by bp:

Each value was obtained by subtracting 2 from the value obtained in the simulation.

(−): No amplification product was predicted.

Related Species of the Genus *Fagopyrum*:

Sequences similar to the ITS-1 sequence of *Fagopyrum esculentum* (AB000330) were searched by means of a BLAST homology search and the sequences having a score of 60 bits or more were selected from among them. Each sequence having the highest score in each genus and having a score of 60 bits or more is shown in the following Tables 5B–5C as the representative of the DNA sequences of related species of the genus *Fagopyrum*.

C. Preparation of Template DNA for PCR

The DNA samples isolated from Shirahana soba (common buckwheat) and Dattan soba (Tartarian buckwheat) in Example 1 B (2) were diluted stepwise with sterilized ultrapure water to use them. The DNA samples isolated from white pepper in Example 1 B (2), mustard in Example 1 B (3), peanut in Example 3 B (2) and wheat, soybean, and corn in Example 3 B (3) were also used. In addition, the DNA samples isolated from brown rice seeds and *Fallopia convolvulus* in the same way as in Example 1 B (3) were used. The DNA samples from *Fallopia convolvulus* were diluted stepwise with sterilized ultrapure water to use.

D. PCR

PCR was conducted in essentially the same way as in Example 1 C, except for use of the following primers and PCR program.

Primers:

Each primer of SEQ NO:14 and SEQ NO:15 was used at 0.5 μM of a final concentration.

PCR program:

PCR was conducted according to the following PCR program.

Pre-incubation at 95° C. for 15 min.; thereafter 45 cycles consisting of denaturation at 95° C. for 1 min., annealing at 66° C. for 2 min. and extension at 72° C. for 1 min.; followed by a final extension at 72° C. for 4 min.

E. Results

Regarding the primers of the present invention, the simulation was conducted with PCR simulation software, Amplify 1.0 (Bill Engels) to examine the specificity to the ITS-1~5.8S rRNA gene sequence of each plant. As a result, as shown in Tables 5A to 5C, it was predicted that target 101 bp amplification products would be obtained from the aforementioned 21 DNA sequences of the genus *Fagopyrum*. On the other hand, it was predicted that no target 101 bp amplification product would be obtained from the 8 DNA sequences of other common allergenic plants (peanut, wheat, soybean, walnut, *matsutake* mushroom, peach, apple and orange), the 4 DNA sequences of plants widely used for a food ingredient (corn, brown rice, pepper and mustard) and the 27 DNA sequences of related species of the genus *Fagopyrum* both belonging to Polygonaceae and not belonging to Polygonaceae. Also, no nonspecific amplification product could be predicted. As a result, it was confirmed that a wide lange of plants in the genus *Fagopyrum* would be specifically detectable using the present invention.

TABLE 5A

Buckwheat, SEQ No:14 & SEQ No:15 primer: Amplification products

| Scientific Name (Common Name) Genus *Fagopyrum* | GenBank Accession No. | W6 | W5 | W4 | W3 | W2 |
|---|---|---|---|---|---|---|
| ★*Fagopyrum urophyllum* | AB000342 | 101 bp | — | 439 bp | — | — |
| ★*Fagopyrum urophyllum* | AB000341 | 101 bp | — | — | — | — |
| ★*Fagopyrum tataricum* (Tartarian buckwheat) | AB000340 | 101 bp | — | — | — | — |
| ★*Fagopyrum tataricum* (Tartarian buckwheat) | AB000339 | 101 bp | — | — | — | — |
| ★*Fagopyrum statice* | AB000338 | 101 bp | — | — | — | — |
| ★*Fagopyrum statice* | AB000337 | 101 bp | — | — | — | — |
| ★*Fagopyrum pleioramosum* | AB000336 | 101 bp | — | — | — | — |
| ★*Fagopyrum lineare* | AB000335 | 101 bp | — | — | — | — |
| ★*Fagopyrum leptopodum* | AB000334 | 101 bp | — | — | — | — |
| ★*Fagopyrum homotropicum* | AB000333 | 101 bp | — | — | — | — |
| ★*Fagopyrum gracilipes* | AB000332 | 101 bp | — | — | — | — |
| ★*Fagopyrum esculentum* (Common buckwheat) | AB000331 | 101 bp | — | — | — | — |
| ★*Fagopyrum esculentum* (Common buckwheat) | AB000330 | 101 bp | — | — | — | — |
| ★*Fagopyrum cymosum* | AB000329 | 101 bp | — | — | — | — |
| ★*Fagopyrum cymosum* | AB000328 | 101 bp | — | — | — | — |
| ★*Fagopyrum cymosum* | AB000327 | 101 bp | — | — | — | — |
| ★*Fagopyrum cymosum* | AB000326 | 101 bp | — | — | — | — |
| ★*Fagopyrum cymosum* | AB000325 | 101 bp | — | — | — | — |
| ★*Fagopyrum cymosum* | AB000324 | 101 bp | — | — | — | — |
| ★*Fagopyrum capillatum* | AB000323 | 101 bp | — | — | — | — |
| ★*Fagopyrum callianthum* | AB000322 | 101 bp | — | 440 bp | — | — |

TABLE 5B

Buckwheat, SEQ No:14 & SEQ No:15 primer: Amplification products

| Scientific Name (Common Name) | GenBank Accession No. | W6 | W5 | W4 | W3 | W2 |
|---|---|---|---|---|---|---|
| Other Common Allergenic Plants | | | | | | |
| *Arachis hypogaea* (Peanut) | AF156675 | — | — | — | — | — |
| *Triticum aestivum* (Wheat) | AJ301799 | — | — | — | — | — |
| *Glycine max* (Soybean) | U60551 | — | — | — | — | — |
| *Juglans regia* (Walnut) | AF303809 | — | — | — | — | — |
| *Tricholoma matsutake* (Matsutake mushroom) | U62964 | — | — | — | — | — |
| *Prunus persica* (Peach) | AF185621 | — | — | — | — | — |
| *Malus x domestica* (Apple) | AF186484 | — | — | — | — | — |
| *Citrus* sp. (Valencia orange) | E08821 | — | — | — | — | — |
| Plants Widely Used for a Food Ingredient | | | | | | |
| *Zea mays* (Corn) | U46648 | — | — | — | — | — |
| *Oryza sativa* (Brown rice) | AF169230 | — | — | — | — | — |
| *Piper nigrum* (Pepper) | AF275197 | — | — | — | — | — |
| *Sinapis alba* (Mustard) | X15915 | — | — | — | — | — |
| Related Species of the Genus *Fagopyrum* Belonging to Polygonaceae | | | | | | |
| *Aconogonum* sp. Won 152 | AF189731 | — | — | — | — | — |
| *Fallopia scandens* | AF040069 | — | — | — | — | — |
| *Polygonum virginianum* | U51274 | — | — | — | — | — |
| *Rumex acetosella* | AF189730 | — | — | — | — | — |

TABLE 5C

Buckwheat, SEQ No:14 & SEQ No:15 primer: Amplification products

| Scientific Name (Common Name) Related Species of the Genus *Fagopyrum* Not Belonging to Polygonaceae | GenBank Accession No. | W6 | W5 | W4 | W3 | W2 |
|---|---|---|---|---|---|---|
| *Talinum paraguayense* | L78056 | — | — | — | — | — |
| *Bruinsmia styracoides* | AF396438 | — | — | — | — | — |
| *Talinella pachypoda* | L78054 | — | — | — | — | — |
| *Rehderodendron kwangtungense* | AF396448 | — | — | — | — | — |
| *Pterostyrax corymbosus* | AF396445 | — | — | — | — | — |
| *Anredera cordifolia* | L78086 | — | — | — | — | — |
| *Cistanthe quadripetala* | L78062 | — | — | — | — | — |
| *Xenia vulcanensis* | L78060 | — | — | — | — | — |
| *Talinopsis frutescens* | L78058 | — | — | — | — | — |
| *Talinaria palmeri* | L78052 | — | — | — | — | — |
| *Portulaca* sp. | L78049 | — | — | — | — | — |
| *Phemeranthus confertiflorus* | L78039 | — | — | — | — | — |
| *Montiopsis umbellata* | L78033 | — | — | — | — | — |
| *Grahamia bracteata* | L78028 | — | — | — | — | — |
| *Herniaria glabra* | AJ310965 | — | — | — | — | — |
| *Alluaudia dumosa* | L78011 | — | — | — | — | — |

TABLE 5C-continued

Buckwheat, SEQ No:14 & SEQ No:15 primer: Amplification products

| Scientific Name (Common Name) Related Species of the Genus *Fagopyrum* Not Belonging to Polygonaceae | GenBank Accession No. | W6 | W5 | W4 | W3 | W2 |
|---|---|---|---|---|---|---|
| *Sinojackia xylocarpa* | AF396451 | — | — | — | — | — |
| *Halesia macgregori* | AF396442 | — | — | — | — | — |
| *Changiostyrax dolichocarpa* | AF396439 | — | — | — | — | — |
| *Alectryon subdentatus* | AF314765 | — | — | — | — | — |
| *Anacampseros recurvata* | L78014 | — | — | — | — | — |
| *Weinmannia racemosa* | AF485597 | — | — | — | — | — |
| *Bursera tecomaca* | AF080029 | — | — | — | — | — |

PCR described above was conducted using primers designed in the present invention. In this case, target 101 bp amplification products, predicted from the simulation results of the ITS-1~5.8S rRNA gene sequences of the genus *Fagopyrum*, were obtained from 500 to 50 fg of Shirahana soba (common buckwheat) DNA and Dattan soba (Tartarian buckwheat) DNA. As a result, it was found that even where 500 to 50 fg of buckwheat DNA is present, the buckwheat can be detected. In this connection, such sensitivity corresponds to a sensitivity wherein there can be detected 10 to 1 ppm of buckwheat DNA contained in the sample DNA when PCR was conducted with, as a template, 50 ng of DNA isolated from some samples. On the other hand, no amplification product having 101 bp or nonspecific amplification products was obtained from wheat, peanut, soybean, corn, mustard, pepper and brown rice. Furthermore, regarding *Fallopia convolvulus,* when an amount of template DNA is 50 to 5 ng, a target size of an amplification product was obtained with a very weak signal, but when an amount of template DNA is 500 pg or less, no amplification product in a target size or nonspecific amplification product was obtained at all. In this connection, regarding *Fallopia convolvulus,* when PCR was conducted with, as a template, 50 ng of DNA isolated from some samples, even if 1% of *Fallopia convolvulus* was present in sample DNA, the level of *Fallopia convolvulus* DNA corresponds to a non-detected level as false positive. By modification of PCR program, there is a possibility that amplification products in a target size will not be obtained from 50 to 5 ng of DNA from *Fallopia convolvulus*.

Consequently, in conjunction with the results of specificity studied by PCR simulation and of sensitivity and specificity studied by PCR, it was confirmed that a wide range of the genus *Fagopyrum* including common buckwheat and Tartarian buckwheat were detectable using the present invention.

Example 5

A. Design of Oligonucleotide Primers for Detection of DNA from Peanut (1) DNA Sequences of the Genus *Arachis*, other Common Allergenic Plants, Plants Widely Used for a Food Ingredient and Leguminous Plants Widely Used for a Food Ingredient The DNA sequences described in Example 3 A (1) "DNA Sequences of the Genus *Arachis*", Example 3 A (2) "DNA Sequences of Other Common Allergenic Plants", Example 3 A (3) "DNA Sequences of Plants Widely Used for a Food Ingredient" and Example 3 A (4) "DNA Sequences of Leguminous Plants Widely Used for a Food Ingredient" were examined to select suitable regions for the primers. In addition, as a DNA sequence of adzuki bean, 5.8S rRNA gene, ITS-2 sequences in the following DNA sequences registered in GenBank were selected.

1: adzuki bean: *Vigna angularis* var. *nipponensis* (AB060088)

(2) DNA Sequences of Plants in Related Species of the Genus *Arachis*

As representatives of the DNA sequences of related species of the genus *Arachis*, respective 5.8S rRNA gene, ITS-1 and ITS-2 sequences in the following 45 DNA sequences registered in GenBank were examined to select suitable regions for the primers. In this connection, the-45 DNA sequences were selected as representations, each of which was of highest Score in the species which were other than peanut (*Arachis hypogaea* AF156675) and were of Score of 60 bits or more among sequences of said species hit to ITS-2 sequence of peanut through BLAST homology search.

1: *Chapmannia floridana* (AF203543)
2: *Chapmannia gracilis* (AF203546)
3: *Chapmannia prismatica* (AJ320400)
4: *Chapmannia reghidensis* (AF204232)
5: *Chapmannia sericea* (AF203548)
6: *Chapmannia somalensis* (AF203544)
7: *Chapmannia tinireana* (AF203547)
8: *Fiebrigiella gracilis* (AF203561)
9: *Fissicalyx fendleri* (AF189061)
10: *Stylosanthes acuminata* (AJ320282)
11: *Stylosanthes angustifolia* (AJ320284)
12: *Stylosanthes aurea* (AJ320285)
13: *Stylosanthes biflora* (AJ320289)
14: *Stylosanthes bracteata* (AJ320346)
15: *Stylosanthes calcicola* (AJ320348)
16: *Stylosanthes campestris* (AJ320291)
17: *Stylosanthes capitata* (AJ320350)
18: *Stylosanthes cayennensis* (AJ320292)
19: *Stylosanthes erecta* (AJ320352)
20: *Stylosanthes fruticosa* (AJ320356)
21: *Stylosanthes gracilis* (AJ320296)
22: *Stylosanthes grandifolia* (AJ320299)
23: *Stylosanthes guianensis* subsp. *dissitiflora* (AJ320301)
24: *Stylosanthes hamata* (AJ320365)
25: *Stylosanthes hippocampoides* (AJ320316)
26: *Stylosanthes hispida* (AJ320328)
27: *Stylosanthes humilis* (AJ320327)
28: *Stylosanthes ingrata* (AJ320329)
29: *Stylosanthes leiocarpa* (AJ320332)
30: *Stylosanthes linearifolia* (AJ320367)
31: *Stylosanthes macrocarpa* (AJ320369)
32: *Stylosanthes macrocephala* (AJ320371)
33: *Stylosanthes macrosona* (AJ320333)
34: *Stylosanthes mexicana* (AJ320373)
35: *Stylosanthes montevidensis* (AJ320336)
36: *Stylosanthes pilosa* (AJ320377)
37: *Stylosanthes scabra* (AJ320382)
38: *Stylosanthes seabrana* (AJ320384)
39: *Stylosanthes sericeiceps* (AJ320386)
40: *Stylosanthes subsericea* (AJ320387)
41: *Stylosanthes sundaica* (AJ320389)
42: *Stylosanthes sympodialis* (AJ32039 1)
43: *Stylosanthes tomentosa* (AJ320337)
44: *Stylosanthes tuherculata* (AJ320392)
45: *Stylosanthes viscosa* (AJ320340)

In addition, if PCR simulation is conducted by selecting a primer hybridized to ITS-1 sequence, the DNA sequences described in Example 3 A (5) "DNA Sequences of Plants in Related Species to the Genus *Arachis*" were also selected.

(3) Oligonucleotide Primer Synthesis (a) Among 5.8S rRNA gene sequences of the aforementioned 11 DNA sequences of the genus *Arachis* and the aforementioned 8 DNA sequences of other common allergenic plants, there was determined nucleotide sequences which would hybridize to all DNA sequences of these plants through the study of the sequences. The thus determined nucleotide sequence is indicated as SEQ NO:7. Subsequently, the oligonucleotide primer with SEQ NO:7 was synthesized.

```
Sense primer                            (SEQ NO:7)
5'-GAT GAA GAA CGT AGC GAA ATG CGA TAC T-3'
```

Among ITS-2 sequences of the aforementioned 11 DNA sequences of the genus *Arachis*, there was determined nucleotide sequences which would specifically hybridize to all of the 11 DNA sequences of the genus *Arachis* through the study of the sequences. The thus determined nucleotide sequence is indicated as SEQ NO:24. Subsequently, the oligonucleotide primer with SEQ NO:24 was synthesized.

```
Antisense primer
5'-CCA TCT GCC GCG GTG CC-3'      (SEQ NO:24)
```

(b) Furthermore, in another combination of primers, the primer of SEQ NO:18 described in Example 3 was selected as sense primer on the ITS-1 sequence and the primer of SEQ NO:24 was selected as antisense primer on the ITS-2 sequence.

B. PCR Simulation

Regarding the sense and antisense primer pairs, the simulation was conducted with PCR simulation software, Amplify 1.0 (Bill Engels), which is the same as in Example 1 to examine whether target size of amplification products are obtained from the 11 DNA sequences of the genus *Arachis*, the 8 DNA sequences of common allergenic plants other than peanut (buckwheat, wheat, soybean, walnut, *matsutake* mushroom, peach, apple and orange), the 4 DNA sequences of plants widely used for a food ingredient (corn, brown rice, pepper and mustard), the 6 DNA sequence of leguminous plants widely used for a food ingredient (French bean, lima bean, lentil, chickpea, mung bean and adzuki bean) and the DNA sequences of plants in related species of the genus *Arachis*.

(a) The simulation results using a combination of primers of SEQ NOs:7 and 24 are shown in Tables GA to 6D. The meanings of symbols and numerical values in Tables GA to 6D are explained below.

★: An obtained amplification product whose size almost matched the target 140 bp (±10 bp).

W 2–6: Probability to obtain amplification products
High Probability - - - W6>W5>W4>W3>W2 - - - Low Probability Numerical values followed by bp:

Each value was obtained by subtracting 2 from the value obtained in the simulation.

(−): No amplification product was predicted.

Related Species of the Genus *Arachis*:

Sequences similar to the ITS-2 sequence of *Arachis hypogaea* (AF156675) were searched by means of a BLAST homology search and the sequences having a score of 60 bits or one were selected among them. Each sequence having the highest score in each genus and having a score of 60 bits or more is shown in the following Tables 6B–6D as the representative of the DNA sequences of related species of the genus *Arachis*.

(–*): No annealing site of the primer (SEQ NO: 24) was predicted within the ITS-2 sequence of *Vigna angularis* var. *nipponensis* (adzuki bean).

In the case of adzuki bean, only the ITS-2 sequence was selected because the 5.8S rRNA gene sequence of *Vigna angularis* var. *nipponensis* (AB059747) was not registered in GenBank.

(b) The simulation results using a combination of primers of SEQ NOs:18 and 24 are shown in Tables 7A to 7E. The meanings of symbols and numerical values in Tables 7A to 7E are explained below.

★: An obtained amplification product whose size almost matched the target 140 bp (±10 bp).

W 2–6: Probability to obtain amplification products
High Probability - - - W6>W5>W4>W3>W2 - - - Low
Probability Numerical values followed by bp:

Each value was obtained by subtracting 2 from the value obtained in the simulation.

(–): No amplification product was predicted.

Related Species of the Genus *Arachis*,

Sequences Similar to the ITS-1 or ITS-2 sequence of *Arachis hypogaea* (AF156675) were searched by means of a BLAST homology search and the sequences having a score of 60 bits or more were selected among them. Each sequence having the highest score in each genus and having a score of 60 bits or more is shown in the following Tables 7B–7E as the representative of the DNA sequences of related species of the genus *Arachis*.

(–*): No annealing site of the primer (SEQ NO: 18) was predicted within the ITS-1 sequence of *Vigna angularis* var. *nipponensis* (adzuki bean) and no annealing site of the primer (SEQ NO:24) was predicted within the ITS-2 sequence of *Vigna angularis* var. *nipponensis* (adzuki bean).

In the case of adzuki bean, only either the ITS-1 or ITS-2 sequence was selected respectively because full length of the ITS-1~5.8S rRNA gene~ITS-2 sequence of *Vigna angularis* var. *nipponensis* (AB059747) was not registered in GenBank.

C. Preparation of Template DNA for PCR

A DNA preparation from peanut isolated in Example 3 B (2) was diluted stepwise with sterilized ultrapure water to use.

D. PCR

PCR was conducted in substantially the same way as in Example 1 C, except for use of following primers and PCR program.

Primer:

(a) Each primer of SEQ NO:7 and SEQ NO:24 was used at 0.5 μM of final concentration.
(b) Each primer of SEQ NO:18 and SEQ NO:24 was used at 0.5 μM of final concentration.

PCR program:

PCR was conducted according to the following PCR program.

Pre-incubation at 95° C. for 15 min.; thereafter 45 cycles consisting of denaturation at 95° C. for 1 min., annealing at 68° C. for 1 min. and extension at 72° C. for 1 min.; followed by a final extension at 72° C. for 4 min.

The quality of each of the template DNA used here was sufficient enough to be used for PCR based on the result of a separate PCR, in which target products were obtained using a primer pair to amplify a part of plant chloroplast DNA.

E. Results (a) Results of the Combination of the Primers of SEQ NOs:7 and 24

Regarding the primers of the present invention (the combination of the primers of SEQ NOs:7 and 24), the simulation was conducted with PCR simulation software, Amplify 1.0 (Bill Engels) to examine the specificity to 5.8S rRNA gene~ITS-2 sequence of each plants. As a result, as shown in Tables 6A to 6D, it was predicted that target 253 to 259 bp amplification products would be obtained from the aforementioned 11 DNA sequences of the genus *Arachis*. On the other hand, it was predicted that no target 253 to 259 bp amplification products would be obtained from the 8 DNA sequences of other common allergenic plants (buckwheat, wheat, soybean, walnut, *matsutake* mushroom, peach, apple and orange), the 4 DNA sequences of plants widely used for a food ingredient (corn, brown rice, pepper and mustard), the 6 DNA sequence of leguminous plants widely used for a food ingredient (French bean, lima bean, lentil, chickpea, mung bean and adzuki bean) and the 41 DNA sequences of plants in related species of the genus *Arachis* belonging to leguminous plants. In this connection, among the plants in related species of the genus *Arachis* belonging to leguminous plants, it was predicted by simulation that amplification products having almost 253 to 259 bp would be obtained from the DNA sequences of *Stylosanthes cayennensis*, *Stylosanthes hispida*, *Stylosanthes viscosa* and *Fissicalyx fendleri*, but these amplification products can be identified by sequence analysis. Optionally, whether these amplification products are peanut may be also identified by PCR showing in Example 3 and the like. As a result, it was confirmed that wide ranges of plants in the genus *Arachis* would be specifically detectable using the present invention.

TABLE 6A

Peanut, SEQ NO:7 & SEQ NO:24 primer: Amplification products

| Scientific Name (Common Name) | GenBank Accession No. | W6 | W5 | W4 | W3 | W2 |
|---|---|---|---|---|---|---|
| Genus *Arachis* | | | | | | |
| ★*Arachis batizocoi* | AF203553 | — | 253 bp | 318 bp 149 bp | 214 bp | — |
| ★*Arachis correntina* | AF203554 | — | 254 bp | 323 bp 150 bp | 219 bp | — |
| ★*Arachis hermannii* | AF203556 | — | 253 bp | 320 bp 149 bp | 216 bp | — |
| ★*Arachis hoehnei* | AJ320395 | — | 256 bp | 152 bp | — | — |
| ★*Arachis hypogaea* (Peanut) | AF156675 | — | 259 bp | 968 bp 941 bp 328 bp 175 bp 153 bp | 222 bp | 69 bp |
| ★*Arachis magna* | AF203555 | — | 254 bp | 322 bp 150 bp | 218 bp | — |
| ★*Arachis major* | AF203552 | — | 253 bp | 320 bp 149 bp | 216 bp | — |
| ★*Arachis palustris* | AF203557 | — | 254 bp | 323 bp 150 bp | 219 bp | — |
| ★*Arachis pintoi* | AF203551 | — | 254 bp | 323 bp 150 bp | 219 bp | — |

TABLE 6A-continued

Peanut, SEQ NO:7 & SEQ NO:24 primer: Amplification products

| Scientific Name (Common Name) | GenBank Accession No. | W6 | W5 | W4 | W3 | W2 |
|---|---|---|---|---|---|---|
| ★*Arachis triseminata* | AF204233 | — | 253 bp | 149 bp | — | — |
| ★*Arachis villosa* | AF203558 | — | 255 bp | 324 bp 151 bp | 220 bp | — |
| Other Common Allergenic Plants | | | | | | |
| *Fagopyrum esculentum* (Common buckwheat) | AB000330 | — | — | — | 160 bp | — |
| *Triticum aestivum* (Wheat) | AJ301799 | — | — | — | — | — |
| *Glycine max* (Soybean) | U60551 | — | — | — | — | — |
| *Juglans regia* (Walnut) | AF303809 | — | — | — | — | — |
| *Tricholoma matsutake* (Matsutake mushroom) | U62964 | — | — | — | — | — |
| *Prunus persica* (Peach) | AF185621 | — | — | — | — | — |
| *Malus* x *domestica* (Apple) | AF186484 | — | — | — | — | — |
| *Citrus* sp. (Valencia orange) | E08821 | — | — | — | — | — |

TABLE 6B

Peanut, SEQ NO:7 & SEQ NO:24 primer: Amplification products

| Scientific Name (Common Name) | GenBank Accession No. | W6 | W5 | W4 | W3 | W2 |
|---|---|---|---|---|---|---|
| Plants Widely Used for a Food Ingredient | | | | | | |
| *Zea mays* (Corn) | U46648 | — | — | — | — | 82 bp |
| *Oryza sativa* (Brown rice) | AF169230 | — | — | — | — | 99 bp 92 bp |
| *Piper nigrum* (Pepper) | AF275197 | — | — | — | — | — |
| *Sinapis alba* (Mustard) | X15915 | — | — | — | — | — |
| Leguminous Plants Widely Used for a Food Ingredient | | | | | | |
| *Phaseolus vulgaris* (French bean) | AF115169 | — | — | — | — | — |
| *Phaseolus lunatus* (Lima bean) | AF115175 | — | — | — | — | — |
| *Lens culinaris* subsp. *culinaris* (Lentil) | AF228066 | — | — | — | — | 98 bp |
| *Cicer arietinum* (Chickpea) | AJ237698 | — | — | — | — | — |
| *Vigna radiata* (Mung bean) | X14337 | — | — | — | — | — |
| *Vigna angularis* var. *nipponensis* (Adzuki bean)* | AB060088 | — | — | —* | — | — |
| Related Species of the Genus *Arachis* Belonging to leguminous Plants | | | | | | |
| *Chapmannia floridana* | AF203543 | — | — | 330 bp | 35 bp | 226 bp |
| *Chapmannia gracilis* | AF203546 | — | — | — | — | — |
| *Chapmannia prismatica* | AJ320400 | — | — | — | — | — |
| *Chapmannia reghidensis* | AF204232 | — | — | — | — | — |
| *Chapmannia sericea* | AF203548 | — | — | — | — | — |
| *Chapmannia somalensis* | AF203544 | — | — | — | — | — |
| *Chapmannia tinireana* | AF203547 | — | — | — | — | — |
| *Fiebrigiella gracilis* | AF203561 | — | — | — | — | — |
| ★*Fissicalyx fendleri* | AF189061 | — | — | 252 bp 170 bp | — | 349 bp 340 bp 258 bp 148 bp 66 bp |

TABLE 6C

Peanut, SEQ NO:7 & SEQ NO:24 primer: Amplification products

| Scientific Name (Common Name) Related Species of the Genus *Arachis* Belonging to Leguminous Plants | GenBank Accession No. | W6 | W5 | W4 | W3 | W2 |
|---|---|---|---|---|---|---|
| *Stylosanthes acuminata* | AJ320282 | — | — | — | — | — |
| *Stylosanthes angustifolia* | AJ320284 | — | — | — | — | — |
| *Stylosanthes aurea* | AJ320285 | — | — | — | — | — |
| *Stylosanthes biflora* | AJ320289 | — | — | — | — | — |
| *Stylosanthes bracteata* | AJ320346 | — | — | — | — | — |
| *Stylosanthes calcicola* | AJ320348 | — | — | — | — | — |
| *Stylosanthes campestris* | AJ320291 | — | — | — | — | — |
| *Stylosanthes capitata* | AJ320350 | — | — | — | — | — |
| ★*Stylosanthes cayennensis* | AJ320292 | — | 253 bp | 455 bp 170 bp | — | 372 bp |
| *Stylosanthes erecta* | AJ320352 | — | — | — | — | — |
| *Stylosanthes fruticosa* | AJ320356 | — | — | — | — | — |
| *Stylosanthes gracilis* | AJ320296 | — | — | — | — | — |
| *Stylosanthes grandifolia* | AJ320299 | — | — | — | — | — |
| *Stylosanthes guianensis* subsp. *dissitiflora* | AJ320301 | — | — | — | — | — |
| *Stylosanthes hamata* | AJ320365 | — | — | — | — | — |
| *Stylosanthes hippocampoides* | AJ320316 | — | — | — | — | — |
| ★*Stylosanthes hispida* | AJ320328 | — | 253 bp | 455 bp 170 bp | — | 372 bp |
| *Stylosanthes humilis* | AJ320327 | — | — | 170 bp | — | 66 bp |

TABLE 6D

Peanut, SEQ NO:7 & SEQ NO:24 primer: Amplification products

| Scientific Name (Common Name) Related Species of the Genus *Arachis* Belonging to Leguminous Plants | GenBank Accession No. | W6 | W5 | W4 | W3 | W2 |
|---|---|---|---|---|---|---|
| *Stylosanthes ingrata* | AJ320329 | — | — | — | — | — |
| *Stylosanthes leiocarpa* | AJ320332 | — | — | 175 bp | — | 71 bp |
| *Stylosanthes linearifolia* | AJ320367 | — | — | — | — | — |
| *Stylosanthes macrocarpa* | AJ320369 | — | — | — | — | — |

TABLE 6D-continued

Peanut, SEQ NO:7 & SEQ NO:24 primer: Amplification products

| Scientific Name (Common Name) Related Species of the Genus *Arachis* Belonging to Leguminous Plants | GenBank Accession No. | W6 | W5 | W4 | W3 | W2 |
|---|---|---|---|---|---|---|
| *Stylosanthes macrocephala* | AJ320371 | — | — | — | — | — |
| *Stylosanthes macrosoma* | AJ320333 | — | — | — | — | — |
| *Stylosanthes mexicana* | AJ320373 | — | — | — | — | — |
| *Stylosanthes montevidensis* | AJ320336 | — | — | — | — | — |
| *Stylosanthes pilosa* | AJ320377 | — | — | — | — | — |
| *Stylosanthes scabra* | AJ320382 | — | — | — | — | — |
| *Stylosanthes seabrana* | AJ320384 | — | — | — | — | — |
| *Stylosanthes sericeiceps* | AJ320386 | — | — | — | — | — |
| *Stylosanthes subsericea* | AJ320387 | — | — | — | — | — |
| *Stylosanthes sundaica* | AJ320389 | — | — | — | — | — |
| *Stylosanthes sympodialis* | AJ320391 | — | — | — | — | — |
| *Stylosanthes tomentosa* | AJ320337 | — | — | — | — | — |
| *Stylosanthes tuberculata* | AJ320392 | — | — | — | — | — |
| ★*Stylosanthes viscosa* | AJ320340 | — | 436 bp 253 bp | 149 bp | — | — |

PCR described above was conducted using primers designed in the present invention. In this case, target 253 to 259 bp amplification products, expected from the simulation results of the 5.8S rRNA gene~ITS-2 sequences of the genus *Arachis*, were obtained from 500 to 50 fg of peanut DNA. It is found from the results that even where 500 to 50 fg of peanut DNA is present, the peanut can be detected. In this connection, this sensitivity correspond to a sensitivity wherein there can be detected 10 to 1 ppm of peanut DNA contained in the sample DNA when PCR was conducted with, as a template, 50 ng of DNA isolated from some samples.

Consequently, in conjunction with the results of specificity studied by PCR simulation, and of sensitivity and specificity studied by PCR, it was confirmed that a wide range of the genus *Arachis* including peanut were detectable using the present invention.

(b) Results of the Combination of the Primers of SEQ NOs: 18 and 24

Regarding the primers of the present invention (the combination of the primers of SEQ NOs:18 and 24), the simulation was conducted with PCR simulation software, Amplify 1.0 (Bill Engels) to examine the specificity to ITS-1~5.8S rRNA gene~ITS-2 sequence of each plant. As a result, as shown in Tables 7A to 7E, it was predicted that target 384 to 390 bp amplification products would be obtained from the aforementioned 11 DNA sequences of the genus *Arachis*. On the other hand, it was predicted that no target 384 to 390 bp amplification products would be obtained from the 8 DNA sequences of other common allergenic plants (buckwheat, wheat, soybean, walnut, *matsutake* mushroom, peach, apple and orange), the 4 DNA sequences of plants widely used for a food ingredient (corn, brown rice, pepper and mustard), the 7 DNA sequence of leguminous plants widely used for a food ingredient (French bean, lima bean, lentil, chickpea, mung bean and adzuki bean), the 71 DNA sequences of plants in related species of the genus *Arachis* belonging to leguminous plants and the 3 DNA sequences of plants in related species of the genus *Arachis* not belonging to leguminous plants. Among the plants in related species of the genus *Arachis* belonging to leguminous plants, it was predicted by simulation that amplification products, which were almost matched 384 to 390 bp of the target one in size, would be obtained from the DNA sequences of *Stylosanthes cayennensis*, *Stylosanthes hispida*, *Stylosanthes viscose* and *Fissicalyx fendleri*, but these amplification products can be identified by sequence analysis. Optionally, whether these amplification products are peanut may be also identified by PCR showing in Example 3 and the like. As a result, it was confirmed that wide ranges of plants in the genus *Arachis* would be specifically detectable using the present invention.

TABLE 7A

Peanut, SEQ NO:18 & SEQ NO:24 primer: Amplification products

| Scientific Name (Common Name) | GenBank Accession No. | W6 | W5 | W4 | W3 | W2 |
|---|---|---|---|---|---|---|
| Genus *Arachis* | | | | | | |
| ★*Arachis batizocoi* | AF203553 | — | 384 bp 449 bp | 149 bp 72 bp | 214 bp | — |
| ★*Arachis correntina* | AF203554 | — | 385 bp 454 bp | 150 bp | 219 bp | — |
| ★*Arachis hermannii* | AF203556 | — | 384 bp 451 bp | 149 bp | 216 bp | — |
| ★*Arachis hoehnei* | AJ320395 | — | 387 bp | 152 bp 60 bp | — | — |
| ★*Arachis hypogaea* (Peanut) | AF156675 | — | 390 bp 459 bp | 306 bp 153 bp | 1099 bp 1072 bp 222 bp | 69 bp |
| ★*Arachis magna* | AF203555 | — | 385 bp 453 bp | 150 bp 72 bp | 218 bp | — |
| ★*Arachis major* | AF203552 | — | 384 bp 451 bp | 149 bp | 216 bp | — |
| ★*Arachis palustris* | AF203557 | — | 385 bp 454 bp | 150 bp 72 bp | 219 bp | — |
| ★*Arachis pintoi* | AF203551 | — | 386 bp 455 bp | 150 bp | 219 bp | — |
| ★*Arachis triseminata* | AF204233 | — | 384 bp 451 bp | 149 bp | — | — |
| ★*Arachis villosa* | AF203558 | — | 386 bp 455 bp | 151 bp | 220 bp | — |
| Other Common Allergenic Plants | | | | | | |
| *Fagopyrum esculentum* (Common buckwheat) | AB000330 | — | — | — | 160 bp | — |
| *Triticum aestivum* (Wheat) | AJ301799 | — | — | — | — | — |
| *Glycine max* (Soybean) | U60551 | — | — | — | — | — |
| *Juglans regia* (Walnut) | AF303809 | — | — | — | — | — |
| *Tricholoma matsutake* (Matsutake mushroom) | U62964 | — | — | — | — | — |
| *Prunus persica* (Peach) | AF185621 | — | — | — | — | — |
| ★*Malus* x *domestica* (Apple) | AF186484 | — | — | — | 467 bp 424 bp | — |
| *Citrus* sp. (Valencia orange) | E08821 | — | — | — | 103 bp | 280 bp |

TABLE 7B

Peanut, SEQ NO:18 & SEQ NO:24 primer: Amplification products

| Scientific Name (Common Name) | GenBank Accession No. | W6 | W5 | W4 | W3 | W2 |
|---|---|---|---|---|---|---|
| Plants Widely Used for a Food Ingredient | | | | | | |
| Zea mays (Corn) | U46648 | — | — | — | — | 82 bp |
| Oryza sativa (Brown rice) | AF169230 | — | — | — | 99 bp 92 bp | |
| Piper nigrum (Pepper) | AF275197 | — | — | — | — | — |
| Sinapis alba (Mustard) | X15915 | — | — | — | — | — |
| Leguminous Plants Widely Used for a Food Ingredient | | | | | | |
| Phaseolus vulgaris (French bean) | AF115169 | — | — | — | — | — |
| Phaseolus lunatus (Lima bean) | AF115175 | — | — | — | — | — |
| Lens culinaris subsp. culinaris (Lentil) | AF228066 | — | — | — | — | 98 bp |
| Cicer arietinum (Chickpea) | AJ237698 | — | — | — | — | 95 bp |
| Vigna radiata (Mung bean) | X14337 | — | — | — | — | — |
| Vigna angularis var. nipponensis (Adzuki bean)* | AB059747 | — | — | —* | — | — |
| Vigna angularis var. nipponensis (Adzuki bean)* | AB060088 | — | — | —* | — | — |
| Related Species of the Genus Arachis Belonging to Leguminous | | | | | | |
| Stylosanthes acuminata | AJ320282 | — | — | — | — | — |
| Stylosanthes angustifolia | AJ320284 | — | — | — | — | — |
| Stylosanthes aurea | AJ320285 | — | — | — | — | — |
| Stylosanthes biflora | AJ320289 | — | — | — | — | — |
| Stylosanthes bracteata | AJ320346 | — | — | — | — | — |
| Stylosanthes calcicola | AJ320348 | — | — | — | — | — |
| Stylosanthes campestris | AJ320291 | — | — | — | — | — |
| Stylosanthes capitata | AJ320350 | — | — | — | — | — |
| ★Stylosanthes cayennensis | AJ320292 | — | 384 bp | 455 bp | 301 bp | 372 bp |
| Stylosanthes erecta | AJ320352 | — | — | — | — | — |
| Stylosanthes fruticosa | AJ320356 | — | — | — | — | — |
| Stylosanthes gracilis | AJ320296 | — | — | — | — | — |
| Stylosanthes grandifolia | AJ320299 | — | — | — | — | — |

TABLE 7C

Peanut, SEQ NO:18 & SEQ NO:24 primer: Amplification products

| Scientific Name (Common Name) Related Species of the Genus Arachis Belonging to Leguminous | GenBank Accession No. | W6 | W5 | W4 | W3 | W2 |
|---|---|---|---|---|---|---|
| Stylosanthes guisnensis subsp. dissitiflora | AJ320301 | — | — | — | — | — |
| Stylosanthes hamata | AJ320365 | — | — | — | — | — |
| Stylosanthes hippocampoides | AJ320317 | — | — | — | — | — |
| ★Stylosanthes hispida | AJ320328 | — | 384 bp | 455 bp | 301 bp | 372 bp |
| Stylosanthes humilis | AJ320323 | — | — | — | — | — |
| Stylosanthes ingrata | AJ320329 | — | — | — | — | — |

TABLE 7C-continued

Peanut, SEQ NO:18 & SEQ NO:24 primer: Amplification products

| Scientific Name (Common Name) Related Species of the Genus Arachis Belonging to Leguminous | GenBank Accession No. | W6 | W5 | W4 | W3 | W2 |
|---|---|---|---|---|---|---|
| Stylosanthes leiocarpa | AJ320332 | — | — | — | 306 bp | 71 bp |
| Stylosanthes linearifolia | AJ320367 | — | — | — | — | — |
| Stylosanthes macrocarpa | AJ320369 | — | — | — | — | — |
| Stylosanthes macrocephala | AJ320371 | — | — | — | — | — |
| Stylosanthes macrosoma | AJ320333 | — | — | — | — | — |
| Stylosanthes mexicana | AJ320374 | — | — | — | — | — |
| Stylosanthes montevidensis | AJ320336 | — | — | — | — | — |
| Stylosanthes pilosa | AJ320377 | — | — | — | — | — |
| Stylosanthes scabra | AJ320382 | — | — | — | — | — |
| Stylosanthes seabrana | AJ320384 | — | — | — | — | — |
| Stylosanthes sericeiceps | AJ320386 | — | — | — | — | — |
| Stylosanthes subsericea | AJ320387 | — | — | — | — | — |
| Stylosanthes sundaica | AJ320389 | — | — | — | — | — |
| Stylosanthes sympodialis | AJ320391 | — | — | — | — | — |
| Stylosanthes tomentosa | AJ320337 | — | — | — | — | — |
| Stylosanthes tuberculata | AJ320392 | — | — | — | — | — |
| ★Stylosanthes viscosa | AJ320340 | — | 385 bp 436 bp | 149 bp | — | — |
| Stylosanthes hippocampoides | AJ320316 | — | — | — | — | — |
| Stylosanthes humilis | AJ320327 | — | — | — | 301 bp | 66 bp |
| Stylosanthes mexicana | AJ320373 | — | — | — | — | — |
| Ormocarpum bernierianum | AF189036 | — | — | — | — | — |
| Ormocarpum coeruleum | AF189037 | — | — | — | — | — |
| Ormocarpum drakei | AF189039 | — | — | — | — | 90 bp |

TABLE 7D

Peanut, SEQ NO:18 & SEQ NO:24 primer: Amplification products

| Scientific Name (Common Name) Related Species of the Genus Arachis Belonging to Leguminous | GenBank Accession No. | W6 | W5 | W4 | W3 | W2 |
|---|---|---|---|---|---|---|
| Ormocarpum flavum | AF189041 | — | — | — | — | 91 bp |
| Ormocarpum keniense | AF068155 | — | — | — | — | — |
| Ormocarpum kirkii | AF068152 | — | — | — | — | — |
| Ormocarpum klainei | AF189044 | — | — | — | — | 91 bp |
| Ormocarpum megalophyllum | AF068154 | — | — | — | — | 91 bp |
| Ormocarpum muricatum | AF068156 | — | — | — | — | 91 bp |
| Ormocarpum orientale | AF068159 | — | — | — | — | 91 bp |
| Ormocarpum pubescens | AF189045 | — | — | — | — | 91 bp |
| Ormocarpum rectangulare | AF189046 | — | — | — | — | — |
| Ormocarpum schliebenii | AF189047 | — | — | — | — | 91 bp |
| Ormocarpum sennoides | AF068153 | — | — | — | — | 91 bp |
| Ormocarpum somalense | AF189048 | — | — | — | — | — |
| Ormocarpum trachycarpum | AF189049 | — | — | — | — | — |
| Ormocarpum trichocarpum | AF068158 | — | — | — | — | — |
| Ormocarpum verrucosum | AF189050 | — | — | — | — | 91 bp |
| Chapmannia floridana | AF203543 | — | — | 462 bp | 35 bp | 226 bp |
| Chapmannia prismatica | AJ320400 | — | — | — | — | — |
| Chapmannia somalensis | AF203544 | — | — | — | — | — |
| Chapmannia gracilis | AF203546 | — | — | — | — | — |
| Chapmannia reghidensis | AF204232 | — | — | — | — | — |

TABLE 7D-continued

Peanut, SEQ NO:18 & SEQ NO:24 primer: Amplification products

| Scientific Name (Common Name) Related Species of the Genus *Arachis* Belonging to Leguminous | GenBank Accession No. | W6 | W5 | W4 | W3 | W2 |
|---|---|---|---|---|---|---|
| *Chapmannia sericea* | AF203548 | — | — | — | — | — |
| *Chapmannia tinireana* | AF203547 | — | — | — | — | — |
| *Ormocarpopsis aspera* | AF068148 | — | — | — | — | — |
| *Ormocarpopsis calcicola* | AF068145 | — | — | — | — | — |
| *Ormocarpopsis itremoensis* | AF068149 | — | — | — | — | 69 bp |
| *Ormocarpopsis mandrarensis* | AF068147 | — | — | — | — | 69 bp |
| *Ormocarpopsis parvifolia* | AF068144 | — | — | — | — | — |
| *Ormocarpopsis tulearensis* | AF068146 | — | — | — | — | 69 bp |
| *Diphysa humilis* | AF068162 | — | — | — | — | 90 bp |
| *Diphysa macrophylla* | AF189029 | — | — | — | — | — |

TABLE 7E

Peanut, SEQ NO:18 & SEQ NO:24 primer: Amplification products

| Scientific Name (Common Name) | GenBank Accession No. | W6 | W5 | W4 | W3 | W2 |
|---|---|---|---|---|---|---|
| Related Species of the Genus *Arachis* Belonging to leguminous | | | | | | |
| *Diphysa suberosa* | AF189034 | — | — | — | — | 90 bp |
| *Fiebrigiella gracilis* | AF203561 | — | — | — | — | — |
| ★*Fissicalyx fendleri* | AF189061 | — | — | 384 bp 302 bp | 349 bp 340 bp 258 bp 150 bp 66 bp | — |
| Related Species of the Genus *Arachis* Not Belonging to Leguminous | | | | | | |
| *Spigelia coelostylioides* | AF177992 | — | — | — | — | — |
| *Spigelia hedyotidea* | AF178005 | — | — | — | — | — |
| *Spigelia marilandica* | AF177991 | — | — | — | — | — |

PCR described above was conducted using primers designed in the present invention. In this case, target 253 to 259 bp amplification products, expected from the simulation results of the ITS-1~5.8S rRNA gene~ITS-2 sequences of the genus *Arachis*, were obtained from 500 to 50 fg of peanut DNA. It is found from the results that even where 500 to 50 fg of peanut DNA is present, the peanut can be detected. In this connection, this sensitivity corresponds to a sensitivity wherein there can be detected 10 to 1 ppm of peanut DNA contained in the sample DNA when PCR was conducted with, as a template, 50 ng of DNA isolated from some samples.

Consequently, in conjunction with the results of specificity studied by PCR simulation, and the results of sensitivity and specificity studied by PCR, it was confirmed that a wide range of plants in the genus *Arachis* including peanut were detectable using the present invention.

Example 6

A. Design of Oligonucleotide Primers for Detection of DNA from Wheat (1) DNA Sequences of the Genus *Triticum*

Regarding the genus *Triticum*, 5.8S rRNA gene, ITS-1 and ITS-2 sequences in the following 29 DNA sequences registered in GenBank were examined to select suitable regions for the primer.

1: *Triticum aestivum* (AF440679)
2: *Triticum aestivum* (AF440676)
3: *Triticum aestivum* (AF438191)
4: *Triticum aestivum* (AF438188)
5: *Triticum aestivum* (AF438187)
6: *Triticum aestivum* (AF438186)
7: *Triticum haeoticum* (AJ238901)
8: *Triticum urartu* (AJ301803)
9: *Triticum turgidum* subsp. *dicoccum* (AJ301801)
10: *Triticum monococcum* (AJ301800)
11: *Triticum aestivum* (AJ301799)
12: *Triticum monococcum* (AJ245404)
13: *Triticum turgidum* (AJ238919)
14: *Triticum turgidum* (AJ238918)
15: *Triticum turgidum* (AJ238917)
16: *Triticum turgidum* (AJ238915)
17: *Triticum turgidum* (AJ238913)
18: *Triticum turgidum* (AJ238912)
19: *Triticum turgidum* (AJ238911)
20: *Triticum timopheevii* (AJ238924)
21: *Triticum timopheevii* (AJ238923)
22: *Triticum tiflopheevii* (AJ238922)
23: *Triticum timopheevii* (AJ238921)
24: *Triticum timopheevii* (AJ238920)
25: *Triticum turgidum* (AJ238916)
26: *Triticum turgidum* (AJ238914)
27: *Triticum urartu* (AJ238902)
28: *Triticum aestivum* (Z11761)
29: *Triticum monococcum* (L11581)

(2) DNA Sequences of other Common Allergenic Plants and Plants Widely Used for a Food Ingredient The DNA sequences described in Example 1 A (2) "DNA Sequences of Other Common Allergenic Plants" and (3) "DNA Sequences of Plants Widely Used for a Food Ingredient" were selected. Regarding buckwheat, 5.8S rRNA gene, ITS-1 and ITS-2 sequences in the following DNA sequences registered in GenBank were selected.

1: Buckwheat: *Fagopyrum esculentum* (AB000330)

(3) DNA Sequences of Rye, Barley and Oats

Regarding rye, barley and oats, 5.8S rRNA gene, ITS-1 and ITS-2 sequences in the following DNA sequences registered in GenBank were selected.

1: Rye: *Secale cereale* (L36504)
2: Barley: *Hordeum vulgare* (AF440678)
3: Oat: *Avena sativa* (Z96893)

(4) DNA Sequences of Related Species of the Genus *Triticum*

As representatives of the DNA sequences of related species of the genus *Triticum*, 5.8S rRNA gene, ITS-1 and ITS-2 sequences in the following 70 DNA sequences registered in GenBank were selected. In this connection, the 70 DNA sequences were selected as representatives of the DNA sequences of related species of the genus *Triticum*, each of which had the highest score in the corresponding genus other than genus *Fagopyrum* and a score of 60 bits or more among sequences of species belonging to the corresponding genus selected from sequences registered in GenBank through a BLAST homology search using the ITS-2 sequence of wheat (*Triticum aestivum* Z11761).

1: Ancestral species of wheat: *Aegilops sharonensis* (AF149195)
2: *Taeniatherum caput-medusae* (L36505)
3: *Agropyron puberulum* (L36482)
4: *Thinopyrunmintermedium* (AF507809)
5: *Lophopyrum elongatum* (L36495)
6: *Pseudoroegneria spicata* (L36502)
7: *Peridictyon sanctum* (L36497)
8: *Australopyrum pectinatum* (L36484)
9: *Amblyopyrum muticum* (AF149202)
10: *Henrardia persica* (L36491)
11: *Ereniopyrunm honaepartis* (L36490)
12: *Crithopsis delileana* (L36487)
13: *Psathyrostachys fragilis* (L36498)
14: *Heteranthelium piliferum* (L36492)
15: *Critesion violaceum* (L36488)
16: *Secale sylvestre* (AJ409210)
17: *Haynaldia villosa* (L36489)
18: *Bromus tectorum* (L36485)
19: *Helictotrichon gervaisii* (AJ389134)
20: *Festuca lasto* (AF303418)
21: *Lagurus ovatus* (AJ389166)
22: *Poa pratensis* (AF171183)
23: *Pseudarrhenatherum longifolium* (AJ389162)
24: *Alopecurus vaginatus* (Z96921)
25: *Calamagrostis epigejos* (AJ306448)
26: *Trisetum spicatum* (AJ389168)
27: *Koeleria pyramidata* (Z96911)
28: *Beckmannia eruciformis* (AJ389164)
29: *Lolitni persicum* (AF171157)
30: *Diarrhena americana* (AF019798)
31: *Arrhenatherum elatius* (AF019795)
32: *Deschampsia christophersenii* (AF486 267)
33: *Piptochaetiwun finmbriatum* (L36523)
34: *Vulpia fasciculata* (AF303402)
35: *Phalaris truncata* (L36522)
36: *Holcus lanatus* (Z96919)
37: *Merxmuellera stricta* (AF019871)
38: *Brachypodiizm mexicanum* (AF019805)
39: *Austrostipa nodosa* (AF019804)
40: *Anipelodesnios mauritanica* (AF019799)
41: *Nassella viridula* (L36521)
42: *Melica imperfecta* (L36519)
43: *Achnatherum hymnenoides* (L36507)
44: *Austrodanthonia auriculata* (AF367604)
45: *Notodanthonia laevis* (AF019875)
46: *Oryzopsis exigua* (AF019801)
47: *Chionochloa rigida* (AF367597)
48: *Thysanolaena maxima* (AF019854)
49: *Monachather paradoxus* (AF019852)
50: *Stipagrostis zeyheri* (AF019845)
51: *Arundo donax* (AF019809)
52: *Zingeria biebersteiniana* (AJ428836)
53: *Centotheca lappacea* (AF019814)
54: *Briza minor* (L36510)
55: *Tribolium hispidum* (AF367602)
56: *Rytidospernma pumilum* (AF019878)
57: *Karroochloa purpurea* (AF019874)
58: *Centropodiag glauca* (AF019861)
59: *Cortaderia archboldii* (AF367620)
60: *Lamprothyrsus peruvianus* (AF367605)
61: *Imnperata cylindrica* (AF345653)
62: *Zizania latifolia* (AF169234)
63: *Prionanthium ecklonii* (AF019866)
64: *Pentaschistis aspera* (AF019865)
65: *Pentanmeris miacrocalycina* (AF019864)
66: *Molinia caerulea* (AF019857)
67: *Dregeochloa pumilla* (AF019853)
68: *Diplopogon setaceus* (AF019851)
69: *Amphipogon amphopogonoides* (AF019850)
70: *Aristida purpurea* (AF019807)

(5) Oligonucleotide Primer Synthesis and Evaluation

Among ITS-2 sequences of the aforementioned 29 DNA sequences of the genus *Triticum*, there was determined nucleotide sequences which would specifically hybridize to all of the 29 DNA sequences of the genus *Triticum* through the study of the sequences. The thus determined nucleotide sequences are indicated as SEQ NOs:28, 29 and 30. Subsequently, the oligonucleotide primers with SEQ NOs:28, 29 and 30 were synthesized.

```
Sense primer
5'-CGG CAT CTG GTC CCT CGT CT-3'     (SEQ NO:28)

Antisense primer
5'-GCG AGG ACG CCC ACC AT-3'         (SEQ NO:29)

5'-GCA AAG ACG CCC ACC AT-3'         (SEQ NO:30)
```

B. PCR Simulation

Regarding the sense and antisense primer pairs, the simulation was conducted with PCR simulation software, Amplify 1.0 (Bill Engels), which is the same as in Example 1 to examine whether target size of amplification products are obtained from the 29 DNA sequences of the genus *Triticum*, the 8 DNA sequences of common allergenic plants other than wheat (buckwheat, peanut, soybean, walnut, *matsutake* mushroom, peach, apple and orange), the 4 DNA sequences of plants widely used for a food ingredient (corn, brown rice, pepper and mustard), the DNA sequences of rye, barley and oat and the DNA sequences of *Aegilops* termed ancestral species of wheat and plants in related species of the genus *Triticum* used for breed improvement of wheat belonging to the tribe Triticeae. The simulation results are shown in Tables 8A to 8F. The meanings of symbols and numerical values in Tables 8A to 8F are explained below.

★: An obtained amplification product whose size almost matched the target 140 bp (±10 bp).

W 2–6: Probability to obtain amplification products
High Probability - - - W6>W5>W4>W3>W2 - - - Low
Probability Numerical values followed by bp:

Each value was obtained by subtracting 2 from the value obtained in the simulation.

(–): No amplification product was predicted.

Related Species of the genus *Tiiticun*:

Sequences similar to the ITS-2 sequence of *Triticum aestivum* (Z11761) were searched by means of a BLAST homology search and the sequences having a score of 60 bits or more were selected from among them. Each sequence having the highest score in each genus and having a score of 60 bits or more is shown in the following Tables 8C–8F as the representative of the DNA sequences of related species of the genus *Triticum*.

C. Preparation of Template DNA for PCR (1) Samples Used for DNA Extraction

Wheat:
  Commercially available seeds of wheat were used.

(2) DNA Isolation from Wheat

A DNA was isolated from wheat in the same way as in Example 1 B (3). The isolated DNA preparation of wheat was diluted stepwise with sterilized ultrapure water to use as template DNA for PCR.

D. PCR

PCR was conducted in the substantially same way as Example 1 C, except for use of the following primers and PCR program.

Primer:

The primer of SEQ NO:28 was used at 0.5 µM of final concentration and each primer of SEQ NOs:29 and 30 was used at 0.25 µM of final concentration.

PCR program:

PCR was conducted according to the following PCR program.

Pre-incubation at 95° C. for 15 min.; thereafter 45 cycles consisting of denaturation at 95° C. for 1 min., annealing at 66° C. for 1 min. and extension at 72° C. for 1 min.; followed by a final extension at 72° C. for 4 min.

The quality of each of the template DNA used here was sufficient enough to be used for PCR based on the result of a separate PCR, in which target products were obtained using a primer pair to amplify a part of plant chloroplast DNA.

E. Results

Regarding the primers of the present invention, the simulation was conducted with PCR simulation software, Amplify 1.0 (Bill Engels) to examine the specificity to ITS-2 sequence of each plant. As a result, as shown in Tables 8A to 8F, it was predicted that target 93 to 95 bp amplification products would be obtained from the aforementioned 29 DNA sequences of the genus *Triticum*. On the other hand, it was predicted that no target 93 to 95 bp amplification product would be obtained from the 8 DNA sequences of common allergenic plants other than wheat (buckwheat, peanut, soybean, walnut, *matsutake* mushroom, peach, apple and orange), the 4 DNA sequences of plants widely used for a food ingredient (corn, brown rice, pepper and mustard), the DNA sequences of rye, barley and oat, the 2 DNA sequences of related species of the genus *Triticum* belonging to the tribe Triticeae and the 51 DNA sequences of related species of the genus *Triticum* not belonging to the tribe Thiticeae. In this connection, it was predicted by simulation that amplification products having almost 93 to 95 bp would be obtained from the DNA sequences of *Aegilops* termed ancestral species of wheat, plants in related species of the genus *Triticum* used for breed improvement of wheat belonging to the tribe Triticeae and some plants in related species of the genus *Triticum* not belonging to tribe Triticeae.

TABLE 8A

Wheat, SEQ No:28 & SEQ NOs:29 and 30 (two types) primer: Amplification products

| Scientific Name (Common Name) Genus *Triticum* | GenBank Accession No. | W6 | W5 | W4 | W3 | W2 |
|---|---|---|---|---|---|---|
| ★*Triticum aestivum* | AF440679 | 94 bp | — | 335 bp 287 bp 218 bp | — | — |
| ★*Triticum aestivum* | AF440676 | 94 bp | — | 335 bp 287 bp 218 bp | — | — |

TABLE 8A-continued

Wheat, SEQ No:28 & SEQ NOs:29 and 30 (two types) primer: Amplification products

| Scientific Name (Common Name) Genus *Triticum* | GenBank Accession No. | W6 | W5 | W4 | W3 | W2 |
|---|---|---|---|---|---|---|
| ★*Triticum aestivum* | AF438191 | — | — | 95 bp | — | 336 bp 288 bp 219 bp |
| ★*Triticum aestivum* | AF438188 | 94 bp | — | 335 bp 287 bp | — | — |
| ★*Triticum aestivum* | AF438187 | 94 bp | — | 335 bp 287 bp 218 bp | — | — |
| ★*Triticum aestivum* | AF438186 | 94 bp | — | 333 bp 285 bp 217 bp | — | — |
| ★*Triticum baeoticum* | AJ238901 | 94 bp | — | — | — | — |
| ★*Triticum urartu* | AJ301803 | 94 bp | — | 334 bp 286 bp 217 bp | — | — |
| ★*Triticum turgidum* subsp. *dicoccum* | AJ301801 | 94 bp | — | 335 bp 287 bp 218 bp | — | — |
| ★*Triticum monococcum* | AJ301800 | 94 bp | — | 286 bp 217 bp | — | — |
| ★*Triticum aestivum* | AJ301799 | 94 bp | — | 284 bp 215 bp | — | — |
| ★*Triticum monococcum* | AJ245404 | 94 bp | — | — | — | — |
| ★*Triticum turgidum* | AJ238919 | 94 bp | — | — | — | — |
| ★*Triticum turgidum* | AJ238918 | 94 bp | — | — | — | — |
| ★*Triticum turgidum* | AJ238917 | 94 bp | — | — | — | — |
| ★*Triticum turgidum* | AJ238915 | 94 bp | — | — | — | — |
| ★*Triticum turgidum* | AJ238913 | 94 bp | — | — | — | — |

TABLE 8B

Wheat, SEQ No:28 & SEQ NOs:29 and 30 (two types) primer: Amplification products

| Scientific Name (Common Name) | GenBank Accession No. | W6 | W5 | W4 | W3 | W2 |
|---|---|---|---|---|---|---|
| Genus *Triticum* | | | | | | |
| ★*Triticum turgidum* | AJ238912 | 94 bp | — | — | — | — |
| ★*Triticum turgidum* | AJ238911 | 94 bp | — | — | — | — |
| ★*Triticum timopheevii* | AJ238924 | 94 bp | — | — | — | — |
| ★*Triticum timopheevii* | AJ238923 | 94 bp | — | — | — | — |
| ★*Triticum timopheevii* | AJ238922 | 93 bp | — | — | — | — |
| ★*Triticum timopheevii* | AJ238921 | 94 bp | — | — | — | — |
| ★*Triticum timopheevii* | AJ238920 | 94 bp | — | — | — | — |
| ★*Triticum turgidum* | AJ238916 | 94 bp | — | — | — | — |
| ★*Triticum turgidum* | AJ238914 | 94 bp | — | — | — | — |
| ★*Triticum urartu* | AJ238902 | 94 bp | — | — | — | — |
| ★*Triticum aestivum* | Z11761 | 94 bp | — | 335 bp 287 bp 218 bp | — | — |
| ★*Triticum monococcum* | L11581 | 94 bp | — | 286 bp 217 bp | — | — |
| Common Allergenic Plants | | | | | | |
| *Arachis hypogaea* (Peanut) | AF156675 | — | — | — | — | 342 bp 146 bp |
| *Fagopyrum esculentum* (Buckwheat) | AB000330 | — | — | — | — | — |
| *Glycine max* (Soybean) | U60551 | — | — | — | — | — |

TABLE 8B-continued

Wheat, SEQ No:28 & SEQ NOs:29 and 30 (two types) primer: Amplification products

| Scientific Name (Common Name) | GenBank Accession No. | W6 | W5 | W4 | W3 | W2 |
|---|---|---|---|---|---|---|
| *Juglans regia* (Walnut) | AF303809 | — | — | — | — | — |
| *Tricholoma matsutake* (Matsutake mushroom) | U62964 | — | — | — | — | — |
| *Prunus persica* (Peach) | AF185621 | — | — | — | — | 215 bp |
| *Malus* x *domestica* (Apple) | AF186484 | — | — | — | — | — |
| *Citrus* sp. (Valencia orange) | E08821 | — | — | — | — | — |
| Plants Widely Used for a Food Ingredient | | | | | | |
| *Zea mays* | U46648 | — | — | — | — | — |
| *Oryza sativa* (Brown rice) | AF169230 | — | — | — | — | 299 bp |
| *Piper nigrum* (Pepper) | AF275197 | — | — | — | — | 225 bp |
| *Sinapis alba* (Mustard) | X15915 | — | — | — | — | — |

TABLE 8C

Wheat, SEQ No:28 & SEQ NOs:29 and 30 (two types) primer: Amplification products

| Scientific Name (Common Name) | GenBank Accession No. | W6 | W5 | W4 | W3 | W2 |
|---|---|---|---|---|---|---|
| Rye, Barley and Oat | | | | | | |
| *Secale cereale* (rye) | L36504 | — | — | — | — | — |
| *Hordeum vulgare* (Barley) | AF440678 | — | — | 287 bp 218 bp | — | — |
| *Avena sativa* (Oat) | Z96893 | — | — | — | — | — |
| Related Species of the Genus *Triticum* Belonging to Tribe Triticeae | | | | | | |
| ★*Aegilops sharonensis* (Ancestral species of wheat) | AF149195 | 94 bp | — | 335 bp 287 bp 218 bp | — | — |
| ★*Taeniatherum caput-medusae* | L36505 | 94 bp | — | 287 bp 218 bp | — | — |
| ★*Agropyron puberulum* | L36482 | 94 bp | — | 287 bp 218 bp | — | — |
| ★*Thinopyrum intermedium* | AF507809 | 94 bp | — | 287 bp 218 bp | — | — |
| ★*Lophopyrum elongatum* | L36495 | 94 bp | — | 334 bp 286 bp 217 bp | — | — |
| ★*Pseudoroegneria spicata* | L36502 | 94 bp | — | 286 bp 217 bp | — | — |
| ★*Peridictyon sanctum* | L36497 | 94 bp | — | 286 bp 217 bp | — | — |
| ★*Australopyrum pectinatum* | L36484 | 94 bp | — | 286 bp 217 bp | — | — |
| ★*Amblyopyrum muticum* | AF149202 | 94 bp | — | 335 bp 287 bp 218 bp | — | — |
| ★*Henrardia persica* | L36491 | 94 bp | — | 334 bp 286 bp 217 bp | — | — |
| ★*Eremopyrum bonaepartis* | L36490 | 94 bp | — | 334 bp 286 bp 217 bp | — | — |
| ★*Crithopsis delileana* | L36487 | 94 bp | — | 335 bp 287 bp 218 bp | — | — |

TABLE 8D

Wheat, SEQ No:28 & SEQ NOs: 29 and 30 (two types) primer: Amplification products

| Scientific Name (Common Name) | GenBank Accession No. | W6 | W5 | W4 | W3 | W2 |
|---|---|---|---|---|---|---|
| Related Species of the Genus *Triticum* Belonging to Tribe Triticeae | | | | | | |
| ★*Psathyrostachys fragilis* | L36498 | 94 bp | — | 335 bp 287 bp 218 bp | — | — |
| ★*Heteranthelium piliferum* | L36492 | 94 bp | — | 286 bp 217 bp | — | — |
| *Critesion violaceum* | L36488 | — | — | 335 bp 287 bp | 218 bp | — |
| *Secale sylvestre* | AJ409210 | — | — | — | — | — |
| Related Species of the Genus *Triticum* Not Belonging to Tribe Triticeae | | | | | | |
| ★*Haynaldia villosa* | L36489 | 94 bp | — | 284 bp 215 bp | — | — |
| ★*Bromus tectorum* | L36485 | 94 bp | — | 286 bp 217 bp | — | — |
| *Helictotrichon gervaisii* | AJ389134 | — | — | — | — | — |
| *Festuca lasto* | AF303418 | — | — | — | — | — |
| ★*Lagurus ovatus* | AJ389166 | — | 94 bp | — | — | — |
| *Poa pratensis* | AF171183 | — | — | — | — | — |
| *Pseudarrhenatherum longifolium* | AJ389162 | — | — | — | — | — |
| *Alopecurus vaginatus* | Z96921 | — | — | — | — | — |
| *Calamagrostis epigejos* | AJ306448 | — | — | — | — | — |
| *Trisetum spicatum* | AJ389168 | — | — | — | — | — |
| *Koeleria pyramidata* | Z96911 | — | — | — | — | — |
| *Beckmannia eruciformis* | AJ389164 | — | — | — | — | — |
| *Lolium persicum* | AF171157 | — | — | — | — | — |
| *Diarrhena americana* | AF019798 | — | — | — | — | — |
| *Arrhenatherum elatius* | AF019795 | — | — | — | — | — |
| *Deschampsia christophersenii* | AF486267 | — | — | — | 332 bp 215 bp | — |
| *Piptochaetium fimbriatum* | L36523 | — | — | — | — | — |
| *Vulpia fasciculata* | AF303402 | — | — | — | — | — |
| *Phalaris truncata* | L36522 | — | — | — | — | — |
| *Holcus lanatus* | Z96919 | — | — | — | — | — |

TABLE 8E

Wheat, SEQ No:28 & SEQ NO:29 and 30 (two types) primer: Amplification products

| Scientific Name (Common Name) Related Species of the Genus *Triticum* Belonging to Tribe Triticeae | GenBank Accession No. | W6 | W5 | W4 | W3 | W2 |
|---|---|---|---|---|---|---|
| *Merxmuellera stricta* | AF019871 | — | — | — | 436 bp 280 bp 211 bp | — |
| *Brachypodium mexicanum* | AF019805 | — | — | — | — | — |
| *Austrostipa nodosa* | AF019804 | | | | | |

TABLE 8E-continued

Wheat, SEQ No:28 & SEQ NO:29 and 30 (two types) primer: Amplification products

| Scientific Name (Common Name) Related Species of the Genus *Triticum* Belonging to Tribe Triticeae | GenBank Accession No. | W6 | W5 | W4 | W3 | W2 |
|---|---|---|---|---|---|---|
| *Ampelodesmos mauritanica* | AF019799 | — | — | — | — | — |
| *Nassella viridula* | L36521 | — | — | — | — | — |
| *Melica imperfecta* | L36519 | — | — | — | 114 bp | — |
| *Achnatherum hymenoides* | L36507 | — | — | — | 286 bp | 217 bp |
| *Austrodanthonia auriculata* | AF367604 | — | — | — | 282 bp | 213 bp |
| *Notodanthonia laevis* | AF019875 | — | — | — | 283 bp | — |
| *Oryzopsis exigua* | AF019801 | — | — | — | — | — |
| *Chionochloa rigida* | AF367597 | — | — | — | 281 bp 212 bp | — |
| *Thysanolaena maxima* | AF019854 | — | — | — | — | — |
| *Monachather paradoxus* | AF019852 | — | — | — | 286 bp | 217 bp 142 bp 73 bp |
| *Stipagrostis zeyheri* | AF019845 | — | — | — | — | — |
| *Arundo donax* | AF019809 | — | — | — | 289 bp | 220 bp |
| *Zingeria biebersteiniana* | AJ428836 | — | — | — | — | — |
| *Centotheca lappacea* | AF019814 | — | — | — | — | — |
| *Briza minor* | L36510 | — | — | — | — | — |
| *Tribolium hispidum* | AF367602 | — | — | — | 282 bp | 213 bp |
| *Rytidosperma pumilum* | AF019878 | — | — | — | 282 bp | 213 bp |
| *Karroochloa purpurea* | AF019874 | — | — | — | 282 bp 213 bp | — |
| *Centropodia glauca* | AF019861 | — | — | — | 281 bp | 212 bp |
| *Cortaderia archboldii* | AF367620 | — | — | — | 280 bp | 211 bp |
| *Lamprothyrsus peruvianus* | AF367605 | — | — | — | 280 bp | 211 bp |
| *Imperata cylindrica* | AF345653 | — | — | — | — | — |

TABLE 8F

Wheat, SEQ No:28 & SEQ No:29 and 30 (two types) primer: Amplification products

| Scientific Name (Common Name) Related Species of the Genus *Triticum* Not Belonging to Tribe Triticeae | GenBank Accession No. | W6 | W5 | W4 | W3 | W2 |
|---|---|---|---|---|---|---|
| *Zizania latifolia* | AF169234 | — | — | — | 311 bp 282 bp 213 bp | — |
| *Prionanthium ecklonii* | AF019866 | — | — | — | 471 bp 283 bp 214 bp | — |
| *Pentaschistis aspera* | AF019865 | — | — | — | 283 bp 214 bp | — |
| *Pentameris macrocalycina* | AF019864 | — | — | — | 283 bp 214 bp | — |
| *Molinia caerulea* | AF019857 | — | — | — | — | — |
| *Dregeochloa pumilla* | AF019853 | — | — | — | 285 bp | — |
| *Diplopogon setaceus* | AF019851 | — | — | — | 285 bp | 216 bp |
| *Amphipogon amphopogonoides* | AF019850 | — | — | — | 285 bp | 216 bp |
| *Aristida purpurea* | AF019807 | — | — | — | — | — |

PCR described above was conducted using primers designed in the present invention. In this case, target 93 to 95 bp amplification products, expected from the simulation results of the ITS-2 sequences of the genus Triticum, were obtained from 500 to 50 fg of wheat DNA. It is found from the results that even where 500 to 50 fg of wheat DNA is present, the wheat can be detected. In this connection, this sensitivity correspond to a sensitivity wherein there can be detected 10 to 1 ppm of peanut DNA contained in the sample DNA when PCR was conducted with, as a template, 50 ng of DNA isolated from some samples.

Consequently, in conjunction with the results of specificity studied by PCR simulation, and the results of sensitivity studied by PCR, it was confirmed that a wide range of the genus *Triticum* including wheat, ancestral species of wheat, and the majority of the tribe Triticeae were specifically detectable at a high sensitivity using the present invention.

Example 7

A. Design of Oligonucleotide Primers for Detection of DNA from Wheat (1) DNA Sequences of the Genus *Glycine*

Regarding the genus *Glycine*, 5.8S rRNA gene, ITS-1 and ITS-2 sequences in the following 50 DNA sequences registered in GenBank were examined to select suitable regions for the primer.

1: *Glycine max* (U60551)
2: *Glycine max* (L36612)
3: *Glycine max* (AF144652)
4: *Glycine max* (AF 144651)
5: *Glycine max* (BI674312)
6: *Glycine soja* (U60550)
7: *Glycine soja* (AF144653)
8: *Glycine soja* (AJ009790)
9: *Glycine soja* (AJ009791)
10: *Glycine soja* (AJ224109)
11: *Glycine max* (AJ011337)
12: *Glycine max* (AJ009787)
13: *Glycinenmax* (AF144654)
14: *Glycine cyrtoloha* (U60548)
15: *Glycine tomentella* (AF023447)
16: *Glycine tomentella* (U60544)
17: *Glycinemicrophylla* (U60537)
18: *Glycine tomentella* (U60542)
19: *Glycine arenaria* (U60543)
20: *Glycine tabacina* (U60539)
21: *Glycine curvata* (U60547)
22: *Glycine tomentella* (AJ011345)
23: *Glycine pindanica* (U60546)
24: *Glycine lactovirens* (U60540)
25: *Glycine albicans* (U60541)
26: *Glycine argyrea* (U60535)
27: *Glycine tomentella* (AF023446)
28: *Glycine latifolia* (U60538)
29: *Glycine clandestina* (U60534)
30: *Glycine tomentella* (AF023445)
31: *Glycine dolichocarpa* (AJ011340)
32: *Glycine dolichocarpa* (AJ224110)
33: *Glycine canescens* (AF023444)
34: *Glycine hirticaulis* (U60545)
35: *Glycine tonientella* (AJ011342)
36: *Glycine dolichocarpa* (AJ011341)
37: *Glycine canescens* (U60533)
38: *Glycine canescens* (AJ011348)
39: *Glycine tabacina* (AJ009788)

40: *Glycine tabacina* (AJ009789)
41: *Glycine latrobeana* (U60536)
42: *Glycine tonmentella* (AJ011344)
43: *Glycine tonmentella* (AJ011343)
44: *Glycine tonientella* (AJ011338)
45: *Glycine tahacina* (AJ011346)
46: *Glycine dolichocarpa* (AJ011339)
47: *Glycine tabacina* (AJ224111)
48: *Glycine falcata* (U60549)
49: *Glycine latifolia* (AJ009786)
50: *Glycine tabacina* (AJ011347)

(2) DNA Sequences of other Common Allergenic Plants and Plants Widely Used for a Food Ingredient The DNA sequences described in Example 1 A (2) "DNA Sequences of Other Common Allergenic Plants" and (3) "DNA Sequences of Plants Widely Used for a Food Ingredient" were selected. Regarding buckwheat, 5.8S rRNA gene, ITS-1 and ITS-2 sequences in the following DNA sequences registered in GenBank were selected.
1: buckwheat: *Fagopyrum esculentum* (AB000330)

(3) DNA Sequences of Leguminous Plants Widely Used for a Food Ingredient

The DNA sequences described in Example 3 A (4) "DNA Sequences of Leguminous Plants Widely Used for a Food Ingredient" were selected. Regarding adzuki bean, ITS-2 sequences in the following DNA sequences registered in GenBank were selected.
1: adzuki bean: *Vigna angularis* var. *nipponensis* (AB060088)

(4) DNA Sequences of Related Species of the Genus *Glycine*

As representatives of the DNA sequences of related species of the genus *Glycine*, 5.8S rRNA gene, ITS-1 and ITS-2 sequences in the following 5 DNA sequences registered in GenBank were selected. In this connection, the 5 DNA sequences were selected as representatives of the DNA sequences of related species of the genus *Glycine*, each of which had the highest score in the corresponding genus other than genus *Glycine* and a score of 60 bits or more among sequences of species belonging to the corresponding genus selected from sequences registered in GenBank through a BLAST homology search using the ITS-2 sequence of soybean (*Glycine max* U6055 1).
1: *Ophrestia radicosa* (AF467484)
2: *Myrospermum sousanum* (AF187086)
3: *Amphicarpaea bracteata* (AF417019)
4: *Amphicarpaea edgeworthii* (AF417013)
5: *Strophostyles umbellata* (AF069115)

(5) Oligonucleotide Primer Synthesis

Among ITS-2 sequences of the aforementioned 50 DNA sequences of the genus *Glycine*, there was determined nucleotide sequences which would specifically hybridize to all of the 50 DNA sequences of the genus *Glycine* through the study of the sequences. The thus determined nucleotide sequences are indicated as SEQ NOs:34 to 41. Subsequently, the oligonucleotide primers with SEQ NOs:34 to 41 were synthesized.

Sense primer:
5'-CTG ACC TCC CGC GAG CAC-3'          (SEQ NO:34)

Antisense primer:
5'-GCG TGG CTC ATC CAC CAT TTT ATC A-3' (SEQ NO:35)

5'-GCG TTG CTC ATC CAC CAT TTT ATC A-3' (SEQ NO:36)

-continued

5'-GCG TTG CTC ATC CAC CAT TTT GTC A-3' (SEQ NO:37)

5'-GCA TTG CTC ATC CAC CAT TTT GTC A-3' (SEQ NO:38)

5'-GCG CTG CTC ATC CGC CAT TTT GTC A-3' (SEQ NO:39)

5'-GCG CTG CTC ATC CAC CAT TTT GTC A-3' (SEQ NO:40)

5'-GCG TGG CTC ATC CAT TTT ATC A-3'    (SEQ NO:41)

CR Simulation

Regarding the sense and antisense primer pairs, the simulation was conducted with PCR simulation software, Amplify 1.0 (Bill Engels), which is the same as in Example 1 to examine whether target size of amplification products are obtained from the 50 DNA sequences of the genus *Glycine*, the 8 DNA sequences of common allergenic plants other than soybean (buckwheat, peanut, wheat, walnut, *matsutake* mushroom, peach, apple and orange), the 4 DNA sequences of plants widely used for a food ingredient (corn, brown rice, pepper and mustard), the 6 DNA sequence of leguminous plants widely used for a food ingredient (French bean, lima bean, lentil, chickpea, mung bean and adzuki bean) and the 5 DNA sequences of related species of the genus *Glycine*. The simulation results are shown in Tables 9A to 9C. The meanings of symbols and numerical values in Tables 9A to 9C are explained below.

★: obtained amplification product whose size almost matched the target 87 to 89 bp (±10 bp).
W 2–6: Probability to obtain amplification products
High Probability - - - W6>W5>W4>W3>W2 - - - Low Probability Numerical values followed by bp:
Each value was obtained by subtracting 2 from the value obtained in the simulation.
(−): No amplification product was predicted.

Related Species of the Genus *Arachis*,

Sequences similar to the ITS-2 sequence of *Glycine max* (U60551) were searched by means of a BLAST homology search and the sequences having a score of 60 bits or more were selected from among them. Each sequence having the highest score in each genus and having a score of 60 bits or more is shown in the following Table 9C as the representative of the DNA sequences of related species of the genus *Glycine*.

C. Preparation of Template DNA for PCR (1) Samples Used for DNA Extraction

Soybean:
Commercially available seeds of soybean were used.

(2) DNA Isolation from Soybean

A DNA was isolated from seeds of soybean in the same way as in Example 1 B (3). The isolated DNA preparation of soybean was diluted step wise with sterilized ultrapure water to use as template DNA for PCR.

D. PCR

PCR was conducted in the substantially same way as Example 1 C, except for use of the following primers and PCR program.

Primer:

The primer of SEQ NO:34 was used at 0.5 µM of final concentration and each primer of SEQ NOs:36 and 37 was used at 0.25 µM of final concentration.

PCR Program:

PCR was conducted according to the following PCR program.

Pre-incubation at 95° C. for 15 min.; thereafter 45 cycles consisting of denaturation at 95° C. for 1 min., annealing at 68° C. for 1 min. and extension at 72° C. for 1 min.; followed by a final extension at 72° C. for 4 min.

The quality of each of the template DNA used here was sufficient enough to be used for PCR based on the result of a separate PCR, in which target products were obtained using a primer pair to amplify a part of plant chloroplast DNA.

E. Results

Regarding the primers of the present invention, the simulation was conducted with PCR simulation software, Amplify 1.0 (Bill Engels) to examine the specificity to ITS-2 sequence of each plant. As a result, as shown in Tables 9A to 9C, it was predicted that target 87 to 89 bp amplification products would be obtained from the aforementioned 50 DNA sequences of the genus *Glycine*. On the other hand, it was predicted that no target 87 to 89 bp amplification product would be obtained from the 8 DNA sequences of other common allergenic plants (buckwheat, peanut, wheat, walnut, *matsutake* mushroom, peach, apple and orange), the 4 DNA sequences of plants widely used for a food ingredient (corn, brown rice, pepper and mustard), the 6 DNA sequence of leguminous plants widely used for a food ingredient (French bean, lima bean, lentil, chickpea, mung bean and adzuki bean) and the 3 DNA sequences of related species of the genus *Glycine* belonging to leguminous plants. In this connection, it was predicted by simulation that amplification products having almost 87 to 89 bp would be obtained from the DNA sequences of *Amphicarpaea edgeworthii* and *Ophrestia radicosa*, but the former can be identified by sequence analysis whether the genus *Glycine* or not and the latter may be able to be identified by appropriately using a commercially available ELISA kit of soybeans and various types of PCR and the like reported.

TABLE 9A

Soybean, SEQ NO:34 & SEQ NOs:35 to 41
(7 types) primer: Amplification products

| Scientific Name (Common Name) Genus *Glycine* | GenBank Accession No. | W6 | W5 | W4 | W3 | W2 |
|---|---|---|---|---|---|---|
| ★*Glycine max* (soybean) | U60551 | 89 bp | — | 162 bp | — | — |
| ★*Glycine max* (soybean) | L36612 | 89 bp | — | 162 bp | — | — |
| ★*Glycine max* (soybean) | AF144652 | 89 bp | — | 162 bp | — | — |
| ★*Glycine max* (soybean) | AF144651 | 89 bp | — | 162 bp | — | — |
| ★*Glycine max* (soybean) | BI674312 | 89 bp | — | 162 bp | — | — |
| ★*Glycine soja* | U60550 | 89 bp | — | 162 bp | — | — |
| ★*Glycine soja* | AF144653 | 89 bp | — | — | — | — |
| ★*Glycine soja* | AJ009790 | 89 bp | — | 161 bp | — | — |
| ★*Glycine soja* | AJ009791 | 89 bp | — | 160 bp | — | — |
| ★*Glycine soja* | AJ224109 | 89 bp | — | 160 bp | — | — |
| ★*Glycine max* (soybean) | AJ011337 | 89 bp | — | 160 bp | — | — |
| ★*Glycine max* (soybean) | AJ009787 | 89 bp | — | 160 bp | — | — |
| ★*Glycine max* (soybean) | AF144654 | 87 bp | — | 155 bp | — | — |
| ★*Glycine cyrtoloba* | U60548 | 89 bp | — | 162 bp | — | — |
| ★*Glycine tomentella* | AF023447 | 89 bp | — | 162 bp | — | — |

TABLE 9A-continued

Soybean, SEQ NO:34 & SEQ NOs:35 to 41
(7 types) primer: Amplification products

| Scientific Name (Common Name) Genus *Glycine* | GenBank Accession No. | W6 | W5 | W4 | W3 | W2 |
|---|---|---|---|---|---|---|
| ★*Glycine tomentella* | U60544 | 89 bp | — | 162 bp | — | — |
| ★*Glycine microphylla* | U60537 | 89 bp | — | 162 bp | — | — |
| ★*Glycine tomentella* | U60542 | 89 bp | — | 162 bp | — | — |
| ★*Glycine arenaria* | U60543 | 89 bp | — | 162 bp | — | — |
| ★*Glycine tabacina* | U60539 | 89 bp | — | 357 bp 162 bp | — | — |
| ★*Glycine curvata* | U60547 | 89 bp | — | 162 bp | — | — |
| ★*Glycine tormentella* | AJ011345 | 89 bp | — | 161 bp | — | — |
| ★*Glycine pindanica* | U60546 | 89 bp | — | 162 bp | — | — |
| ★*Glycine lactovirens* | U60540 | 89 bp | — | 162 bp | — | — |
| ★*Glycine albicans* | U60541 | 89 bp | — | 162 bp | — | — |
| ★*Glycine argyrea* | U60535 | 89 bp | — | 162 bp | — | — |
| ★*Glycine tomentella* | AF023446 | 89 bp | — | 162 bp | — | — |
| ★*Glycine latifolia* | U60538 | 89 bp | — | 357 bp, 162 bp | — | — |
| ★*Glycine clandestina* | U60534 | 89 bp | — | 162 bp | — | — |
| ★*Glycine tomentella* | AF023445 | 89 bp | — | 162 bp | — | — |
| ★*Glycine dolichocarpa* | AJ011340 | 89 bp | — | 161 bp | — | — |

TABLE 9B

Soybean, SEQ NO:34 & SEQ NOs:35 to 41
(7 types) primer: Amplification products

| Scientific Name (Common Name) Genus *Glycine* | GenBank Accession No. | W6 | W5 | W4 | W3 | W2 |
|---|---|---|---|---|---|---|
| ★*Glycine dolichocarpa* | AJ224110 | 89 bp | — | 161 bp | — | — |
| ★*Glycine canescens* | AF023444 | 89 bp | — | 161 bp | — | — |
| ★*Glycine hirticaulis* | U60545 | 89 bp | — | 162 bp | — | — |
| ★*Glycine tomentella* | AJ011342 | 89 bp | — | 161 bp | — | — |
| ★*Glycine dolichocarpa* | AJ011341 | 89 bp | — | 161 bp | — | — |
| ★*Glycine canescens* | U60533 | 89 bp | — | 162 bp | — | — |
| ★*Glycine canescens* | AJ011348 | 89 bp | — | 162 bp | — | — |
| ★*Glycine tabacina* | AJ009788 | 89 bp | — | 160 bp | — | — |
| ★*Glycine tabacina* | AJ009789 | 89 bp | — | 161 bp | — | — |
| ★*Glycine latrobeana* | U60536 | 89 bp | — | 162 bp | — | — |
| ★*Glycine tormentella* | AJ011344 | 89 bp | — | — | — | — |
| ★*Glycine tomentella* | AJ011343 | 89 bp | — | — | — | — |
| ★*Glycine tomentella* | AJ011338 | 89 bp | — | — | — | — |
| ★*Glycine tabacina* | AJ011346 | 89 bp | — | 161 bp | — | — |
| ★*Glycine dolichocarpa* | AJ011339 | 89 bp | — | — | — | — |
| ★*Glycine tabacina* | AJ224111 | 89 bp | — | 161 bp | — | — |
| ★*Glycine falcata* | U60549 | 89 bp | — | 439 bp 184 bp | — | — |
| ★*Glycine latifolia* | AJ009786 | 89 hp | — | 357 bp | — | — |
| ★*Glycine tabacina* | AJ011347 | 89 bp | — | 161 bp | — | — |

TABLE 9C

Soybean, SEQ NO:34 & SEQ NOs:35 to 41
(7 types) primer: Amplification products

| Scientific Name (Common Name) | GenBank Accession No. | W6 | W5 | W4 | W3 | W2 |
|---|---|---|---|---|---|---|
| Other Common Allergenic Plants | | | | | | |
| *Arachis hypogaea* (Peanut) | AF156675 | — | — | — | — | — |

TABLE 9C-continued

Soybean, SEQ NO:34 & SEQ NOs:35 to 41
(7 types) primer: Amplification products

| Scientific Name (Common Name) | GenBank Accession No. | W6 | W5 | W4 | W3 | W2 |
|---|---|---|---|---|---|---|
| *Fagopyrum esculentum* (Buckwheat) | AB000330 | — | — | — | — | — |
| *Triticum aestivum* (Wheat) | AJ301799 | — | — | — | — | — |
| *Juglans regia* (Walnut) | AF303809 | — | — | — | — | — |
| *Tricholoma matsutake* (Matsutake mushroom) | U62964 | — | — | — | — | — |
| *Prunus persica* (Peach) | AF185621 | — | — | — | — | — |
| *Malus* x *domestica* (Apple) | AF186484 | — | — | — | 119 bp | 387 bp 137 bp 121 bp 107 bp 105 bp |
| *Citrus* sp. (Valencia orange) | E08821 | — | — | — | — | — |
| Plants Widely Used for a Food Ingredient | | | | | | |
| *Zea mays* (Corn) | U46648 | — | — | — | — | — |
| *Oryza sativa* (Brown rice) | AF169230 | — | — | — | — | 217 bp |
| *Piper nigrum* (Pepper) | AF275197 | — | — | — | — | 216 bp |
| *Sinapis alba* (Mustard) | X15915 | — | — | — | — | — |
| Leguminous Plants Widely Used for a Food Ingredient | | | | | | |
| *Phaseolus vulgaris* (French bean) | AF115169 | — | — | — | — | 376 bp |
| *Phaseolus lunatus* (Lima bean) | AF115175 | — | — | — | — | — |
| *Lens culinaris* subsp. *culinaris* (Lentil) | AF228066 | — | — | — | — | — |
| *Cicer arietinum* (Chickpea) | AJ237698 | — | — | — | — | — |
| *Vigna radiata* (Mung bean) | X14337 | — | — | — | — | — |
| *Vigna angularis* var. *nipponensis* (Adzuki bean) | AB060088 | — | — | — | — | — |
| Related Species of the Genus *Glycine* Belonging to Leguminous Plants | | | | | | |
| ★*Ophrestia radicosa* | AF467484 | 89 bp | — | 162 bp | — | — |
| *Myrospermum sousanum* | AF187086 | — | — | 161 bp | — | — |
| *Amphicarpaea bracteata* | AF417019 | — | — | — | — | — |
| ★*Amphicarpaea edgeworthii* (Wild bean) | AF417013 | — | 88 bp | — | — | — |
| *Strophostyles umbellata* | AF069115 | — | — | — | — | — |

PCR described above was conducted using primers designed in the present invention. In this case, target 87 to 89 bp amplification products, expected from the simulation results of the ITS-2 sequences of the genus *Glycine,* were obtained from 500 to 50 fg of soybean DNA. It is found from the results that even where 500 to 50 fg of soybean DNA is present, the soybean can be detected. In this connection, this sensitivity corresponds to a sensitivity wherein there can be detected 10 to 1 ppm of soybean DNA contained in the sample DNA when PCR was conducted with, as a template, 50 ng of DNA isolated from some samples.

Consequently, in conjunction with the results of specificity studied by PCR simulation, and the results of sensitivity studied by PCR, it was confirmed that a wide range of the genus *Glycine* including soybean were specifically detectable at a high sensitivity using the present invention.

What is claimed is:

1. A method for detecting species in the genus *Arachis* in cases where even one species of the genus *Arachis* is contained in a subject to which the method is to be applied such as a food ingredient or product, which comprises the steps of:
   a) collecting 45S rRNA precursor gene sequences containing a ITS sequence of the genus *Arachis* and plants thought to be related species thereof and then selecting the region common to the genus *Arachis* in the 45 rRNA precursor gene sequences;
   b) selecting the base specific to the genus *Arachis* from the region;
   c) designing primers (A) and/or (B) having the specific base at 3' end thereof, which primers can hybridize under stringent conditions to a nucleic acid molecule having a common nucleotide base sequence for all species in the genus *Arachis* in 45S rRNA precursor gene sequence thereof, wherein 3' end of primer (A) can complementarily bind to a base in ITS-1 sequence of the genus *Arachis* when the primer hybridizes to the nucleic acid molecule while 3' end of primer (B) can complementarily bind to a base in ITS-2 sequence of the genus *Arachis* when the primer hybridizes to the nucleic acid molecule;
   d) isolating DNA from the subject to which the method is to be applied;
   e) conducting PCR amplification for the isolated DNA using at least one member selected from the group consisting of the primers (A) and (B); and
   f) identifying the presence of the resulting amplification product from PCR containing at least a part of ITS-1 or ITS-2 sequence of the genus *Arachis*.

2. The method of claim 1, wherein the nucleic acid molecule having a common nucleotide sequence for all species in the genus *Arachis* in 45S rRNA precursor gene sequence thereof is a nucleic acid molecule having a common specific nucleotide sequence for all species in the genus *Arachis* in ITS-1 sequence thereof.

3. The method of claim 1, wherein the nucleic acid molecule having a common nucleotide sequence for all species in the genus *Arachis* in 45S rRNA precursor gene sequence thereof is a nucleic acid molecule having a common specific nucleotide sequence for all species in the genus *Arachis* in ITS-2 sequence thereof.

4. The method of claim 2, wherein the step of conducting PCR comprises using the primers (A) and (C), which primer (C) can hybridize under stringent conditions to a nucleic acid molecule having a part of a nucleotide sequence in which ITS-1, 5.8S rRNA gene, ITS-2 and LSU rRNA gene sequences of the genus *Arachis* are continuously bonded.

5. The method of claim 3, wherein the step of conducting PCR comprises using the primers (B) and (D), which primer (D) can hybridize under stringent conditions to a nucleic acid molecule having a part of a nucleotide sequence in which SSU rRNA gene, ITS-1, 5.8S rRNA gene and ITS-2 sequences of the genus *Arachis* are continuously bonded.

6. The method of claim 2, wherein the step of conducting PCR comprises using the primers (A) and (E), which primer (E) can hybridize under stringent conditions to a nucleic acid molecule having a part of a nucleotide sequence in which SSU rRNA gene and ITS-1 sequences of the genus *Arachis* are continuously bonded.

7. The method of claim 3, wherein the step of conducting PCR comprises using the primers (B) and (F), which primer (F) can hybridize under stringent conditions to a nucleic acid molecule having a part of a nucleotide sequence in which ITS-2 and LSU rRNA sequences of the genus *Arachis* are continuously bonded.

8. The method of claim 2, wherein the common specific nucleotide sequence for all species in the genus *Arachis* in ITS-1 sequence thereof is a nucleotide sequence selected from the group consisting of SEQ NO:17 and a complementary nucleotide sequence thereof.

9. The method of claim 1, wherein the primer (A) is selected from the group consisting of SEQ NOs:18, 19 and 20.

10. The method of claim 3, wherein the common specific nucleotide sequence for all species in the genus *Arachis* in ITS-2 sequence thereof is selected from the group consisting of SEQ NO:23 and a complementary nucleotide sequence thereof.

11. The method of claim 1, wherein the primer (B) is SEQ NO:24.

12. The method of claim 9, wherein the step of conducting PCR comprises the steps of conducting PCR amplification at an annealing temperature of the primer and template DNA used in PCR amplification higher than Tm value of the primer, and subsequently continuing the PCR amplification at an annealing temperature near the Tm value.

13. The method of claim 4, wherein the primer (C) can hybridize under stringent conditions to a nucleic acid molecule having a part of a nucleotide sequence in 5.8S rRNA gene sequence of the genus *Arachis*, and 3' end of primer (C) can complementanly bind to a base in 5.8S rRNA gene sequence of the genus *Arachis* when the primer hybridizes to the nucleic acid molecule.

14. The method of claim 5, wherein the primer (D) can hybridize under stringent conditions to a nucleic acid molecule having a part of a nucleotide sequence in 5.8S rRNA gene sequence of the genus *Arachis*, and 3' end of primer (D) can complementarily bind to a base in 5.8S rRNA gene sequence of the genus *Arachis* when the primer hybridizes to the nucleic acid molecule.

15. The method of claim 13, wherein the part of nucleotide sequence in 5.8S rRNA gene sequence of the genus *Arachis* is selected from the group consisting of SEQ NO:1 and a complementary nucleotide sequence thereof.

16. The method of claim 14, wherein the part of nucleotide sequence in 5.8S rRNA gene sequence of the genus *Arachis* is selected from the group consisting of SEQ NO:1 and a complementary nucleotide sequence thereof.

17. The method of claim 4, wherein the primer (C) is selected from the group consisting of SEQ NOs:2, 3 and 4.

18. The method of claim 5, wherein the primer (D) is selected from the group consisting of SEQ NOs:5, 6 and 7.

19. The method of claim 4, wherein the step of conducting PCR comprises using the primer (A) selected from the group consisting of SEQ NOs:18, 19 and 20 and the primer (C) selected from the group consisting of SEQ NOs:2, 3 and 4.

20. The method of claim 1, wherein the step of conducting PCR comprises using the primer (A) selected from the group consisting of SEQ NOs:18, 19 and 20 and the primer (B) of SEQ NO:24.

21. The method of claim 5, wherein the step of conducting PCR comprises using the primer (B) of SEQ NO:24 and the primer (D) selected from the group consisting of SEQ NOs:5, 6 and 7.

* * * * *

SEQUENCE LISTING

<160> NUMBER OF SEQ ID NOS: 41

<210> SEQ ID NO 1
<211> LENGTH: 73
<212> TYPE: DNA
<213> ORGANISM: Fagopyrum esculentum

<400> SEQUENCE: 1
caacggatat ctcggctctc gcatcgatga agaacgtagc gaaatgcgat acttggtgtg    60
aattgcagaa tcc                                                       73

<210> SEQ ID NO 2
<211> LENGTH: 27
<212> TYPE: DNA
<213> ORGANISM: Artificial
<220> FEATURE:
<223> OTHER INFORMATION: PCR primer

<400> SEQUENCE: 2
gcatttcgct acgttcttca tcgatgc                                        27

<210> SEQ ID NO 3
<211> LENGTH: 26
<212> TYPE: DNA
<213> ORGANISM: Artificial
<220> FEATURE:
<223> OTHER INFORMATION: PCR primer

<400> SEQUENCE: 3
atcgcatttc gctacgttct tcatcg                                         26

<210> SEQ ID NO 4
<211> LENGTH: 28
<212> TYPE: DNA
<213> ORGANISM: Artificial
<220> FEATURE:
<223> OTHER INFORMATION: PCR primer

<400> SEQUENCE: 4
agtatcgcat ttcgctacgt tcttcatc                                       28

<210> SEQ ID NO 5
<211> LENGTH: 27
<212> TYPE: DNA
<213> ORGANISM: Artificial
<220> FEATURE:
<223> OTHER INFORMATION: PCR primer

<400> SEQUENCE: 5
gcatcgatga agaacgtagc gaaatgc                                        27

<210> SEQ ID NO 6
<211> LENGTH: 26
<212> TYPE: DNA
<213> ORGANISM: Artificial
<220> FEATURE:
<223> OTHER INFORMATION: PCR primer

<400> SEQUENCE: 6
cgatgaagaa cgtagcgaaa tgcgat                                         26

<210> SEQ ID NO 7
<211> LENGTH: 28
<212> TYPE: DNA
<213> ORGANISM: Artificial
<220> FEATURE:
<223> OTHER INFORMATION: PCR primer

<400> SEQUENCE: 7
gatgaagaac gtagcgaaat gcgatact                                       28

<210> SEQ ID NO 8

```
<211> LENGTH: 71
<212> TYPE: DNA
<213> ORGANISM: Fagopyrum esculentum

<400> SEQUENCE: 8
acgaaccccg gcgcggactg cgccaaggac cacgaacaga agcgcgtccc gagcctcccg      60
gtccccgggc g                                                          71

<210> SEQ ID NO 9
<211> LENGTH: 77
<212> TYPE: DNA
<213> ORGANISM: Fagopyrum esculentum

<400> SEQUENCE: 9
ccgggcggca cggcggcgtc gcgtcgtttc tacgaaacag aacgactctc ggcaacggat      60
atctcggctc tcgcatc                                                    77

<210> SEQ ID NO 10
<211> LENGTH: 58
<212> TYPE: DNA
<213> ORGANISM: Fagopyrum esculentum

<400> SEQUENCE: 10
gccggaaggg cgagctcccc cgaaacacca agtacggcgg gcggacccccg aaggccat      58

<210> SEQ ID NO 11
<211> LENGTH: 25
<212> TYPE: DNA
<213> ORGANISM: Artificial
<220> FEATURE:
<223> OTHER INFORMATION: PCR primer

<400> SEQUENCE: 11
ggaccacgaa cagaagcgcg tcccg                                           25

<210> SEQ ID NO 12
<211> LENGTH: 21
<212> TYPE: DNA
<213> ORGANISM: Artificial
<220> FEATURE:
<223> OTHER INFORMATION: PCR primer

<400> SEQUENCE: 12
cacgaacaga agcgcgtccc g                                               21

<210> SEQ ID NO 13
<211> LENGTH: 21
<212> TYPE: DNA
<213> ORGANISM: Artificial
<220> FEATURE:
<223> OTHER INFORMATION: PCR primer

<400> SEQUENCE: 13
ggaccacgaa cagaagcgcg t                                               21

<210> SEQ ID NO 14
<211> LENGTH: 22
<212> TYPE: DNA
<213> ORGANISM: Artificial
<220> FEATURE:
<223> OTHER INFORMATION: PCR primer

<400> SEQUENCE: 14
cgccaaggac cacgaacaga ag                                              22
```

<210> SEQ ID NO 15
<211> LENGTH: 23
<212> TYPE: DNA
<213> ORGANISM: Artificial
<220> FEATURE:
<223> OTHER INFORMATION: PCR primer

<400> SEQUENCE: 15
cgttgccgag agtcgttctg ttt                                    23

<210> SEQ ID NO 16
<211> LENGTH: 26
<212> TYPE: DNA
<213> ORGANISM: Artificial
<220> FEATURE:
<223> OTHER INFORMATION: PCR primer

<400> SEQUENCE: 16
gtcgttctgt ttmktagaaa cgacgc                                 26

<210> SEQ ID NO 17
<211> LENGTH: 99
<212> TYPE: DNA
<213> ORGANISM: Arachis villosa

<400> SEQUENCE: 17
aacaagaaca aaccccggc gcggaaagcg ccaaggaagc caaacgtttc tgctctcccc    60
gccggctccg gagacggcat ccggtcgggg cgacgagtg                          99

<210> SEQ ID NO 18
<211> LENGTH: 20
<212> TYPE: DNA
<213> ORGANISM: Artificial
<220> FEATURE:
<223> OTHER INFORMATION: PCR primer

<400> SEQUENCE: 18
gcggaaagcg ccaaggaagc                                        20

<210> SEQ ID NO 19
<211> LENGTH: 18
<212> TYPE: DNA
<213> ORGANISM: Artificial
<220> FEATURE:
<223> OTHER INFORMATION: PCR primer

<400> SEQUENCE: 19
cggcttccgg agacggca                                          18

<210> SEQ ID NO 20
<211> LENGTH: 17
<212> TYPE: DNA
<213> ORGANISM: Artificial
<220> FEATURE:
<223> OTHER INFORMATION: PCR primer

<400> SEQUENCE: 20
cggctccgga gacggca                                           17

<210> SEQ ID NO 21
<211> LENGTH: 53
<212> TYPE: DNA
<213> ORGANISM: Fagopyrum esculentum

```
<400> SEQUENCE: 21
agggcacgcc tgtctgggcg tcacgcaccg cgtcgccccc tccccctcct tcc         53

<210> SEQ ID NO 22
<211> LENGTH: 56
<212> TYPE: DNA
<213> ORGANISM: Fagopyrum esculentum

<400> SEQUENCE: 22
aagactacgc atcgcgtcgc gtcgccgcga gccccgggag gaaagacccg agagag      56

<210> SEQ ID NO 23
<211> LENGTH: 57
<212> TYPE: DNA
<213> ORGANISM: Arachis villosa

<400> SEQUENCE: 23
acgggctctt ggtggggagc ggcaccgcgg cagatggtgg tcgagaacaa ccctcgt     57

<210> SEQ ID NO 24
<211> LENGTH: 17
<212> TYPE: DNA
<213> ORGANISM: Artificial
<220> FEATURE:
<223> OTHER INFORMATION: PCR primer

<400> SEQUENCE: 24
ccatctgccg cggtgcc                                                 17

<210> SEQ ID NO 25
<211> LENGTH: 60
<212> TYPE: DNA
<213> ORGANISM: Triticum aestivum

<400> SEQUENCE: 25
tctcaacggg aatcgggatg cggcatctgg tccctcgtct ctcaagggac ggtggaccga  60

<210> SEQ ID NO 26
<211> LENGTH: 57
<212> TYPE: DNA
<213> ORGANISM: Triticum aestivum

<400> SEQUENCE: 26
taccgcgccg gacacagcgc atggtgggcg tcctcgcttt atcaatgcag tgcatcc     57

<210> SEQ ID NO 27
<211> LENGTH: 57
<212> TYPE: DNA
<213> ORGANISM: Triticum aestivum

<400> SEQUENCE: 27
taccgtgtcg aacacagcgc atggtgggcg tctttgcttt atcaactgca gtgcata    57

<210> SEQ ID NO 28
<211> LENGTH: 20
<212> TYPE: DNA
<213> ORGANISM: Artificial
<220> FEATURE:
<223> OTHER INFORMATION: PCR primer

<400> SEQUENCE: 28
cggcatctgg tccctcgtct                                              20
```

```
<210> SEQ ID NO 29
<211> LENGTH: 17
<212> TYPE: DNA
<213> ORGANISM: Artificial
<220> FEATURE:
<223> OTHER INFORMATION: PCR primer

<400> SEQUENCE: 29
gcgaggacgc ccaccat                                                17

<210> SEQ ID NO 30
<211> LENGTH: 17
<212> TYPE: DNA
<213> ORGANISM: Artificial
<220> FEATURE:
<223> OTHER INFORMATION: PCR primer

<400> SEQUENCE: 30
gcaaagacgc ccaccat                                                17

<210> SEQ ID NO 31
<211> LENGTH: 58
<212> TYPE: DNA
<213> ORGANISM: Glycine max

<400> SEQUENCE: 31
gttgctgcgc ggggtgtatg ctgacctccc gcgagcaccc gcctcgtggt tggttgaa    58

<210> SEQ ID NO 32
<211> LENGTH: 65
<212> TYPE: DNA
<213> ORGANISM: Glycine max

<400> SEQUENCE: 32
gttcatggcc gacttcgccg tgataaaatg gtggatgagc cacgctcgag accaatcacg  60
tgcga                                                             65

<210> SEQ ID NO 33
<211> LENGTH: 62
<212> TYPE: DNA
<213> ORGANISM: Glycine max

<400> SEQUENCE: 33
gttcatggcc gacttcgccg tgataaaatg gatgagccac gctcgaccaa acgtgcgacc  60
gg                                                                62

<210> SEQ ID NO 34
<211> LENGTH: 18
<212> TYPE: DNA
<213> ORGANISM: Artificial
<220> FEATURE:
<223> OTHER INFORMATION: PCR primer

<400> SEQUENCE: 34
ctgacctccc gcgagcac                                               18

<210> SEQ ID NO 35
<211> LENGTH: 25
<212> TYPE: DNA
<213> ORGANISM: Artificial
<220> FEATURE:
<223> OTHER INFORMATION: PCR primer

<400> SEQUENCE: 35
```
gcgtggctca tccaccattt tatca    25

<210> SEQ ID NO 36
<211> LENGTH: 25
<212> TYPE: DNA
<213> ORGANISM: Artificial
<220> FEATURE:
<223> OTHER INFORMATION: PCR primer

<400> SEQUENCE: 36
gcgttgctca tccaccattt tatca    25

<210> SEQ ID NO 37
<211> LENGTH: 25
<212> TYPE: DNA
<213> ORGANISM: Artificial
<220> FEATURE:
<223> OTHER INFORMATION: PCR primer

<400> SEQUENCE: 37
gcgttgctca tccaccattt tgtca    25

<210> SEQ ID NO 38
<211> LENGTH: 25
<212> TYPE: DNA
<213> ORGANISM: Artificial
<220> FEATURE:
<223> OTHER INFORMATION: PCR primer

<400> SEQUENCE: 38
gcattgctca tccaccattt tgtca    25

<210> SEQ ID NO 39
<211> LENGTH: 25
<212> TYPE: DNA
<213> ORGANISM: Artificial
<220> FEATURE:
<223> OTHER INFORMATION: PCR primer

<400> SEQUENCE: 39
gcgctgctca tccgccattt tgtca    25

<210> SEQ ID NO 40
<211> LENGTH: 25
<212> TYPE: DNA
<213> ORGANISM: Artificial
<220> FEATURE:
<223> OTHER INFORMATION: PCR primer

<400> SEQUENCE: 40
gcgctgctca tccaccattt tgtca    25

<210> SEQ ID NO 41
<211> LENGTH: 22
<212> TYPE: DNA
<213> ORGANISM: Artificial
<220> FEATURE:
<223> OTHER INFORMATION: PCR primer

<400> SEQUENCE: 41
gcgtggctca tccattttat ca    22